(12) United States Patent
Shinohata et al.

(10) Patent No.: US 8,895,774 B2
(45) Date of Patent: Nov. 25, 2014

(54) PROCESS FOR PRODUCING ISOCYANATES USING DIARYL CARBONATE

(75) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 486 days.

(21) Appl. No.: 12/991,586

(22) PCT Filed: May 15, 2008

(86) PCT No.: PCT/JP2008/058944
§ 371 (c)(1), (2), (4) Date: Nov. 8, 2010

(87) PCT Pub. No.: WO2009/139061
PCT Pub. Date: Nov. 19, 2009

(65) Prior Publication Data
US 2011/0054211 A1    Mar. 3, 2011

(51) Int. Cl.
C07C 263/04    (2006.01)

(52) U.S. Cl.
CPC ........... *C07C 263/04* (2013.01); *C07C 2101/14* (2013.01)
USPC .......................................... 560/345; 560/338

(58) Field of Classification Search
USPC .............................. 528/196; 560/345, 25, 338
See application file for complete search history.

(56) References Cited

U.S. PATENT DOCUMENTS

| | | |
|---|---|---|
| 2,692,275 A | 10/1954 | Bortnick |
| 3,125,598 A | 3/1964 | Kuhle et al. |
| 3,382,289 A | 5/1968 | Edwards et al. |
| 3,734,941 A | 5/1973 | Sydor |
| 3,992,430 A | 11/1976 | Bacskai |
| 4,081,472 A | 3/1978 | Tsumura et al. |
| 4,097,676 A | 6/1978 | Romano |
| 4,123,450 A | 10/1978 | Weber, Jr. |
| 4,290,970 A | 9/1981 | Merger et al. |
| 4,354,979 A | 10/1982 | Schwendemann et al. |
| 4,386,033 A | 5/1983 | Konig et al. |
| 4,388,238 A | 6/1983 | Heitkamper et al. |
| 4,388,246 A | 6/1983 | Sundermann et al. |
| 4,388,426 A | 6/1983 | Schure et al. |
| 4,430,505 A | 2/1984 | Heitkamper et al. |
| 4,480,110 A | 10/1984 | Heitkamper et al. |
| 4,482,499 A | 11/1984 | Merger et al. |
| 4,497,963 A | 2/1985 | Merger et al. |
| 4,514,339 A | 4/1985 | Romano et al. |
| 4,596,678 A | 6/1986 | Merger et al. |
| 4,596,679 A | 6/1986 | Hellbach et al. |
| 4,613,466 A | 9/1986 | Merger et al. |
| 4,659,845 A | 4/1987 | Rivetti et al. |
| 4,692,550 A | 9/1987 | Engbert et al. |
| 4,925,971 A | 5/1990 | Aoki et al. |
| 5,087,739 A | 2/1992 | Bohmholdt et al. |
| 5,315,034 A | 5/1994 | Mizia et al. |
| 5,386,053 A | 1/1995 | Otterbach et al. |
| 5,498,319 A * | 3/1996 | Ehlinger .......................... 203/39 |
| 5,502,244 A | 3/1996 | Okawa et al. |
| 5,616,784 A | 4/1997 | Schwarz et al. |
| 5,688,988 A | 11/1997 | Bosetti et al. |
| 5,698,731 A | 12/1997 | Bosetti et al. |
| 5,731,458 A | 3/1998 | Dahmer et al. |
| 5,883,291 A * | 3/1999 | Schleenstein et al. ......... 560/345 |
| 6,034,265 A | 3/2000 | Bosetti et al. |
| 6,143,917 A | 11/2000 | Harada et al. |
| 6,222,065 B1 | 4/2001 | Okawa et al. |
| 6,992,214 B2 | 1/2006 | Cesti et al. |
| 7,446,218 B2 | 11/2008 | Miyake et al. |
| 2003/0055282 A1 | 3/2003 | Bosman et al. |
| 2003/0125579 A1 | 7/2003 | Yoshida et al. |
| 2005/0080274 A1 | 4/2005 | Miyake et al. |
| 2007/0055042 A1* | 3/2007 | Miyake et al. ................. 528/196 |

(Continued)

FOREIGN PATENT DOCUMENTS

| | | |
|---|---|---|
| CA | 1166649 A1 | 5/1984 |
| CN | 1432563 A | 7/2002 |

(Continued)

OTHER PUBLICATIONS

Dyer et al., "Thermal Degradation of Alkyl N-Phenylcarbamates" Journal of the American Chemical Society, vol. 81, p. 2138-2143, 1959.

(Continued)

*Primary Examiner* — Sudhakar Katakam
*Assistant Examiner* — Pancham Bakshi
(74) *Attorney, Agent, or Firm* — Morgan, Lewis & Bockius LLP

(57) ABSTRACT

An object of the present invention is to provide a process that enables isocyanate to be produced stably over a long period of time and at high yield without encountering problems of the prior art during production of isocyanate without using phosgene. The present invention provides an isocyanate production process including the steps of: obtaining a reaction mixture containing an aryl carbamate having an aryl group originating in a diaryl carbonate, an aromatic hydroxy compound originating in a diaryl carbonate, and a diaryl carbonate, by reacting a diaryl carbonate and an amine compound in the presence of a reaction solvent in the form of an aromatic hydroxy compound; transferring the reaction mixture to a thermal decomposition reaction vessel; and obtaining isocyanate by applying the aryl carbamate to a thermal decomposition reaction, wherein the reaction vessel in which the reaction between the diaryl carbonate and the amine compound is carried out and the thermal decomposition reaction vessel for the aryl carbamate are different.

34 Claims, 16 Drawing Sheets

(56) References Cited

U.S. PATENT DOCUMENTS

| | | |
|---|---|---|
| 2008/0275262 A1 | 11/2008 | Miyake et al. |
| 2010/0029981 A1 | 2/2010 | Shinohata et al. |
| 2010/0069665 A1 | 3/2010 | Shinohata et al. |
| 2011/0054211 A1 | 3/2011 | Shinohata et al. |
| 2011/0092731 A1 | 4/2011 | Shinohata et al. |
| 2011/0319648 A1 | 12/2011 | Shinohata et al. |

FOREIGN PATENT DOCUMENTS

| | | | |
|---|---|---|---|
| CN | 1749241 A | 3/2006 | |
| DE | 925 496 | 3/1955 | |
| EP | 0 125 726 A1 | 11/1984 | |
| EP | 0 320 235 A2 | 6/1989 | |
| EP | 0 355 443 A2 | 2/1990 | |
| EP | 0 446 514 | 9/1991 | |
| EP | 0 957 073 | 11/1999 | |
| EP | 1 640 357 | 3/2006 | |
| GB | 1217122 | 12/1970 | |
| JP | 46-27593 B1 | 8/1971 | |
| JP | 52-71443 | 6/1977 | |
| JP | 52-136147 | 11/1977 | |
| JP | 54-039002 | 3/1979 | |
| JP | S57-082361 A | 5/1982 | |
| JP | 59-108754 | 6/1984 | |
| JP | 60-231640 | 11/1985 | |
| JP | 61-183257 | 8/1986 | |
| JP | 1-230550 | 9/1989 | |
| JP | 4-026665 | 1/1992 | |
| JP | 6-25136 | 2/1994 | |
| JP | 06-056984 | 3/1994 | |
| JP | 6-192204 | 7/1994 | |
| JP | H07-025830 A | 1/1995 | |
| JP | H07-138208 A | 5/1995 | |
| JP | 07-258194 | 10/1995 | |
| JP | H09-025262 A | 1/1997 | |
| JP | 09-087239 | 3/1997 | |
| JP | H09-100265 A | 4/1997 | |
| JP | H09-249632 A | 9/1997 | |
| JP | 10-316645 | 12/1998 | |
| JP | 11-5774 | 1/1999 | |
| JP | H11-001462 A | 1/1999 | |
| JP | 2000-344730 | 12/2000 | |
| JP | 2001-048855 A | 2/2001 | |
| JP | 3-238201 B | 10/2001 | |
| JP | 2001-323106 | 11/2001 | |
| JP | 2002-500654 | 1/2002 | |
| JP | 33-82289 B | 12/2002 | |
| JP | 2003-055332 | 2/2003 | |
| JP | 2003-201275 A | 7/2003 | |
| JP | 2003-525267 | 8/2003 | |
| JP | 2004-244349 | 9/2004 | |
| JP | 2004-262834 | 9/2004 | |
| JP | 2004-262835 | * 9/2004 | ............ C07C 263/04 |
| JP | 2006-069941 | 3/2006 | |
| WO | 95/23484 | 8/1995 | |
| WO | 98/54128 | 12/1998 | |
| WO | 03/055840 | 7/2003 | |
| WO | 2004/014840 | 2/2004 | |
| WO | 2005/000783 | 1/2005 | |
| WO | 2005/111049 | 11/2005 | |
| WO | 2009/066616 A1 | 5/2009 | |

OTHER PUBLICATIONS

Kosa et al., "New combined phenol-hindered amine stabilizers for polymers based on diphenylmethane-4, 4'-diisocyanate and dicyclohexylmethane-4,4'-diisocyanate", Polymer Degradation and Stability, 86(3), p. 391-400, 2004.

Habicher et al., "Synthesis and Antioxidative Properties of Novel Multifunctional Stabilizers" Journal of Vinyl & Additives Technology, vol. 7, No. 1, pp. 4-18, 2001.

Kovacic et al., "Reactions of t-Butylperoxy Isopropyl Carbonate with Aromatic Compounds under Friedel-Crafts Conditions", Journal of Organic Chemistry, vol. 31, No. 8, pp. 2459-2467, 1966.

Petersen, Polyurethans. V. Low-molecular conversion products of diisocyanates, Ann., 562, pp. 205-229, 1949.

Yamazaki et al., "The Reaction of Diphenyl Carbonate with Amines and Its Application to Polymer Synthesis", Journal of Polymer Science, Polymer Chemistry Edition, vol. 17, p. 835-841, 1979.

Tarbell et al., "Acidic and Basic Catalysis in Urethan Formation", Journal of the American Chemical Society, vol. 64 (9), p. 2229-2230, 1942.

STN Accession No. 127:247849 CASREACT structure diagram for Schleenstein et al. US5883291, Mar. 16, 1999.

Kagaku Dai Jiten Henshu Iinkai, Kagaku Dai Jiten 7, vol. 32, Kyoritsu Shuppan Co., Ltd., 1989, pp. 725-728, listed in the International Preliminary Report on Patentability issued Jan. 11, 2011 in PCT/JP2008/058952.

Rudolf Leuckart, "Ueber einige Synthesen mittelst Phenylcyanat", Journal Fur Praktische Chemie, vol. 41, 1890, pp. 301-329, listed in the Supplementary European Search Report dated Sep. 8, 2009 for European Patent Application No. 07831998 (XP002542888, pp. 319-320, Experiment 2 and 4).

Von R. Ohme, et al., "Synthesen mit Brenzcatechincarbonat", Journal Fur Praktische Chemie, 1971, vol. 313, pp. 626-635, listed in the Supplementary European Search Report dated Sep. 8, 2009 for European Patent Application No. 07831998 (XP002542889, p. 630, last paragraph, and p. 631, Tabelle 4).

A. W. Hofmann, Berechte der Deutechen Chemischen Gesellschaft, 1870, vol. 3, p. 653 described in the specification of U.S. Patent Publication No. 2010-0029981A1, at paragraph [0007].

Office Action issued in Canadian Patent Application No. 2,721,357 dated Dec. 31, 2012.

Xylenol Printout http://en.wikipedia.org/wiki/Xylenol, (Feb. 16, 2011).

English language translation of International Preliminary Report on Patentability issued Jan. 11, 2011 in PCT/JP2008/058952.

Office Action issued in corresponding Japanese Patent Application No. 2010-511823 dated Jun. 26, 2013.

Porta et al., "Reactions of Diethyl Carbonate with Amines Catalyzed by Metal Centres," Gazzetta Chimica Italiana, 115: 275-277 (1985).

Office Action issued in Chinese Patent Application No. 200880129186.3 dated Dec. 13, 2012.

Office Action issued in Japanese Patent Application No. 2010-511823 dated Feb. 6, 2013.

* cited by examiner

PROCESS FOR PRODUCING ISOCYANATES USING DIARYL CARBONATE

RELATED APPLICATIONS

The present application is a U.S. National Phase Application of International Application No. PCT/JP2008/058944 (filed May 15, 2008) which is hereby incorporated by reference in their entirety.

TECHNICAL FIELD

The present invention relates to a process for producing isocyanates using diaryl carbonate as a raw material.

BACKGROUND ART

Isocyanates are widely used as raw materials of such products as polyurethane foam, paints, adhesives and the like. The main industrial production process of isocyanates involves reacting amine compounds with phosgene (phosgene method), and nearly the entire amount of isocyanates produced throughout the world are produced according to the phosgene method. However, the phosgene method has numerous problems.

Firstly, this method requires the use of a large amount of phosgene as the raw material. Phosgene is extremely toxic and requires special handling precautions to prevent exposure of handlers thereof, and also requires special apparatuses to detoxify waste.

Secondly, since highly corrosive hydrogen chloride is produced in large amounts as a by-product of the phosgene method, in addition to requiring a process for detoxifying the hydrogen chloride, in many cases hydrolytic chlorine is contained in the isocyanates produced, which may have a detrimental effect on the weather resistance and heat resistance of polyurethane products in the case of using isocyanates produced using the phosgene method.

On the basis of this background, a process for producing isocyanate compounds has been sought that does not use phosgene. One example of a method for producing isocyanate compounds without using phosgene that has been proposed involves thermal decomposition of carbamic acid esters. Isocyanates and hydroxy compounds have long been known to be obtained by thermal decomposition of carbamic acid esters (see, for example, Non-Patent document 1). The basic reaction is illustrated by the following formula:

$$R(NHCOOR')_a \rightarrow R(NCO)_a + a\ R'OH \quad (1)$$

(wherein R represents an organic residue having a valence of a, R' represents a monovalent organic residue, and a represents an integer of from 1 or more).

Among the carbamic acid esters, aryl carbamates, which are carbamic acid esters in which the ester group is an aromatic group, offer the advantage of allowing the temperature of the thermal decomposition reaction to be set to a lower temperature than alkyl carbamates in which the ester group is an alkyl group (see Patent document 1).

Various processes have been disclosed thus far for producing aryl carbamates.

According to the description of Patent document 2, it is described that corresponding aryl alkyl monocarbamates are obtained at a yield of from 90 to 95% by reacting alkyl monoamines with diaryl carbonates in the presence of a solvent such as benzene, dioxane or carbon tetrachloride. In addition, a process has been proposed in Patent document 3 for continuously producing methyl carbamic acid phenyl ester from methyl amine and diphenyl carbonate.

However, all of these processes are processes for producing alkyl aryl carbamates using lower alkyl monoamines as amines, and not aryl alkyl polycarbamates. In the case of producing the corresponding aryl alkyl polycarbamic acid esters from alkyl polyamines such as alkyl diamines or alkyl triamines, completely different problems arise from the case of using alkyl monoamines. This is because, although only urea compounds are produced as by-products by side reactions represented by the following formula (3) and/or formula (4) in addition to the reaction represented by the following formula (2) in the case of using the alkyl monoamines, in the case of the alkyl polyamines such as alkyl diamines or alkyl triamines, extremely numerous types of urea compounds are produced as by-products, such as compounds represented by the following formula (5), formula (6) and/or formula (7).

(2)

(3)

(4)

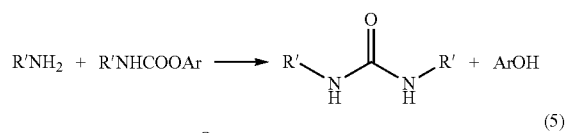

(5)

(6)

(7)

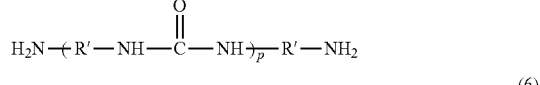

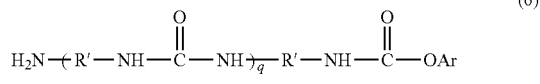

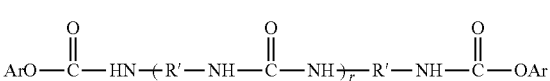

(wherein R' represents a monovalent alkyl group or an aromatic group, Ar represents a monovalent aromatic group, and p, q and r respectively represent an integer of 1 or more).

Namely, reactions resulting in the production of by-products in the form of these various urea compounds cause the problem of decreasing yield of the target compound in the form of the aryl alkyl polycarbamates, as well as the problem of making it extremely difficult to separate and purify the target product from the mixture of these urea compounds and polyurea compounds.

On the basis thereof, although extremely few attempts have been made to produce aryl alkyl polycarbamic acid esters from alkyl polyamines and diaryl carbonates, a very small number of attempts have been reported. For example, according to the specification of Patent document 4, a process has been proposed for obtaining 1,6-hexamethylene dicarbamic acid phenyl ester in a reaction system in which a solution, in which 1 mole of 1,6-hexamethylene diamine is dissolved in 5-times moles of benzene, is dropped into a solution, in which 1 mole of diphenyl carbonate is dissolved in 5-times moles of benzene, while stirring at 80° C. According to this patent specification, it is important to use solvents in which the 1,6-hexamethylene dicarbamic acid phenyl ester dissolves as little as possible for the reaction solvent in order to allow the reaction to proceed advantageously, and solvents such as benzene or chlorobenzene are described as being preferable examples of such solvents.

From this viewpoint, the target 1,6-hexamethylene dicarbamic acid phenyl ester is obtained in Non-Patent document 3 by carrying out a reaction between 0.01 mole of diphenyl carbonate and 0.005 moles of 1,6-hexamethylene diamine using 40 mL of toluene for the reaction solvent for the long period of time of 20 hours. However, the yield is only 93% despite the use of this large amount of toluene, and the problem of the production of by-products in the form of urea compounds and polyurea compounds that must be separated remains.

In addition, Patent document 5 discloses a production process of diurethane compounds in which diaryl carbonates and amine compounds are reacted in the presence of protic acids. However, in the case of carrying out the production process disclosed in this patent publication industrially, the yield of the diurethane compound cannot be said to be adequate and it is necessary to carry out the reaction at a low temperature to inhibit side reactions, thereby resulting in the disadvantage of a long reaction time.

Patent document 6 describes a process in which diaryl carbonates and aromatic polyamines are reacted in the presence of heterocyclic tertiary amines such as 2-hydroxypyridine. In addition to this process requiring an expensive catalyst equal to or greater than an equimolar amount based on the reaction substrate, it also has the problem of the reaction rate being low.

According to Patent document 7, although a process is described for synthesizing aromatic urethanes at a temperature of from 140 to 230° C. in the presence of aromatic amines, diaryl carbonate and Lewis acid catalyst, in the case of this process as well, the use of a Lewis acid causes corrosion of the apparatus and separation and recovery of the product is difficult.

In Patent document 8, a production process of alkyl polycarbamic acid aryl esters is disclosed comprising carrying out reaction in a substantially homogeneous solution state using from 1 to 3 equivalents of diaryl carbonate per equivalent of alkyl polyamine amino groups and using aromatic hydroxy compounds for the reaction solvent when producing alkyl polycarbamic acid aryl esters by reacting alkyl polyamines and diaryl carbonates. According to this patent publication, alkyl polycarbamic acid aryl esters are obtained at high selectivity and a high yield of generally 96% or more, and 98% or more in a preferable aspect thereof. However, since the formation of urea compounds has been confirmed, albeit in small amounts, the formation of urea compounds cannot be completely avoided.

On the other hand, thermal decomposition of carbamic acid esters is susceptible to the simultaneous occurrence of various irreversible side reactions such as thermal denaturation reactions undesirable for carbamic acid esters or condensation of isocyanates formed by the thermal decomposition. Examples of these side reactions include a reaction in which urea bonds are formed as represented by the following formula (8), a reaction in which carbodiimides are formed as represented by the following formula (9), and a reaction in which isocyanurates are formed as represented by the following formula (10) (see Non-Patent document 1 and Non-Patent document 2).

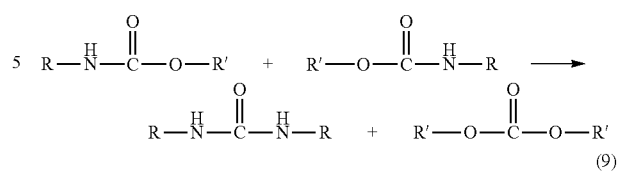

(8)

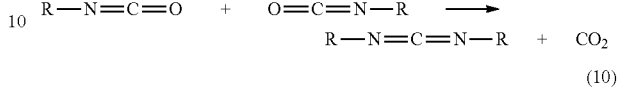

(9)

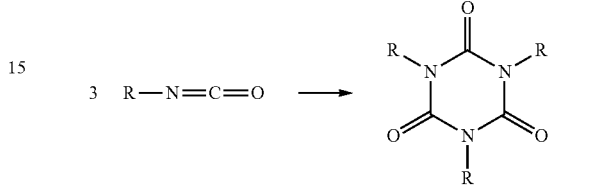

(10)

In addition to these side reactions leading to a decrease in yield and selectivity of the target isocyanates, in the production of polyisocyanates in particular, these reactions may make long-term operation difficult as a result of, for example, causing the precipitation of polymeric solids that clog the reaction vessel.

Various methods have been proposed for producing isocyanates using carbamic acid esters as raw materials.

According to Patent document 9, aromatic diisocyanates and/or polyisocyanates are produced by going through the following two steps. More specifically, in the first step, aromatic primary amines and/or aromatic primary polyamines are reacted with O-alkyl carbamates in the presence or absence of a catalyst and in the presence or absence of urea and alcohol to form aryl diurethanes and/or aryl polyurethanes followed by removal of the ammonia formed as necessary. In the second step, aromatic isocyanates and/or aromatic polyisocyanates are obtained by thermal decomposition of the aryl diurethanes and/or aryl polyurethanes.

Several processes are known for forming the corresponding isocyanates and alcohols by thermal decomposition of (cyclic) aliphatic, and particularly aromatic monourethanes and diurethanes, examples of which include a process carried out at a high temperature in a gaseous phase, and a process carried out under comparatively low temperature conditions in a liquid phase. However, since there are cases in which, for example, the reaction mixture forms precipitates, polymeric substances and closed compounds in the reaction vessel and recovery apparatus due to the occurrence of side reactions as previously described, or these substances form substances that adhere to the walls of the reaction vessel, economic efficiency is poor in the case of producing isocyanates over a long period of time.

Thus, chemical methods, such as the use of a special catalyst (see Patent document 10 and Patent document 11) or a catalyst combined with an insert solvent (see Patent document 12) are disclosed for improving yield during thermal decomposition of urethane.

More specifically, Patent document 13 describes a process for producing hexamethylene diisocyanate involving thermal decomposition of hexamethylene diethyl urethane in the presence of dibenzyl toluene used as a solvent and in the presence of a catalyst mixture containing methyl toluene sulfonate and diphenyl tin dichloride. However, since there is no detailed description of production of the starting components, isolation or purification and arbitrary recovery of the solvent and catalyst mixture, the economic effects of this process were unable to be assessed.

According to the process described in Patent document 14, urethane can be easily decomposed to isocyanate and alcohol in a carbon-containing fluidized bed without using a catalyst. In addition, according to the description of Patent document 15, hexamethylene dialkyl urethane can be decomposed in a gaseous phase at a temperature exceeding 300° C. in the presence or absence of a gas-permeable packaging material composed of, for example, carbon, copper, bronze, steel, zinc, aluminum, titanium, chromium, cobalt or quartz, resulting in the formation of hexamethylene diisocyanate. According to the description of Patent document 14, the process is carried out in the presence of a hydrogen halide and/or hydrogen halide donor. However, this process is unable to achieve a yield of hexamethylene diisocyanate of 90% or more. This is because the decomposition product partially rebonds resulting in the formation of urethane bonds. Thus, purification of the hexamethylene diisocyanate by distillation is still required, and there are numerous cases in which yield loss increases.

Moreover, Patent document 16 discloses that monocarbamates can be advantageously decomposed at high yield without using a solvent under a reduced pressure and/or in the presence of absence of a stabilizer and at a comparatively low temperature. The decomposition products (monoisocyanates and alcohols) are removed by distillation from a boiling reaction mixture and captured separately by fractional condensation. A method for partially removing the reaction mixture is generically described in order to remove by-products formed during thermal decomposition. Thus, although it is possible to remove by-products from the bottom of the reaction vessel, the problem of the case of substances adhering to the walls of the reaction vessel as previously described remains, and problems regarding long-term operation are unresolved. In addition, there is no description regarding the industrial use of the removed residual substances (containing large amounts of useful components).

According to the description of Patent document 17, thermal decomposition of aliphatic, alicyclic or aromatic polycarbamates is carried out at from 150 to 350° C. and from 0.001 to 20 bar, in the presence of an inert solvent, and in the presence or absence of a catalyst and assistant in the form of hydrogen chloride, organic acid chloride, alkylation agent or organic tin compound. By-products formed can be removed continuously from the reaction vessel together with the reaction solution, for example, and corresponding amounts of fresh solvent or recovered solvent are added simultaneously. Examples of disadvantages of this process include a decrease in the space time yield of polyisocyanate due to the use of a circulating solvent, and a large energy requirement, including recovery of the solvent. Moreover, since the assistant used is volatile under the reaction conditions, contamination of the decomposition products can occur. In addition, since there is a large amount of residual substances formed relative to the polyisocyanate formed, there is some doubt regarding economic efficiency and reliability as an industrial process.

Patent document 18 describes a process for continuous thermal decomposition of carbamates supplied along the inner walls of a tubular reaction vessel in the form of a liquid in the presence of a high boiling point solvent, an examples of which may include 5-(ethoxycarbonylamino)-1-(ethoxycarbonylaminomethyl)-1,3,3-trimethylcyclohexane as the alicyclic diurethane. This process has the shortcomings of low yield and low selectivity during production of (cyclic) aliphatic diisocyanates. In addition, there is no description of a continuous method accompanying recovery of rebonded or partially decomposed carbamates, nor is there any mention of post-treatment of solvent containing by-products and catalyst.

The production of isocyanates using diaryl carbonates and amino compounds as raw materials can easily be imagined to be possible by combining the aryl carbamate production processes and isocyanate production processes using thermal decomposition of carbamic acid esters as described above. However, in order to combine these aryl carbamate production processes and isocyanate production processes using thermal decomposition of aryl carbamates as described above, methods involving a complex procedure consisting of carrying out the thermal decomposition of aryl carbamate by reacting diaryl carbonates and amine compounds and separating the aryl carbamates from the resulting reaction solution followed by thermal decomposition of the aryl carbamates, or methods using the reaction solution obtained during production of aryl carbamates directly in the thermal decomposition reaction, must be employed.

In this regards, Patent document 19 discloses a process for synthesizing aromatic isocyanates by synthesizing urethane compounds by reacting aromatic amines and diaryl carbonates in the presence of a Lewis acid catalyst and continuing with thermal decomposition of the urethane compounds in the diaryl carbonates used to synthesize the urethane compounds. In this patent publication, isocyanates are produced by applying a urethane-containing reaction solution obtained by reacting amine compounds and diaryl carbonates in the presence of a Lewis acid catalyst to a thermal decomposition reaction in the reaction vessel used for the urethane synthesis.

Patent document 1: U.S. Pat. No. 3,992,430
Patent document 2: Japanese Patent Application Laid-open No. S52-71443
Patent document 3: Japanese Patent Application Laid-open No. S61-183257
Patent document 4: German Patent No. 925496
Patent document 5: Japanese Patent Application Laid-open No. H10-316645
Patent document 6: Japanese Patent Application Laid-open No. S52-136147
Patent document 7: Japanese Patent Application Laid-open No. 2004-262834
Patent document 8: Japanese Patent Application Laid-open No. H1-230550
Patent document 9: U.S. Pat. No. 4,290,970
Patent document 10:U.S. Pat. No. 2,692,275
Patent document 11: U.S. Pat. No. 3,734,941
Patent document 12: U.S. Pat. No. 4,081,472
Patent document 13: U.S. Pat. No. 4,388,426
Patent document 14: U.S. Pat. No. 4,482,499
Patent document 15: U.S. Pat. No. 4,613,466
Patent document 16:U.S. Pat. No. 4,386,033
Patent document 17:U.S. Pat. No. 4,388,246
Patent document 18: U.S. Pat. No. 4,692,550
Patent document 19: Japanese Patent Application Laid-open No. 2004-262835
Non-Patent document 1: Berchte der Deutechen Chemischen Gesellschaft, Vol. 3, p. 653, 1870
Non-Patent document 2: Journal of American Chemical Society, Vol. 81, p. 2138, 1959
Non-Patent document 3: Journal of Polymer Science, Polymer Chemistry Edition, Vol. 17, p. 835, 1979

DISCLOSURE OF THE INVENTION

Problems to be Solved by the Invention

However, it is not possible to select reaction vessels and reaction conditions each suitable for a urethane compound synthesis reaction and thermal decomposition reaction because of carrying out the urethane compound synthesis reaction and the thermal decomposition reaction in the same reaction vessel. According to the examples of Patent document 19, the yield of isocyanates actually decreases. In addition, this patent publication does not provide a detailed description of a process for continuously producing isocyanates, and is not satisfactory from the viewpoint of an industrially efficient process for producing isocyanate.

In this manner, a process for producing isocyanates using diaryl carbonates and amine compounds as raw materials to produce aryl carbamates followed by producing the isocyanates by going through the aryl carbamates still has numerous problems to be overcome and has not yet been applied industrially.

An object of the present invention is to provide an isocyanate production process that overcomes the various problems of the prior art as described above by using the diaryl carbonates and the amine compounds.

Means for Solving the Problems

As a result of conducting extensive studies on the above-mentioned problems, the inventors of the present invention found a process for producing isocyanates by transferring a mixture obtained by reacting diaryl carbonates and amine compounds under specific conditions to a thermal decomposition reaction vessel under specific conditions and applying carbamic acid ester contained in the mixture to a thermal decomposition reaction, thereby leading to completion of the present invention.

Namely, the present invention provides the following:

[1] a process for producing an isocyanate, comprising the steps of:

obtaining a reaction mixture containing an aryl carbamate having an aryl group originating from a diaryl carbonate, an aromatic hydroxy compound originating from a diaryl carbonate, and a diaryl carbonate, by reacting the diaryl carbonate and an amine compound in a reaction vessel in which a reaction between the diaryl carbonate and the amine compound is carried out;

transferring the reaction mixture to a thermal decomposition reaction vessel connected by a line with the reaction vessel in which the reaction between the diaryl carbonate and the amine compound is carried out; and obtaining the isocyanate by applying the aryl carbamate to a thermal decomposition reaction.

[2] the process according to item [1], further comprising cleaning a high boiling point by-product adhered to the thermal decomposition reaction vessel, with an acid.

[3] the process according to item [1] or [2], wherein the reaction between the diaryl carbonate and the amine compound is carried out at a stoichiometric ratio of the diaryl carbonate to amino groups constituting the amine compound being 1 or more.

[4] the process according to any one of items [1] to [3], wherein the diaryl carbonate and the amine compound are reacted in the presence of an aromatic hydroxy compound as a reaction solvent.

[5] the process according to item [4], wherein the aromatic hydroxy compound as the reaction solvent is an aromatic hydroxy compound having the same type as a compound ArOH having a structure in which a hydrogen atom is added to an ArO group constituting the diaryl carbonate ArOCOOAr (wherein Ar represents an aromatic group and O represents an oxygen atom).

[6] the process according to any one of items [1] to [5], wherein the reaction mixture is supplied to the thermal decomposition reaction vessel in a form of a liquid.

[7] the process according to item [6], wherein the reaction mixture is supplied to the thermal decomposition reaction vessel while maintaining a temperature range of from 10 to 180° C.

[8] the process according to any one of items [1] to [7], wherein the reaction mixture is continuously supplied to the thermal decomposition reaction vessel.

[9] the process according to any one of items [1] to [8], wherein a low boiling point component formed in the thermal decomposition reaction is recovered from the thermal decomposition reaction vessel in a form of a gaseous phase component, and a liquid phase component is recovered from a bottom of the reaction vessel.

[10] the process according to item [9], wherein recovery of the gaseous phase component and recovery of the liquid phase component are carried out continuously.

[11] the process according to item [9] or [10], wherein the isocyanate obtained by a thermal decomposition reaction of the aryl carbamate is recovered from the thermal decomposition reaction vessel in a form of a gaseous phase component, and a liquid phase component containing the diaryl carbonate is recovered from the bottom of the reaction vessel.

[12] the process according to item [11], further comprising recovering the isocyanate by distillative separation, with a distillation column, of the gaseous phase component containing the isocyanate recovered from the thermal decomposition reaction vessel, and supplying the gaseous phase component containing the isocyanate recovered from the thermal decomposition reaction vessel to the distillation column in a form of a gaseous phase.

[13] the process according to item [11] or [12], wherein the liquid phase component containing the diaryl carbonate is a mixture containing the aryl carbamate, and all or a portion of the mixture is supplied to an upper portion of the reaction vessel.

[14] the process according to item [9] or [10], wherein the isocyanate obtained by the thermal decomposition reaction of the aryl carbamate is recovered from the bottom of the reaction vessel in which the thermal decomposition reaction is carried out in a form of a liquid phase component.

[15] the process according to item [14], wherein the liquid phase component recovered from the bottom of the reaction vessel comprises the isocyanate and the aryl carbamate, all or a portion of the isocyanate is separated from the liquid phase component, and all or a portion of a remainder is supplied to the upper portion of the reaction vessel.

[16] the process according to item [14] or [15], wherein the isocyanate is recovered by distillative separation of a mixture containing the isocyanate recovered from the thermal decomposition reaction vessel.

[17] the process according to any one of items [1] to [16], wherein a type of the reaction vessel in which the reaction between the diaryl carbonate and the amine compound is carried out and a type of the thermal decomposition reaction vessel may be the same or different, and the reaction vessel in which the reaction between the diaryl carbonate and the amine compound is carried out and the thermal decomposition reaction vessel is at least one reaction vessel selected from the group consisting of a column-type reaction vessel and a tank-type reaction vessel.

[18] the process according to item [17], wherein the thermal decomposition reaction vessel is composed of at least one reaction vessel selected from the group consisting of an evaporator, a continuous multistage distillation column, a packed column, a thin film evaporator and a falling film evaporator.

[19] the process according to any one of items [1] to [18], wherein the reaction between the diaryl carbonate and the amine compound is carried out in the presence of a catalyst.

[20] the process according to any one of items [1] to [19], wherein the thermal decomposition reaction is carried out in a liquid phase.

[21] the process according to any one of items [1] to [20], wherein the diaryl carbonate is a compound represented by the following formula (1):

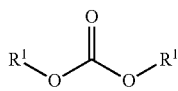
(1)

(wherein $R^1$ represents an aromatic group having 6 to 12 carbon atoms).

[22] the process according to item [21], wherein the diaryl carbonate comprise a metal atom at from 0.001 ppm to 10%.

[23] the process according to item [22], wherein the metal atom is one kind or a plurality of kinds of the metal atoms selected from the group consisting of iron, nickel, cobalt, zinc, tin, copper and titanium atoms.

[24] the process according to any one of items [1] to [23], wherein the diaryl carbonate is a diaryl carbonate produced by a process which comprises the following steps (1) to (3):

step (1): obtaining a reaction mixture containing a dialkyl carbonate by reacting an organic tin compound having a tin-oxygen-carbon bond and carbon dioxide;

step (2): obtaining the dialkyl carbonate and a residue liquid by separating the reaction mixture; and step (3): obtaining the diaryl carbonate by reacting the dialkyl carbonate separated in step (2) and an aromatic hydroxy compound A followed by recovering a by-product alcohol.

[25] the process according to item [24], wherein the aromatic hydroxy compound A is an aromatic hydroxy compound having 6 to 12 carbon atoms.

[26] the process according to item [24] or [25], wherein the diaryl carbonate is a diaryl carbonate produced by a process which further comprises the following steps (4) and (5):

step (4): forming an organic tin compound having a tin-oxygen-carbon bond and water by reacting the residue liquid obtained in step (2) with an alcohol followed by removing the water from a reaction system; and step (5): reusing the organic tin compound having the tin-oxygen-carbon bond obtained in step (4) as the organic tin compound having a tin-oxygen-carbon bond of step (1).

[27] the process according to item [24], wherein the alcohol recovered in step (3) is used as all or a portion of the alcohol of the step (4).

[28] the process according to any one of items [9] to [27], wherein the diaryl carbonate is separated and recovered from the liquid phase component or gaseous phase component recovered from the thermal decomposition reaction vessel, and the diaryl carbonate is reused as a diaryl carbonate used as a starting material.

[29] the process according to item [1] or [24], wherein an aromatic hydroxy compound is separated and recovered from the liquid phase component or gaseous phase component recovered from the thermal decomposition reaction, and the aromatic hydroxy compound is recycled for use as the aromatic hydroxy compound A of the step (3) or as the aromatic hydroxy compound used as the reaction solvent.

[30] the process according to any one of items [1] to [29], wherein the amine compound is a polyamine compound.

[31] the process according to item [30], wherein the amine compound is a compound represented by the following formula (2):

(2)

(wherein $R^2$ represents a group selected from the group consisting of an aliphatic group having 1 to 20 carbon atoms and an aromatic group having 6 to 20 carbon atoms, the above group containing an atom selected from a carbon atom and an oxygen atom, and having a valence equal to n, and n represents an integer of from 2 to 10).

[32] the process according to item [31], wherein the amine compound is a diamine compound in which n is 2 in the formula (2).

[33] the process according to any one of items [1] to [32], wherein the supply of the amine compound to the reaction vessel in which a carbonic acid ester and the amine compound are reacted is carried out in a liquid state.

[34] the process according to any one of items [1] to [33], wherein the supply of the amine compound to the reaction vessel in which a carbonic acid ester and the amine compound are reacted is carried out in a form of a mixture comprising an alcohol, a water or the carbonic acid ester.

Advantageous Effects of the Invention

According to the process of the present invention, isocyanates can be efficiently produced continuously over a long period of time by using diaryl carbonates and amine compounds as raw materials.

Figure 12:
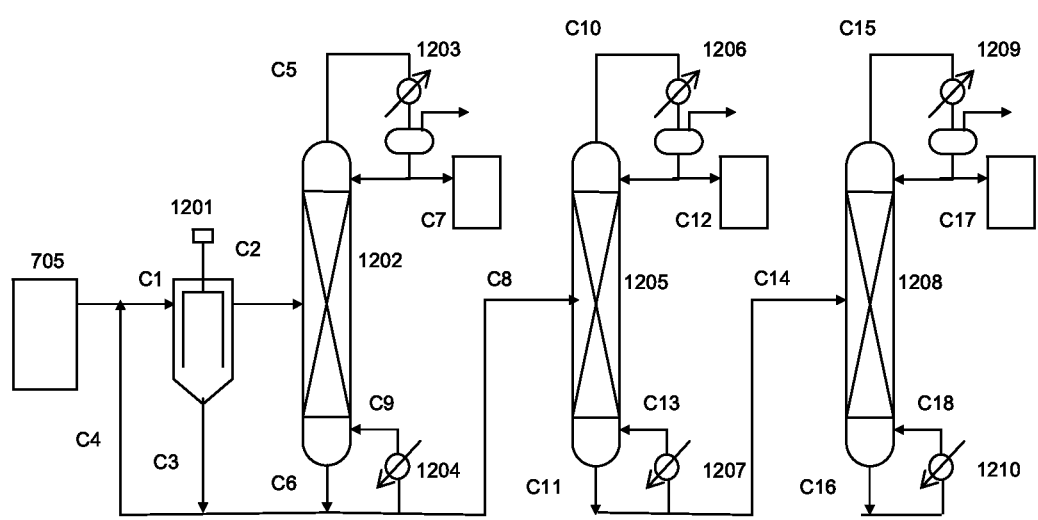
FIG. 12 is a conceptual drawing showing an isocyanate production apparatus according to an embodiment of the present invention.
Figure 13:
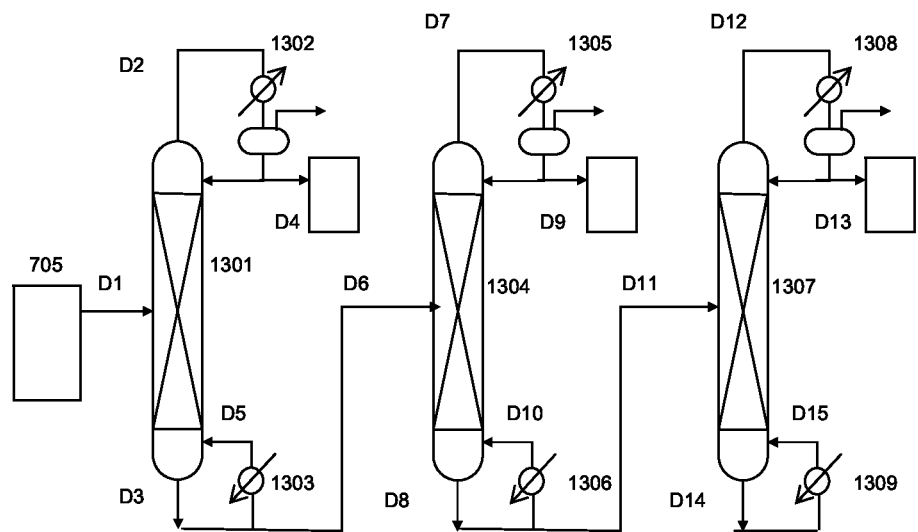
FIG. 13 is a conceptual drawing showing an isocyanate production apparatus according to an embodiment of the present invention.
Figure 15:
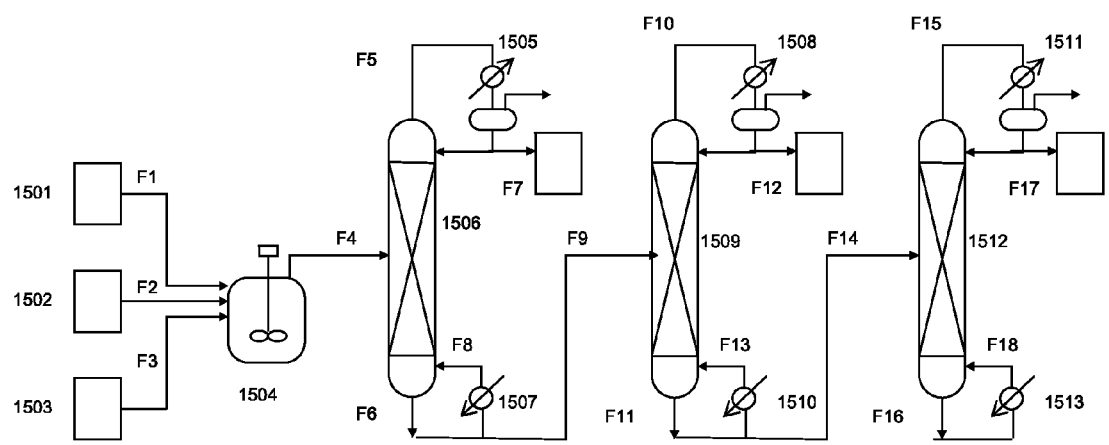
FIG. 15 is a conceptual drawing showing an isocyanate production apparatus according to an embodiment of the present invention.
Figure 16:
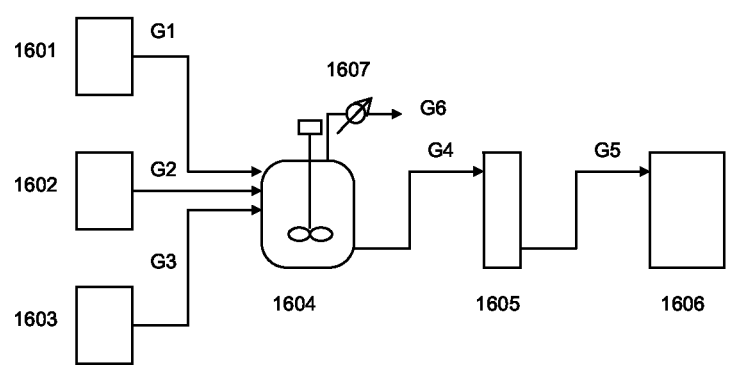
FIG. 16 is a conceptual drawing showing an aryl carbamate production apparatus according to an embodiment of the present invention.

BRIEF DESCRIPTION OF REFERENCE NUMERALS (in FIG. 1)
101, 107: distillation column
102: column-type reaction vessel
103, 106: thin film evaporator
104: autoclave
105: decarbonization tank
111, 112, 117: reboiler
121, 123, 126, 127: condenser
1, 2, 3, 4, 5, 6, 7, 8, 9, 10, 11, 12, 13, 14, 15, 16, 17: line
(in FIG. 2)
202: continuous multistage distillation column
205, 206: storage tank
201: preheater
203: condenser
204: reboiler
21, 22, 23, 24, 25: line
(in FIG. 3)
302: continuous multistage distillation column
305, 306: storage tank
301: preheater
303: condenser
304: reboiler
31, 32, 33, 34, 35: line
(in FIG. 4)
402: continuous multistage distillation column
405, 406: storage tank
401: preheater
403: condenser
404: reboiler
41, 42, 43, 44, 45: line
(in FIG. 5)
502: continuous multistage distillation column
505, 506: storage tank
501: preheater
503: condenser
504: reboiler
51, 52, 53, 54, 55: line
(in FIG. 6)
602: continuous multistage distillation column
605, 606: storage tank
601: preheater
603: condenser
604: reboiler
61, 62, 63, 64, 65: line
(in FIG. 7)
701, 702, 703, 705: storage tank
704: baffled reaction vessel
71, 72, 73, 74: line
(in FIG. 8)
801: thin film evaporator
802, 803: continuous multistage distillation column
808, 809, 810: storage tank
803, 806: condenser
804, 807: reboiler
81, 82, 83, 84, 85, 86, 87, 88, 89, 90, 91, 92, 93, 94: line
(in FIG. 9)
902: continuous multistage distillation column
905, 906: storage tank
901: preheater
903: condenser
904: reboiler
95, 96, 97, 98, 99: line
(in FIG. 10)
1002: continuous multistage distillation column
1005, 1006: storage tank
1001: preheater
1003: condenser
1004: reboiler
A1, A2, A3, A4, A5: line
(in FIG. 11)
1102: continuous multistage distillation column
1105, 1106: storage tank
1101: preheater
1103: condenser
1104: reboiler
B1, B2, B3, B4, B5: line
(in FIG. 12)
1201: thin film evaporator
1202, 1205, 1208: continuous multistage distillation column
1203, 1206, 1209: condenser
1204, 1207, 1210: reboiler
C1, C2, C3, C4, C5, C6, C7, C8, C9, C10, C11, C12, C13, C14, C15, C16, C17, C18: line
(in FIG. 13)
1301, 1304, 1307: continuous multistage distillation column
1302, 1305, 1308: condenser
1303, 1306, 1309: reboiler
D1, D2, D3, D4, D5, D6, D7, D8, D9, D10, D11, D12, D13, D14, D15: line
(in FIG. 14)
1401, 1402, 1403, 1409, 1411: storage tank
1404: baffled reaction vessel
1405, 1406: continuous multistage distillation column
1407, 1410: condenser
1408, 1412: reboiler
E1, E2, E3, E4, E5, E6, E7, E8, E9, E10, E11, E12, E13: line
(in FIG. 15)
1501, 1502, 1503: storage tank
1504: baffled reaction vessel
1506, 1509, 1512: continuous multistage distillation column
1505, 1508, 1511: condenser
1507, 1510, 1513: reboiler
F1, F2, F3, F4, F5, F6, F7, F8, F9, F10, F11, F12, F13, F14, F15, F16, F17, F18: line
(in FIG. 16)
1601, 1602, 1603, 1606: storage tank
1604: baffled reaction vessel
1605: column
1607: condenser
G1, G2, G3, G4, G5, G6: line

BEST MODE FOR CARRYING OUT THE INVENTION

The following provides a detailed explanation of the best mode for carrying out the present invention (hereinafter referred to as "present embodiment"). Furthermore, the present invention is not limited to the following present embodiment, but rather can be modified in various ways within the scope of the gist thereof.

The production process in the present embodiment is a process for producing an isocyanate, which comprises the steps of: obtaining a reaction mixture containing an aryl carbamate having an aryl group originating from a diaryl carbonate, an aromatic hydroxy compound originating from the diaryl carbonate, and the diaryl carbonate, by reacting the diaryl carbonate and an amine compound in the presence of an aromatic hydroxy compound as a reaction solvent, transferring the reaction mixture to a thermal decomposition reaction vessel, and obtaining an isocyanate by applying the aryl carbamate to a thermal decomposition reaction; wherein the reaction vessel in which the reaction between the diaryl carbonate and the amine compound is carried out, and the aryl carbamate thermal decomposition reaction vessel, are different.

An explanation is first provided of the diaryl carbonate and the amine compound used in the production process according to the present embodiment.

The diaryl carbonate used in the production process according to the present embodiment is a compound represented by the following formula (13):

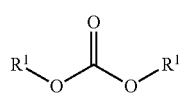

(13)

(wherein $R^1$ represents an aromatic group having 6 to 20 carbon atoms).

$R^1$ of formula (13) above is preferably an aromatic hydrocarbon group having 6 to 20 carbon atoms, and more preferably an aromatic hydrocarbon group having 6 to 12 carbon atoms. Although a diaryl carbonate can be used in which $R^1$ is an aromatic hydrocarbon group having 21 or more carbon atoms, from the viewpoint of facilitating separation of isocyanate formed by the thermal decomposition reaction of carbamic acid ester to be described later, the number of carbon atoms constituting $R^1$ is preferably 20 or less.

Specific examples of this $R^1$ may include a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a dimethylphenyl group (including isomers), a methylethylphenyl group (including isomers), a methylpropylphenyl group (including isomers), a methylbutylphenyl group (including isomers), a methylpentylphenyl group (including isomers), a diethylphenyl group (including isomers), an ethylpropylphenyl group (including isomers), an ethylbutylphenyl group (including isomers), a dipropylphenyl group (including isomers), a trimethylphenyl group (including isomers), a triethylphenyl group (including isomers) and a naphthyl group (including isomers). Among these diaryl carbonates, diaryl carbonates in which $R^1$ is an aromatic hydrocarbon group having 6 to 8 carbon atoms are preferable, and examples of such diaryl carbonates may include diphenyl carbonate, di(methylphenyl) carbonate (including isomers), di(diethylphenyl) carbonate (including isomers) and di(methylethylphenyl) carbonate (including isomers).

These diaryl carbonates contain metal atoms preferably within a range of from 0.001 ppm to 10%, more preferably within a range of from 0.001 ppm to 5%, and even more preferably within a range of from 0.002 ppm to 3%. In addition, the metal atoms may be present in the form of metal ions or in the form of individual metal atoms. The metal atoms are preferably metal atoms capable of having a valence of from 2 to 4, and one type or a plurality of types of metals selected from the group consisting of iron, cobalt, nickel, zinc, tin, copper and titanium are preferable. The inventors of the present invention unexpectedly found that when the diaryl carbonate containing metal atoms at a concentration within the above range is used, an effect is demonstrated that inhibits a denaturation reaction of the aryl carbamate formed in the reaction between the diaryl carbonate and the amine compound. Although the mechanism by which this effect is demonstrated is not clear, the inventors of the present invention presumed that these metal atoms coordinate to urethane bonds (—NHCOO—) of carbamic acid ester formed in the reaction, thereby stabilizing the urethane bonds and inhibiting side reactions as indicated in formulas (4) and (8) above, for example. In addition, although the effect of these metal atoms of inhibiting denaturation reactions of aryl carbamates has also been observed in the transport of reaction solutions containing aryl carbamates as will be described later, this mechanism is presumed to be the same as that described above.

Although similar effects are expected to be obtained even if a mixture is produced by mixing a diaryl carbonate and an amine compound and the previously indicated examples of metal atoms are added to the mixture within the above range, as a result of extensive studies conducted by the inventors of the present invention, it was determined that it is difficult to obtain the above effects simply by adding metal atoms to the mixture of the diaryl carbonate and the amine compound. Although the reason for obtaining such a result is not clear, the inventors of the present invention presumed that, in contrast to the diaryl carbonate coordinating to the metal atoms contained in the diaryl carbonate, since the interaction between the metal atoms and amine compound is greater than the interaction between the metal atoms and the diaryl carbonate, the metal atoms added to the mixture of the diaryl carbonate and amine compound strongly coordinate to the amine compound, thereby making it difficult to coordinate to the urethane bond of the formed aryl carbamate.

Although the carbamic acid ester in the present embodiment is preferably produced by the process described below, in the case the previously indicated examples of metal atoms are contained in a diaryl carbonate produced according to this process within the preferable range described above, that diaryl carbonate can be used as is. In the case the amount of the metal atoms contained in the diaryl carbonate is less than the previously described range, other metal atoms can be added in the form of an organic salt such as acetate or naphthenates, chloride or acetyl acetone complex. In addition, in the case the amount of the metal atoms is greater than the previously described range, the metal atoms can be used after reducing the amount of diaryl carbonate to within the previously described range by removing by, for example, cleaning with solvent, distillative purification, crystallization or using an ion exchange resin, or removing with a chelating resin.

Furthermore, since metal atoms contained within the above range in diaryl carbonates are not recognized to have catalytic action in reactions between diaryl carbonates and amine compounds in nearly all cases, in this sense, they are clearly distinguished from catalysts used for the production of aryl carbamates to be described later.

Since the amount of metal components contained in the diaryl carbonate can be quantified by various known methods, such as atomic absorption analysis, inductively coupled plasma-atomic emission spectrometry, inductively coupled plasma mass spectrometry, fluorescent X-ray analysis, X-ray photoelectron spectroscopy, electron beam microanalysis or secondary ion mass spectrometry, the method can be selected in consideration of the form of the sample and the amount of metal components contained therein.

Although a known process can be used to produce the diaryl carbonate, a process is preferably used in which an organic tin compound having a tin-oxygen-carbon bond is reacted with carbon dioxide to produce carbonic acid ester followed by producing diaryl carbonate from the carbonic acid ester and an aromatic hydroxy compound. Namely, the carbonic acid ester can be produced according to a process comprising the steps of:

step (1): (dialkyl carbonate formation step) obtaining a reaction mixture containing a dialkyl carbonate by reacting an organic tin compound having a tin-oxygen-carbon bond and carbon dioxide, step (2): (dialkyl carbonate separation step) obtaining the dialkyl carbonate and a residue liquid by separating the reaction mixture; and step (3): (diary) carbonate production step) obtaining a diaryl carbonate by reacting the dialkyl carbonate separated in step (2) and an aromatic hydroxy compound A followed by recovering a by-product alcohol.

In addition, the following steps (4) and (5) can be carried out in addition to these steps (1) to (3), the steps (4) and (5) comprising the steps of:

step (4): (organic tin compound regeneration step) forming an organic tin compound having a tin-oxygen-carbon bond and water by reacting the residue liquid obtained in step (2) with an alcohol followed by removing the water from the reaction system; and step (5): (recycling step) reusing the organic tin compound having the tin-oxygen-carbon bond obtained in step (4) as the organic tin compound having the tin-oxygen-carbon bond of step (1).

The dialkyl tin compounds are preferably used for the organic tin compound used in step (1). The dialkyl tin compound refers to an organic tin compound in which two alkyl groups are bonded to a single tin atom.

Examples of these dialkyl tin compounds may include compounds selected from at least one type of compound selected from the group consisting of dialkyl tin compounds represented by the following formula (14) and tetraalkyl distannoxane compounds represented by the following formula (15):

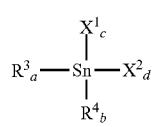

(14)

(wherein each of $R^3$ and $R^4$ independently represents a linear or branched alkyl group having 1 to 12 carbon atoms, each of $X^1$ and $X^2$ independently represents at least one type of substituent selected from the group consisting of an alkoxy group, an acyloxyl group and a halogen atom, each of a and b represents an integer of from 0 to 2, and a+b=2, and each of c and d represents an integer of from 0 to 2, and c+d=2);

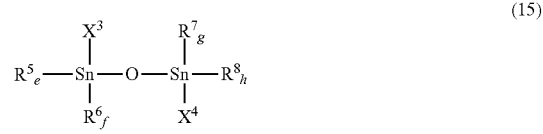

(15)

(wherein each of $R^5$, $R^6$, $R^7$ and $R^8$ independently represents a linear or branched alkyl group having 1 to 12 carbon atoms, $X^3$ and $X^4$ represent at least one type of substituent selected from the group consisting of an alkoxy group, an acyloxyl group and a halogen atom, and each of e, f, g and h represents an integer of from 0 to 2, e+f=2 and g+h=2).

Examples of $R^3$ and $R^4$ in the dialkyl tin catalyst represented by formula (14) above as well as examples of $R^5$, $R^6$, $R^7$ and $R^8$ in the tetraalkyl distannoxane compound represented by formula (15) above may include alkyl groups in the form of aliphatic hydrocarbon groups in which the number of carbon atoms constituting the group is a number selected from the group consisting of integers of 1 to 12, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers) or a dodecyl group (including isomers). More preferable examples may include linear or branched alkyl groups in which the number of carbon atoms constituting the group is a number selected from the group consisting of integers of from 1 to 8, and although dialkyl tin compounds can be used which have an alkyl group in which the number of carbon atoms constituting the group is outside the range indicated above, there are cases in which fluidity may be poor or productivity may be impaired. Moreover, a n-butyl group or a n-octyl group is more preferable in consideration of ease of acquisition during industrial production.

$X^1$ and $X^2$ of the dialkyl tin compound represented by formula (14) above and $X^3$ and $X^4$ of the tetraalkyl distannoxane compound represented by formula (15) above represent at least one type of substituent selected from the group consisting of an alkoxy group, an acyloxyl group and a halogen atom, and in the case the group is an alkoxy group and/or an acyloxy group, the number of carbon atoms constituting the group is preferably a number selected from the group consisting of integers of from 0 to 12. Examples of such groups may include alkoxy groups composed of a linear or branched saturated alkyl group and an oxygen atom, such as a methoxy group, an ethoxy group, a propoxy group (including isomers), a butoxy group (including isomers), a pentyloxy group (including isomers), a hexyloxy group (including isomers), a heptyloxy group (including isomers), an octyloxy group (including isomers), a nonyloxy group (including isomers) or a decyloxy group (including isomers); acyloxyl groups composed of a linear or branched saturated alkyl group, a carbonyl group and oxygen atom, such as an acetoxy group, a propionyloxy group, a butyryloxy group, a valeryloxy group or a lauroyloxy group; and a halogen atom such as a chloro group or bromo group. More preferable examples may include alkoxy groups having 4 to 6 carbon atoms in consideration of fluidity and solubility as well as use as a carbonic acid ester production catalyst.

Examples of dialkyl tin compounds represented by formula (14) may include dialkyl-dialkoxy tins such as dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dimethyl-dinonyloxy tin (including isomers), dimethyl-didecyloxy tin (including isomers), dibutyl-dimethoxy tin (including isomers), dibutyl-diethoxy tin (including isomers), dibutyl-dipropoxy tin (including isomers), dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dibutyl-dinonyloxy tin (including isomers), dibutyl-didecyloxy tin (including isomers), dioctyl-dimethoxy tin (including isomers), dioctyl-diethoxy tin (including isomers), dioctyl-dipropoxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers), dioctyl-dinonyloxy tin (including isomers) or dioctyl-didecyloxy tin (including isomers); dialkyl-diacyloxy tins such as dimethyl-diacetoxy tin, dimethyl-dipropionyloxy tin (including isomers), dimethyl-dibutyryloxy tin (including isomers), dimethyl-valeryloxy tin (including isomers), dimethyl-dilauroyloxy tin (including isomers), dibutyl-diacetoxy tin (including isomers), dibutyl-dipropionyloxy tin (including isomers), dibutyl-dibutyryloxy tin (including isomers), dibutyl-divaleryloxy tin (including isomers), dibutyl-dilauroyloxy tin (including isomers), dioctyl-diacetoxy tin (including isomers), dioctyl-dipropionyloxy tin (including isomers), dioctyl-dibutyryloxy tin (including isomers), dioctyl-valeryloxy tin (including isomers) or dioctyl-dilauroyloxy tin (including isomers); and dialkyl-dihalide tins such as dimethyl-dichloro tin, dimethyl-dibromo tin, dibutyl-dichloro tin (including isomers), dibutyl-dibromo tin (including isomers), dioctyl-dichloro tin (including isomers) or dioctyl-dibromo tin (including isomers).

Among these, dialkyl tin dialkoxides such as dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dimethyl-dinonyloxy tin (including isomers), dimethyl-didecyloxy tin (including isomers), dibutyl-dimethoxy tin (including isomers), dibutyl-diethoxy tin (including isomers), dibutyl-dipropoxy tin (including isomers), dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dibutyl-dinonyloxy tin (including isomers), dibutyl-didecyloxy tin (including isomers), dioctyl-dimethoxy tin (including isomers), dioctyl-diethoxy tin (including isomers), dioctyl-dipropoxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers), dioctyl-dinonyloxy tin (including isomers) or dioctyl-didecyloxy tin (including isomers) are preferable, dialkyl-dialkoxy tins such as dibutyl-dipropoxy tin (including isomers), dibutyl-dibutyryloxy tin (including isomers), dibutyl-dipentyloxy tin (including isomers), dibutyl-dihexyloxy tin (including isomers), dibutyl-diheptyloxy tin (including isomers), dioctyl-dipropoxy tin (including isomers), dioctyl-dibutoxy tin (including isomers), dioctyl-dipentyloxy tin (including isomers), dioctyl-dihexyloxy tin (including isomers) or dioctyl-diheptyloxy tin (including isomers) are more preferable, and dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers) or dioctyl-dioctyloxy tin (including isomers) is even more preferable.

Although the dialkyl tin compounds represented by the formula (14) show a monomer structure, this may be a polymer structure or an associate.

Examples of the tetraalkyl dialkoxy distannoxane represented by the formula (15) may include 1,1,3,3-tetraalkyl-1,3-dialkoxy distannoxanes such as 1,1,3,3-tetramethyl-1,3-dimethoxy distannoxane, 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetramethyl-1,3-dinonyloxy distannoxane (including isomers), 1,1,3,3-tetramethyl-1,3-didecyloxydistannoxane (including isomers), 1,1,3,3-tetrabutyl-1,3-dimethoxy distannoxane (including isomers), 1,1,3,3-tetrabutyl-1,3-diethoxy distannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetrabutyl-1,3-dinonyloxy distannoxane (including isomers), 1,1,3,3-tetrabutyl-1,3-didecyloxy distannoxane (including isomers), 1,1,3,3-tetraoctyl-1,3-dimethoxy distannoxane (including isomers), 1,1,3,3-tetraocyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers), 1,1,3,3-tetraoctyl-1,3-dioctyloxy distannoxane (including isomers), 1,1,3,3-tetraoctyl-1,3-dinonyloxy distannoxane (including isomers) or 1,1,3,3-tetraoctyl-1,3-didecyloxy distannoxane (including isomers); 1,1,3,3-tetraalkyl-1,3-diacyloxy distannoxanes such as 1,1,3,3-tetramethyl-1,3-diacetoxy distannoxane, 1,1,3,3-tetramethyl-1,3-dipropionyloxy distannoxane (including isomers), 1,1,3,3-tetramethyl-1,3-dibutyryloxy distannoxane (including isomers), 1,1,3,3-tetramethyl-1,3-divaleryloxy distannoxane (including isomers), 1,1,3,3-tetramethyl-1,3-dilauroyloxy distannoxane (including isomers), 1,1,3,3-tetrabutyl-1,3-diacetoxy distannoxane (including isomers), 1,1,3,3-tetrabutyl-1,3-dipropionyloxy distannoxane (including isomers), 1,1,3,3-tetrabutyl-1,3-dibutyryloxy distannoxane (including isomers), 1,1,3,3- tetrabutyl-1,3-divaleryloxy distannoxane (including isomers), 1,1,3,3-tetrabutyl-1,3-dilauroyloxy distannoxane (including isomers), 1,1,3,3-tetraoctyl-1,3-diacetoxy distannoxane (including isomers), 1,1,3,3-tetraoctyl-1,3-dipropionyloxy distannoxane (including isomers), 1,1,3,3-tetraoctyl-1,3-dibutyryloxy distannoxane (including isomers), 1,1,3,3-tetraoctyl-1,3-divaleryloxy distannoxane (including isomers) or 1,1,3,3-tetraoctyl-1,3-dilauroyloxy distannoxane (including isomers); and, 1,1,3,3-tetraalkyl-1,3-dihalide distannoxanes such as 1,1,3,3-tetramethyl-1,3-dichlorodistannoxane, 1,1,3,3-tetramethyl-1,3-dibromodistannoxane, 1,1,3,3-tetrabutyl-1,3-dichlorodistannoxane (including isomers), 1,1,3,3-tetrabutyl-1,3-dibromodistannoxane (including isomers), 1,1,3,3-tetraocyl-1,3-dichlorodistannoxane (including isomers) or 1,1,3,3-tetraocyl-1,3-dibromodistannoxane (including isomers).

Among these, 1,1,3,3-tetraalkyl-1,3-dialkoxy distannoxanes such as 1,1,3,3-tetramethyl-1,3-dimethoxy distannoxane, 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetramethyl-1,3-dinonyloxy distannoxane (including isomers), 1,1,3,3-tetramethyl-1,3-didecyloxy distannoxane (including isomers), 1,1,3,3-tetrabutyl-1,3-dimethoxy distannoxane (including isomers), 1,1,3,3-tetrabutyl-1,3-diethoxy distannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetrabutyl-1,3-dinonyloxy distannoxane (including isomers), 1,1,3,3-tetrabutyl-1,3-didecyloxy distannoxane (including isomers), 1,1,3,3-tetraoctyl-1,3-dimethoxy distannoxane (including isomers), 1,1,3,3-tetraocyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers), 1,1,3,3-tetraoctyl-1,3-dioctyloxy distannoxane (including isomers), 1,1,3,3-tetraoctyl-1,3-dinonyloxy distannoxane (including isomers) or 1,1,3,3-tetraoctyl-1,3-didecyloxy distannoxane (including isomers) are preferable, and 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers) or 1,1,3,3-tetraoctyl-1,3-dioctyloxy distannoxane (including isomers) is more preferable.

Although the tetraalkyl dialkoxy distannoxane represented by formula (15) shows a monomer structure, this may also be a polymer structure or an associate.

In general, organic tin compounds easily adopt an associated structure, and although, for example, dialkyl tin dialkoxy tin is known to form a dimer structure, and tetraalkyl dialkoxy distannoxanes are known to be present by forming a ladder structure in which two or three molecules are associated, even in cases in which there are changes in this associated state, the representation of a compound in the form of a monomer structure is common for a person with ordinary skill in the art.

In addition, the previously indicated dialkyl tin compound may be used alone or two or more types may be used as a mixture.

A previously disclosed production process (such as that disclosed in WO 2005/111049) can preferably be used as the process for producing the dialkyl tin compound. This process is a process for producing the dialkyl tin compounds from the dialkyl tin oxides and alcohols.

Examples of alcohols used in the present embodiment may include alcohols such as methanol, ethanol, propanol (including isomers), butanol (including isomers), pentanol (including isomers), hexanol (including isomers), heptanol (including isomers), octanol (including isomers), nonanol (including isomers) or decanol (including isomers), and an alcohol is preferably used in which the number of carbon atoms constituting the alcohol is a number selected from the group consisting of integers of from 1 to 12.

The dialkyl tin oxides represented by the following formula (16) are used for the dialkyl tin oxide used in the alkyl tin alkoxide synthesis process:

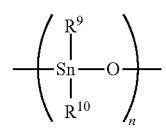

(16)

(wherein each of $R^9$ and $R^{19}$ independently represents a linear or branched alkyl group having 1 to 12 carbon atoms).

Examples of $R^9$ and $R^{19}$ may include alkyl groups in the form of aliphatic hydrocarbon groups having 1 to 12 carbon atoms, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers) or a dodecyl group (including isomers). More preferable examples may include linear or branched saturated alkyl groups having 1 to 8 carbon atoms, while even more preferable examples may include a n-butyl group and a n-octyl group.

The tetraalkyl dialkoxy distannoxanes and/or the dialkyl tin dialkoxides are obtained by dehydration reaction of the alcohol and the dialkyl tin oxide while removing the water formed from the system. The temperature at which the reaction is carried out is, for example, within a range of from 80 to 180° C., and in order to distill off the water formed from the system, although varying according to the reaction pressure, a temperature of from 100 to 180° C. is preferable. Although a high temperature is preferable for the reaction temperature to accelerate the reaction rate, since undesirable reactions such as decomposition may also occur at high temperatures thereby decreasing yield, the reaction temperature is more preferably within a range of from 100 to 160° C. The reaction pressure is a pressure that allows water formed to be removed from the system, and the reaction is carried out at a pressure of from 20 to $1 \times 10^6$ Pa, although varying according to the reaction temperature. There are no particular limitations on the reaction time of the dehydration reaction, and is generally from 0.001 to 50 hours, preferably from 0.01 to 10 hours and more preferably from 0.1 to 2 hours. The reaction may be terminated once the desired alkyl tin alkoxide composition has been obtained. Progression of the reaction is also determined by measuring the amount of water extracted outside the system, and can also be determined by a method using $^{119}$Sn-NMR by sampling the reaction liquid. In order to produce the mixture according to the present embodiment in step (1), the reaction is terminated after confirming the obtaining of a composition in which the molar ratio of tetraalkyl dialkoxy distannoxane and dialkyl tin dialkoxide contained in the alkyl tin alkoxide composition obtained in the above reaction, when expressed as the combined molar percentage of both, is within a range of from 0:100 to 80:20 and more preferably within a range of from 10:90 to 70:30. The alcohol used may be used while still present in the reaction system, and the alcohol may also be used by distilling off the alcohol depending on the case. Since there is the advantage of being able to reduce the size of the reaction vessels of the other steps, it is preferable to remove as much of the alcohol as possible. Removal by known distillation is preferable for the removal method, and known distillation equipment can be used for the distiller used for distillation. A thin film distillation apparatus is preferably used for the distillation apparatus since the alcohol can be removed in a short period of time. There are no particular limitations on the type of reaction vessel of the dehydration reaction, and a known tank type or column type reaction vessel can be used. A low boiling point reaction mixture containing water is extracted in gaseous form from the reaction vessel by distillation, while a high boiling point reaction mixture containing a produced alkyl tin alkoxide or alkyl tin alkoxide mixture is extracted in the form of a liquid from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a columnar reactor are preferable from the viewpoint of efficiently shifting the equilibrium to the products side, while a structure having a large gas-liquid contact area is preferable for being able to rapidly transfer the water formed to the gaseous phase. Although continuous methods using a multitubular reactor, a multistage distillation column or a packed column packed with a packing can also be used, since the dialkyl tin oxide used in this step is generally a solid, it is preferable to employ a method in which the reaction is first carried out in a tank-type reaction vessel followed by increasing the content of dialkyl tin dialkoxide in a column-type reaction vessel. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Step (1) is a step for producing carbonic acid esters by reacting the dialkyl tin compounds produced according to the process described above with gaseous carbon dioxide. A previously disclosed carbonic acid ester production process (such as that disclosed in WO 03/055840 or WO 04/014840) is preferably used in this step.

The alkyl tin compounds supplied to this step may be supplied from an alkyl tin alkoxide synthesis step at the start of production, or from a dialkyl tin compound production step of step (4) to be described later through step (5) during continuous production.

In step (1), the above-mentioned dialkyl tin alkoxide and gaseous carbon dioxide are absorbed and undergo a chemical reaction to obtain a mixture containing a carbon dioxide-bonded form of the dialkyl tin alkoxide. During this chemical reaction, the dialkyl tin alkoxide is reacted in a liquid form. The dialkyl tin alkoxide is preferably put into a liquid form by heating to obtain the dialkyl tin alkoxide in a liquid form in the case the dialkyl tin alkoxide is in a solid form. In addition, it may also be put into a liquid form by a solvent and the like. Although varying according to the reaction temperature, the reaction pressure is preferably within a range of from a normal pressure to 1 MPa, and more preferably within a range of from a normal pressure to 0.6 MPa. Although varying according to the reaction pressure, the reaction temperature is preferably within a range of from −40 to 80° C., and in consideration of fluidity during transfer, more preferably from 0 to 80° C. and most preferably within a range of from normal temperature (e.g., 20° C.) to 80° C. The reaction time may be within a range of from several seconds to 100 hours, and in consideration of productivity and the like, is preferably from several minutes to 10 hours. A known tank type reaction vessel or column type reaction vessel can be used for the reaction vessel. In addition, a plurality of reaction vessels may be used in combination. Since the reaction is a reaction between carbon dioxide gas (gas) and the alkyl tin alkoxide composition (liquid), in order to carry out the reaction efficiently, it is preferable to increase the contact surface area between the gas and liquid by increasing the gas-liquid interface. Known findings can be used for the method for reacting while increasing the gas-liquid interface in this manner, and examples of preferable methods thereof may include increasing the stirring speed or generating bubbles in the liquid in the case of a tank type reaction vessel, and using a packed column or using a plate column in the case of a column type reaction vessel. Examples of such column type reaction vessels may include plate column types using a tray such as a bubble tray, a porous plate tray, a valve tray or a counter-current tray, and packed column types packed with various types of packing materials such as a raschig ring, a lessing ring, a pole ring, a Berl saddle, an Interlock saddle, a Dixon packing, a McMahon packing, a Helipack, a Sulzer packing or Mellapak. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Since the reaction is generally an exothermic reaction, the reaction vessel may be cooled or it may be cooled by dissipation of heat therefrom. Alternatively, the reaction vessel may also be heated if the purpose is combining with a carbonic acid esterification reaction. A known method such as a method using a heat jacket or a method using an internal coil can be used to heat and cool the reaction vessel. The carbon dioxide gas and alkyl tin alkoxide composition supplied to the reaction vessel may be supplied separately to the reaction vessel or they may be mixed prior to supplying to the reaction vessel. These components may also be supplied from a plurality of locations in the reaction vessel. Completion of the reaction can be determined by, for example, $^{119}$Sn-NMR analysis.

Next, a reaction liquid containing carbonic acid ester is obtained from the carbon dioxide-bonded form of the dialkyl tin alkoxide obtained in the above manner according to the method described below.

Although the reaction temperature is within a range of from 110 to 200° C., and a high temperature is preferable for the reaction temperature in order to accelerate the reaction rate, since undesirable reactions such as decomposition also occur at high temperatures thereby decreasing yield, the reaction temperature is more preferably within a range of from 120 to 180° C., the reaction time is preferably within a range of from 0.1 to 10 hours, and the reaction pressure is within a range of from 1.5 to 20 MPa and preferably from 2.0 to 10 MPa. The reaction is terminated after the desired carbonic acid ester has formed in the reaction vessel. Progression of the reaction can be confirmed by, for example, sampling the reaction liquid in the reaction vessel, and analyzing the carbonic acid ester formed by a method such as $^{1}$H-NMR or gas chromatography. For example, the reaction may be terminated after the carbonic acid ester has been formed at a molar ratio of 10% or more of the dialkyl tin alkoxide and/or carbon dioxide-bonded form of the dialkyl tin alkoxide contained in the dialkyl tin alkoxide and/or carbon dioxide-bonded form of the dialkyl tin alkoxide, and in the case of desiring to increase the yield of the carbonic acid ester, the reaction may be terminated after allowing to continue until the value reaches 90% or more. A known reaction vessel can be used for the reaction vessel, and a column type reaction vessel or tank type reaction vessel can be used preferably. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Step (2) in the present embodiment is a step for obtaining the residue liquid from the reaction liquid containing carbonic acid ester obtained in step (1) above together with separating and recovering the carbonic acid ester. A known method or apparatus can be preferably used for the separation method, and a preferable method is distillation.

Carbonic acid ester and the residue liquid are obtained by batch, semi-batch or continuous distillation of the reaction liquid transferred from step (1) above. A preferable example of a distillation method consists of supplying the reaction liquid to a distiller, separating the carbonic acid ester in the form of a gaseous phase component from a top of the distiller outside the system, and extracting the residue liquid in the form of a liquid component from a bottom of the distiller. Although varying according to the boiling point of the carbonic acid ester and pressure, the temperature in this step is within a range of from normal temperature (e.g., 20° C.) to 200° C., and since there are cases in which denaturation of tin compounds in the residue liquid may occur or the amount of carbonic acid ester may decrease due to a reverse reaction at high temperatures, the temperature is preferably within a range of from normal temperature (e.g. 20° C.) to 150° C. Although varying according to the type of carbonic acid ester and temperature at which the reaction is carried out, the reaction is generally carried out at from normal pressure to reduced pressure conditions, and in consideration of productivity, the pressure is more preferably within a range of from 100 Pa to 80 KPa and most preferably within a range of from 100 Pa to 50 KPa. The reaction can be carried out a reaction time within a range of from 0.01 to 10 hours, and since there are cases in which tin compounds contained in the reaction liquid are denatured and cases in which the amount of carbonic acid ester decreases due to a reverse reaction when the reaction is carried out for a long period of time at high temperatures, the reaction time is preferably within a range of from 0.01 to 0.5 hours and most preferably within a range of from 0.01 to 0.3 hours. A known distiller can be used for the distiller, a column type distiller or a tank type distiller can be used preferably, or a plurality of types can be used in combination. More preferable distillers consist of a thin film evaporator and a thin film distiller, and a thin film evaporator provided with a distillation column or a thin film distiller is most preferable. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Step (3) is a step for obtaining the diaryl carbonate by reacting the dialkyl carbonate separated in step (2) and an aromatic hydroxy compound A followed by recovering a by-product alcohol. The aromatic hydroxy compound as mentioned herein refers to a compound corresponding to a compound $R^1OH$ in which a hydrogen atom is added to a group $R^1O$ constituting the diaryl carbonate represented by formula (1) above (wherein $R^1$ represents an aromatic group as previously defined, and O represents an oxygen atom). Specific examples of preferably used aromatic hydroxy compound A may include phenol, mono-substituted phenols such as methylphenol (including isomers), ethylphenol (including isomers), propylphenol (including isomers), butylphenol (including isomers), pentylphenol (including isomers) or hexylphenol (including isomers); di-substituted phenols such as dimethylphenol (including isomers), diethylphenol (including isomers), dipropylphenol (including isomers), methylethylphenol (including isomers), methylpropylphenol (including isomers), methylbutylphenol (including isomers), methylpentylphenol (including isomers), ethylpropylphenol (including isomers) or ethylbutylphenol (including isomers); tri-substituted phenols such as trimethylphenol (including isomers), triethylphenol (including isomers), dimethylethylphenol (including isomers), dimethylpropylphenol (including isomers) or dimethylbutylphenol (including isomers); and naphthol (including isomers).

Step (3) in the present embodiment is a step for obtaining diaryl carbonate by reacting a component mainly containing carbonic acid ester separated in step (2) and the aromatic hydroxy compound A. Numerous processes for obtaining alkyl aryl carbonates and diaryl carbonates from dialkyl carbonates and aromatic hydroxy compounds have been previously proposed, and these technologies can be preferably applied in the present embodiment as well.

The reaction of step (3) comprises a transesterification reaction between the carbonic acid esters and the aromatic hydroxy compounds, and a disproportionation reaction of the alkyl aryl carbonate obtained in the transesterification reaction.

The transesterification reaction is an equilibrium reaction and in order to allow the reaction to proceed advantageously, it is preferable to carry out the reaction while extracting the alcohol formed by elimination in the transesterification reaction, and in this case, the boiling point of the aromatic hydroxy compound used in step (3) is preferably higher than the boiling point of the alkyl alcohol constituting the alkyl carbonate obtained in step (2). In particular, in the case of carrying out steps (1) to (3) continuously by repeating one or more times, the boiling point of the alkyl alcohol is preferably lower than the standard boiling point of the aromatic hydroxy compound, and the difference between the boiling points thereof is preferably 2° C. and more preferably 10° C. in consideration of ease of separation.

Examples of dialkyl carbonates used in step (3) may include dimethyl carbonate, diethyl carbonate, dipropyl carbonate (including isomers), dibutyl carbonate (including isomers), dipentyl carbonate (including isomers), dihexyl carbonate (including isomers), diheptyl carbonate (including isomers), dioctyl carbonate (including isomers), dinonyl carbonate (including isomers), didecyl carbonate (including isomers), dicyclopentyl carbonate (including isomers), dicyclohexyl carbonate (including isomers), dicycloheptyl carbonate (including isomers), dibenzyl carbonate, diphenethyl carbonate (including isomers), di(phenylpropyl) carbonate (including isomers), di(phenylbutyl) carbonate (including isomers), di(chlorobenzyl) carbonate (including isomers), di(methoxybenzyl) carbonate (including isomers), di(methoxymethyl) carbonate (including isomers), di(methoxyethyl) carbonate (including isomers), di(chloroethyl) carbonate (including isomers), di(cyanoethyl) carbonate (including isomers), methylethyl carbonate, methylpropyl carbonate (including isomers), methylbutyl carbonate (including isomers), ethylpropyl carbonate (including isomers), ethylbutyl carbonate (including isomers), ethylene carbonate and propylene carbonate. The carbonic acid ester used may be one type or a mixture thereof.

Among these dialkyl carbonates, those dialkyl carbonates that are used preferably in the present embodiment are diaryl carbonate in which the standard boiling point of the alcohol constituting the carbonic acid ester is higher than the standard boiling point of water, for example, alkyl alcohols having an alkyl group having 4 to 12 carbon atoms, alkenyl alcohols having a linear or branched alkenyl group having 4 to 12 carbon atoms, cycloalkyl alcohols and aralkyl alcohols. In order to allow the reaction carried out in step (3) to proceed advantageously, an alcohol having a standard boiling point lower than the standard boiling point of the aromatic hydroxy compound used in step (3) is more preferable in consideration of removing the alcohol formed in the reaction of step (3). Namely, a dialkyl carbonate is preferable that is composed of an alcohol having a standard boiling point higher than the standard boiling point of water but lower than the standard boiling point of the aromatic hydroxy compound.

The amount of the aromatic hydroxy compound used in step (3) is separated in step (2) and can be used within a range of a stoichiometric ratio of from 0.1 to 10000 times the amount of dialkyl carbonate used in step (3). Since the reaction of step (3) is mainly an equilibrium reaction, although a large amount of the aromatic hydroxy compound is advantageous, since an increase in the amount used results in a larger reaction vessel as well as a large distillation column for subsequently separating the product, the amount of the aromatic hydroxy compound is preferably within a range of from 1 to 1000 times and more preferably within a range of from 1 to 100 times the amount of the dialkyl carbonate.

Although the compounds supplied to step (3) mainly consist of dialkyl carbonate, aromatic hydroxy compound and, as necessary, a catalyst, impurities may be present provided they do not have a particularly detrimental effect on the reaction. Although products in the form of alcohol, alkyl aryl carbonate and diaryl carbonate and the like may be contained among these supplied raw materials, since the reaction is reversible, the reaction rate of the raw materials decreases in the case the concentrations of these products are excessively high, thereby making this undesirable. Although able to be varied according to the type and amount of catalyst and the reaction conditions, the weight ratio of the supplied dialkyl carbonate and aromatic hydroxy compound is generally such that the aromatic hydroxy compound is preferably supplied at a molar ratio within a range of from 0.01 to 1000 times the dialkyl carbonate in the supplied raw materials.

Although varying according to the reaction conditions and type and internal structure of the reaction vessel, the reaction time of the transesterification reaction of step (3) is generally from 0.001 to 50 hours, preferably from 0.01 to 10 hours and more preferably from 0.05 to 5 hours. The reaction temperature refers to the temperature within the reaction vessel, and although varying according to the types of raw materials used in the form of the dialkyl carbonate and the aromatic hydroxy compound, is generally within a range of from 50 to 350° C. and preferably from 100 to 280° C. In addition, although varying according to the types of raw material compounds used, the reaction temperature and the like, the reaction pressure may be decreased pressure, normal pressure or increased pressure, and the reaction is generally carried out within a range of from 10 Pa to 20 MPa.

Although the use of a solvent is not necessarily required in the present embodiment, a suitable inert solvent can be used as a reaction solvent for the purpose of, for example, facilitating the reaction procedure, examples of which may include ethers, aliphatic hydrocarbons, aromatic hydrocarbons, aliphatic hydrocarbon halides and aromatic hydrocarbon halides. In addition, an inert gas such as nitrogen, helium or argon may also be present in the reaction system as an inert substance in the reaction, and the above inert gases and low boiling point organic compounds inactive in the reaction may be introduced in gaseous form from the lower portion of a continuous multistage distillation column for the purpose of accelerating the removal of low boiling point by-products formed by distillation.

A catalyst may be added when carrying out the transesterification reaction of step (3). Although alkyl aryl carbonate and diaryl carbonate are obtained from carbonic acid ester by transesterification as previously described, since the equilibrium of this transesterification reaction is biased towards the reactants and since the reaction rate is slow, when producing diaryl carbonate by this process, several proposals have been made to improve these, and a known process can be preferably used in the present embodiment.

Although varying according to the type of catalyst used, the type of reaction vessel, the types and weight ratio of the carbonic acid ester and aromatic hydroxy compound and reaction conditions such as the reaction temperature and reaction pressure, the amount of catalyst in the case of using a catalyst in the present embodiment is generally from 0.0001 to 50% by weight when expressed as the ratio to the total amount of the carbonic acid ester and aromatic hydroxy compound as the supplied raw materials. In addition, in the case of using a solid catalyst, the catalyst is preferably used at an amount of from 0.01 to 75% by volume based on the volume of the empty column of the reaction vessel.

Numerous metal-containing catalysts are known in proposals relating to catalysts for increasing reaction rate, and known transesterification reaction catalysts can be used in the present embodiment as well. In a process for producing alkyl aryl carbonate and/or a mixture of alkyl aryl carbonate and diaryl carbonate by reacting the carbonic acid ester and the aromatic hydroxy compound, Lewis acids such as transition metal hydrides or compounds that generate Lewis acids, tin compounds such as organic tin alkoxides or organic tin oxides, salts and alkoxides of alkaline earth metals or alkaline metals, lead compounds, metal complexes such as those of copper, iron or zirconium, titanic acid esters, mixtures of Lewis acids and protic acids, Sc, Mo, Mn, Bi or Te compounds, and ferric acetate have been proposed as examples of such catalysts. Although formation of diaryl carbonate can occur by a transesterification reaction only, it is also formed by a disproportionation reaction on the alkyl aryl carbonate formed in a transesterification reaction. Here, a disproportionation reaction refers to a reaction in which dialkyl carbonate and diaryl carbonate are formed from two molecules of alkyl aryl carbonate. Although the alkyl aryl carbonate further reacts with the aromatic hydroxy compound to become a diaryl carbonate, since the disproportionation reaction is faster, in the case of desiring to obtain the diaryl carbonate, the diaryl carbonate is obtained by disproportionating the alkyl aryl carbonate. Both of these reactions are equilibrium reactions. It is advantageous to allow the reaction to proceed while extracting alkyl alcohol in the transesterification reaction for producing alkyl aryl carbonate, and advantageous to allow the reaction to proceed while extracting dialkyl carbonate in the disproportionation step. Thus, the preferable reaction conditions differ in each stage. Although it is necessary to carry out the reaction by dividing into two stages in the case of carrying out the reaction continuously, in the case of carrying out the reaction in batches, the reaction can also be carried out sequentially within the same reaction vessel.

Thus, a catalyst that catalyzes the disproportionation reaction may also be present with the previously described transesterification catalyst. Numerous examples of such catalysts have been proposed, examples of which may include Lewis acids and transition metal compounds capable of generating Lewis acids, polymeric tin compounds, compounds represented by the general formula R—X(=O)OH (wherein X is selected from the group consisting of Sn and Ti, while R is selected from the group consisting of monovalent hydrocarbon groups), mixtures of Lewis acids and protic acids, lead catalysts, titanium and zirconium compounds, tin compounds and Sc, Mo, Mn, Bi or Te compounds.

The disproportionation step is a step in which dialkyl carbonate and diaryl carbonate are obtained by disproportionating the alkyl aryl carbonate obtained in the transesterification step. As was previously described, a disproportionation catalyst may be added when carrying out the transesterification reaction to carry out the transesterification reaction and disproportionation reaction simultaneously, or the transesterification reaction and disproportionation reaction may be carried out separately and consecutively or in batches. In addition, although there are cases in which diaryl carbonate is obtained simultaneously to alkyl aryl carbonate in the transesterification reaction as well in the case of carrying out the transesterification reaction and disproportionation reaction separately, in this case as well, the disproportionation reaction can be carried out as is. As was previously indicated, the disproportionation reaction is a step in which alkyl aryl carbonate is obtained by a transesterification reaction between the dialkyl carbonate and the aromatic hydroxy compound, and in order to allow this equilibrium reaction to proceed advantageously, it is advantageous to employ a method that allows the reaction to proceed while extracting alcohol. Since the disproportionation reaction is also subjected to the restriction of equilibrium, if attempting to allow the reaction to proceed advantageously, a method that allows the reaction to proceed while extracting either the dialkyl carbonate or diaryl carbonate formed in the disproportionation reaction outside the system is advantageous. In the present embodiment, it is preferable to carry out the disproportionation reaction while extracting the dialkyl carbonate outside the system by selecting the respective alkoxy groups and aryl groups so that the dialkyl carbonate of the products boils at a lower temperature than the diaryl carbonate. The extracted dialkyl carbonate may be used by returning to a step prior to the disproportionation reaction. If the amount of diaryl carbonate produced is to be increased, it is preferable to use the extracted dialkyl carbonate by returning to the transesterification step.

A catalyst of the disproportionation reaction may be used in the disproportionation reaction. Numerous examples of such catalysts have been proposed. Examples of such catalysts that have been proposed may include Lewis acids and transition metal compounds capable of generating Lewis acids, polymeric tin compounds, compounds represented by the general formula R—X(=O)OH (wherein X is selected from the group consisting of Sn and Ti, while R is selected from the group consisting of monovalent hydrocarbon groups), mixtures of Lewis acids and protic acids, lead catalysts, titanium and zirconium compounds, tin compounds and Sc, Mo, Mn, Bi or Te compounds.

The same catalysts as the transesterification catalysts used in the transesterification step can be used for the disproportionation reaction catalyst in the present embodiment.

The alkyl aryl carbonate used in the disproportionation step is an alkyl aryl carbonic acid ester. Examples of alkyl aryl carbonates may include methylphenyl carbonate, ethylphenyl carbonate, propylphenyl carbonate (including isomers), butylphenyl carbonate (including isomers), allylphenyl carbonate (including isomers), pentylphenyl carbonate (including isomers), hexylphenyl carbonate (including isomers), heptylphenyl carbonate (including isomers), octyltolyl carbonate (including isomers), nonyl (ethylphenyl) carbonate (including isomers), decyl (butylphenyl) carbonate (including isomers), methyltolyl carbonate (including isomers), ethyltolyl carbonate (including isomers), propyltolyl carbonate (including isomers), butyltolyl carbonate (including isomers), allyltolyl carbonate (including isomers), methylxylyl carbonate (including isomers), methyl (trimethylphenyl) carbonate (including isomers), methyl (chlorophenyl) carbonate (including isomers), methyl (nitrophenyl) carbonate (including isomers), methyl (methoxyphenyl) carbonate (including isomers), methyl (pyridyl) carbonate (including isomers), ethylcumyl carbonate (including isomers), methyl (benzoylphenyl) carbonate (including isomers), ethylxylyl carbonate (including isomers) and benzylxylyl carbonate (including isomers). These alkyl aryl carbonates may be of one type or a mixture of two or more types.

Among these alkyl aryl carbonates, those which are preferably used in the present embodiment are those in which the alcohol constituting the alkyl aryl carbonate is an alcohol having a boiling point higher than water, the boiling point of the alcohol constituting the alkyl aryl carbonate is lower than the boiling point of the aromatic hydroxy compound constituting the alkyl aryl carbonate, is selected from, for example, alkyl alcohols having a linear or branched alkyl group having 4 to 12 carbon atoms, alkenyl alcohols having a linear or branched alkenyl group having 4 to 12 carbon atoms, cycloalkyl alcohols and aralkyl alcohols, and when considering the removal of dialkyl carbonate formed in the disproportionation reaction, is preferably a dialkyl carbonate having a boiling point lower than the diaryl carbonate obtained in the disproportionation reaction to enable the disproportionation reaction to proceed advantageously. As examples of such optimum combinations, the alcohol, the alcohol corresponding to the alkoxy group of a metal compound having a metal-carbon-oxygen bond represented by the previously mentioned formulas (14) and (15), and the alcohol constituting the dialkyl carbonate are alcohols selected from the group consisting of pentanol (including isomers), hexanol (including isomers) and heptanol (including isomers), while the aromatic hydroxy compound is an aromatic hydroxy compound selected from phenol and cresol.

Although compounds supplied to the disproportionation reaction mainly consist of alkyl aryl carbonate and a catalyst as necessary, impurities may also be present provided they do not have a particularly detrimental effect on the reaction.

Although varying according to the type of catalyst used, the type of reaction vessel, the type and amount of the alkyl aryl carbonate and reaction conditions such as the reaction temperature and reaction pressure, the amount of catalyst in the case of using a catalyst in the present embodiment is generally from 0.0001 to 50% by weight when expressed as the ratio to the total amount of the alkyl aryl carbonate as the supplied raw material. In addition, in the case of using a solid catalyst, the catalyst is preferably used at an amount of from 0.01 to 75% by volume based on the volume of the empty column of the reaction vessel.

Although alcohol, aromatic hydroxy compound and diaryl carbonate and the like may be contained among these supplied raw materials, since the reaction is reversible, the reaction rate of the raw materials decreases in the case the concentrations of these components are excessively high, thereby making this undesirable.

Although varying according to the reaction conditions and type and internal structure of the reaction vessel, the reaction time of the disproportionation reaction is generally from 0.001 to 50 hours, preferably from 0.01 to 10 hours and more preferably from 0.05 to 5 hours. Although varying according to the type of alkyl aryl carbonate used, the reaction temperature is generally within a range of from 50 to 350° C. and preferably from 100 to 280° C. In addition, although varying according to the types of raw material compounds used, the reaction temperature and the like, the reaction pressure may be decreased pressure, normal pressure or increased pressure, and the reaction is generally carried out within a range of from 10 Pa to 20 MPa.

Although the use of a solvent is not necessarily required in the disproportionation step of the present embodiment, a suitable inert solvent can be used as a reaction solvent for the purpose of, for example, facilitating the reaction procedure, examples of which may include ethers, aliphatic hydrocarbons, aromatic hydrocarbons, aliphatic hydrocarbon halides and aromatic hydrocarbon halides. In addition, an inert gas such as nitrogen, helium or argon may also be present in the reaction system as an inert substance in the reaction, and the above inert gases and low boiling point organic compounds inactive in the reaction may be introduced in gaseous form from the lower portion of a continuous multistage distillation column for the purpose of accelerating the distillation of low boiling point by-products formed.

Following completion of the disproportionation reaction, diaryl carbonate is obtained by removing the catalyst, alkyl aryl carbonate, aromatic hydroxy compound and alcohol by known methods.

There are no particular limitations on the type of reaction vessel used in the transesterification and disproportionation steps, and various known methods are used, examples of which may include types using a stirring tank, a multistage stirring tank or a multistage distillation column and combinations thereof. Batch type or continuous type reaction vessels can be used for these reaction vessels. Methods using a multistage distillation column are preferable from the viewpoint of efficiently shifting the equilibrium to the products side, and a continuous method using a multistage distillation column is particularly preferable. A multistage distillation column refers to a distillation column having multiple stages in which the number of theoretical plates of distillation is two or more, and any multistage distillation column may be used provided it allows continuous distillation. Any multistage distillation column can be used for the multistage distillation column provided it is ordinarily used as a multistage distillation column, examples of which may include tray column types using a bubble tray, a porous plate tray, a valve tray or a counter-current tray, and packed column types packed with various types of packing materials such as a raschig ring, a lessing ring, a pole ring, a Berl saddle, an Interlock saddle, a Dixon packing, a McMahon packing, Helipack, a Sulzer packing or Mellapak. Moreover, a combination tray-packed column type is also used preferably that combines a tray portion with a portion packed with a packing material. In the case of carrying out a continuous method using a multistage distillation column, the starting substances and reactants are continuously supplied to a continuous multistage distillation column, and simultaneous to carrying out the transesterification reaction and/or disproportionation reaction between both substances in the liquid phase or gas-liquid phase in the presence of a metal-containing catalyst within the distillation column, a high boiling point reaction mixture containing the alkyl aryl carbonate and/or diaryl carbonate produced is extracted in liquid form from the lower portion of the distillation column, while a low boiling point reaction mixture containing by-products formed is continuously extracted in a gaseous state from the upper portion of the distillation column by distillation, thereby resulting in the production diaryl carbonate.

Although the preceding description has indicated a production example of diaryl carbonate using a dialkyl tin compound, the following steps (4) and (5) can be carried out in addition to the above-mentioned steps (1) to (3), the steps (4) and (5) comprising the steps of:

step (4): forming an organic tin compound having a tin-oxygen-carbon bond and water by reacting the residue liquid obtained in step (2) with an alcohol followed by removing the water from the reaction system; and step (5): reusing the organic tin compound having the tin-oxygen-carbon bond obtained in step (4) as the organic tin compound having the tin-oxygen-carbon bond of step (1).

Step (4) is a step for regenerating the dialkyl tin compound by reacting the residue liquid obtained in step (2) with an alcohol.

Examples of alcohols used in this step may include alcohols such as methanol, ethanol, propanol (including isomers), butanol (including isomers), pentanol (including isomers), hexanol (including isomers), heptanol (including isomers), octanol (including isomers), nonanol (including isomers) or decanol (including isomers), and although an alcohol is preferably used in which the number of carbon atoms constituting the alcohol is a number selected from the group consisting of integers of from 1 to 12, more preferably an alcohol is used that is the same alcohol as the alcohol used in the alkyl tin alkoxide synthesis step above.

The conditions of the dehydration reaction are preferably the same as the conditions of the above-mentioned alkyl tin alkoxide synthesis step. The reaction may be terminated once the desired alkyl tin alkoxide composition has been obtained. Progression of the reaction is also determined by measuring the amount of water extracted outside the system, and can also be determined by a method using $^{119}$Sn-NMR by sampling the reaction liquid. In order to produce the mixture of the present embodiment in step (1), the reaction is terminated after confirming the obtaining of a composition in which the molar ratio of tetraalkyl dialkoxy distannoxane and dialkyl tin dialkoxide contained in the alkyl tin alkoxide composition obtained in the above reaction, when expressed as the combined molar ratio of both, is within a range of from 0:100 to 80:20 and more preferably within a range of from 10:90 to 70:30. The alcohol used may be used while still present in the reaction system, and the alcohol may also be used by distilling off the alcohol depending on the case. Since there is the advantage of being able to reduce the size of the reaction vessels of the other steps, it is preferable to remove as much of the alcohol as possible. Removal by known distillation is preferable for the removal method, and known distillation equipment can be used for the distiller used for distillation. A thin film distillation apparatus is preferably used for the distillation apparatus since the alcohol can be removed in a short period of time. Differing from the alkyl tin alkoxide synthesis step, since dialkyl tin oxide generally in a solid state is not used in this step, there are few restrictions on the reaction vessel. Namely, there are no particular limitations on the type of reaction vessel of the dehydration reaction, and a known tank type or column type reaction vessel can be used. A low boiling point reaction mixture containing water is extracted in gaseous form from the reaction vessel by distillation, while a high boiling point reaction mixture containing a produced alkyl tin alkoxide or alkyl tin alkoxide mixture is extracted in the form of a liquid from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a columnar reactor are preferable from the viewpoint of efficiently shifting the equilibrium to the products side, while a structure having a large gas-liquid contact area is preferable for being able to rapidly transfer the water formed to the gaseous phase. Continuous methods using a multitubular reactor, a multistage distillation column or a packed column packed with a packing are particularly preferable. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

The dialkyl tin compound produced in step (4) as described above is reused as the dialkyl tin compound used in step (1) according to the next step (5) (recycling step) in which the organic tin compound having the tin-oxygen-carbon bond obtained in step (4) is reused as the organic tin compound having the tin-oxygen-carbon bond of step (1).

<Amine Compound>

On the other hand, amine compounds represented by the following formula (17) are used for the amine compounds used in the production process according to the present embodiment:

(wherein $R^2$ represents a group selected from the group consisting of an aliphatic group having 1 to 20 carbon atoms and an aromatic group having 6 to 20 carbon atoms, the above group containing an atom selected from carbon and oxygen atoms, and having a valence equal to n, and n represents an integer of from 2 to 10).

In formula (17) above, a polyamine in which n is 2 or more is used preferably, and a diamine compound in which n is 2 is used more preferably.

In formula (17) above, $R^2$ is more preferably an alkyl group having 1 to 20 carbon atoms or a cycloalkyl group having 5 to 20 carbon atoms, and examples of $R^2$ may include linear hydrocarbons such as methylene, dimethylene, trimethylene, tetramethylene, pentamethylene, hexamethylene or octamethylene; unsubstituted alicyclic hydrocarbons such as cyclopentane, cyclohexane, cycloheptane, cyclooctane or bis(cyclohexyl)alkane; alkyl-substituted cyclohexanes such as methylcyclopentane, ethylcyclopentane, methylcyclohexane (including isomers), ethylcyclohexane (including isomers), propylcyclohexane (including isomers), butylcyclohexane (including isomers), pentylcyclohexane (including isomers) or hexylcyclohexane (including isomers); dialkyl-substituted cyclohexanes such as dimethylcyclohexane (including isomers), diethylcyclohexane (including isomers) or dibutylcyclohexane (including isomers); trialkyl-substituted cyclohexanes such as 1,5,5-trimethylcyclohexane, 1,5,5-triethylcyclohexane, 1,5,5-tripropylcyclohexane (including isomers) or 1,5,5-tributylcyclohexane (including isomers); monoalkyl-substituted benzenes such as toluene, ethylbenzene or propylbenzene; dialkyl-substituted benzenes such as xylene, diethylbenzene or dipropylbenzene; and aromatic hydrocarbons such as diphenylalkane or benzene. In particular, hexamethylene, phenylene, diphenylmethane, toluene, cyclohexane, xylenyl, methylcyclohexane, isophorone and dicyclohexylmethane groups are used preferably.

Examples of such polyamine compounds may include aliphatic diamines such as hexamethylene diamine, 4,4'-methylenebis(cyclohexylamine) (including isomers), cyclohexane diamine (including isomers) or 3-aminomethyl-3,5,5-trimethylcyclohexyl amine (including isomers); and aromatic diamines such as phenylene diamine (including isomers), toluene diamine (including isomers) or 4,4'-methylene dianiline (including isomers). Among these, aliphatic diamines such as hexamethylene diamine, 4,4'-methylenebis (cyclohexylamine) (including isomers), cyclohexane diamine (including isomers) and 3-aminomethyl-3,5,5-trimethylcyclohexyl amine (including isomers) are used preferably, while hexamethylene diamine, 4,4'-methylenebis(cyclohexylamine) and 3-aminomethyl-3,5,5-trimethylcyclohexyl amine are used more preferably.

<Reaction of Diaryl Carbonate and Amine Compound>

The following provides an explanation of the reaction between the previously explained diaryl carbonate and amine compound.

The reaction between the diaryl carbonate and amine compound is carried out in the presence of the aromatic hydroxy compound. Compounds having one hydroxyl group directly bonded to an aromatic hydrocarbon ring constituting the aromatic hydroxy compound are preferable for the aromatic hydroxy compound. Although the aromatic hydroxy compound having two or more hydroxyl groups directly bonded to an aromatic hydrocarbon ring constituting the aromatic hydroxy compound can also be used as the aromatic hydroxy compound constituting the composition according to the present embodiment, since there are cases in which the viscosity of the solution may be high in the reaction between the diaryl carbonate and the amine compound, this can lead to a decrease in reaction efficiency or lead to a decrease in efficiency when transferring the reaction liquid as described later.

Examples of aromatic hydroxy compounds used in the reaction between the diaryl carbonate and amine compound may include phenol; mono-substituted phenols such as methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers) or cumylphenol (including isomers); di-substituted phenols such as dimethylphenol (including isomers), diethylphenol (including isomers), dipropylphenol (including isomers), dibutylphenol (including isomers), dipentylphenol (including isomers), dihexylphenol (including isomers), diheptylphenol (including isomers), dioctylphenol (including isomers), dinonylphenol (including isomers), didecylphenol (including isomers), didodecylphenol (including isomers), diphenylphenol (including isomers), diphenoxyphenol (including isomers), dicumylphenol (including isomers), methylethylphenol (including isomers), methylpropylphenol (including isomers), methylbutylphenol (including isomers), methylpentylphenol (including isomers), methylhexylphenol (including isomers), methylheptylphenol (including isomers), methyloctylphenol (including isomers), methylnonylphenol (including isomers), methyldecylphenol (including isomers), methyldodecylphenol (including isomers), methylphenylphenol (including isomers), methylphenoxyphenol (including isomers), methylcumylphenol (including isomers), ethylpropylphenol (including isomers), ethylbutylphenol (including isomers), ethylpentylphenol (including isomers), ethylhexylphenol (including isomers), ethylheptylphenol (including isomers), ethyloctylphenol (including isomers), ethylnonylphenol (including isomers), ethyldecylphenol (including isomers), ethyldodecylphenol (including isomers), ethylphenylphenol (including isomers), ethylphenoxyphenol (including isomers), ethylcumylphenol (including isomers), propylbutylphenol (including isomers), propylpentylphenol (including isomers), propylhexylphenol (including isomers), propylheptylphenol (including isomers), propyloctylphenol (including isomers), propylnonylphenol (including isomers), propyldecylphenol (including isomers), propyldodecylphenol (including isomers), propylphenylphenol (including isomers), propylphenoxyphenol (including isomers), propylcumylphenol (including isomers), butylpentylphenol (including isomers), butylhexylphenol (including isomers), butylheptylphenol (including isomers), butyloctylphenol (including isomers), butylnonylphenol (including isomers), butyldecylphenol (including isomers), butyldodecylphenol (including isomers), butylphenylphenol (including isomers), butylphenoxyphenol (including isomers), butylcumylphenol (including isomers), pentylhexylphenol (including isomers), pentylheptylphenol (including isomers), pentyloctylphenol (including isomers), pentylnonylphenol (including isomers), pentyldecylphenol (including isomers), pentyldodecylphenol (including isomers), pentylphenylphenol (including isomers), pentylphenoxyphenol (including isomers), pentylcumylphenol (including isomers), hexylheptylphenol (including isomers), hexyloctylphenol (including isomers), hexylnonylphenol (including isomers), hexyldecylphenol (including isomers), hexyldodecylphenol (including isomers), hexylphenylphenol (including isomers), hexylphenoxyphenol (including isomers), hexylcumylphenol (including isomers), heptyloctylphenol (including isomers), heptylnonylphenol (including isomers), heptyldecylphenol (including isomers), heptyldodecylphenol (including isomers), heptylphenylphenol (including isomers), heptylphenoxyphenol (including isomers), heptylcumylphenol (including isomers), octylnonylphenol (including isomers), octyldecylphenol (including isomers), octyldodecylphenol (including isomers), octylphenylphenol (including isomers), octylphenoxyphenol (including isomers), octylcumylphenol (including isomers), nonyldecylphenol (including isomers), nonyldodecylphenol (including isomers), nonylphenylphenol (including isomers), nonylphenoxyphenol (including isomers), nonylcumylphenol (including isomers), dodecylphenylphenol (including isomers), dodecylphenoxyphenol (including isomers) or dodecylcumylphenol (including isomers); and, tri-substituted phenols such as trimethylphenol (including isomers), triethylphenol (including isomers), tripropylphenol (including isomers), tributylphenol (including isomers), tripentylphenol (including isomers), trihexylphenol (including isomers), triheptylphenol (including isomers), trioctylphenol (including isomers), trinonylphenol (including isomers), tridecylphenol (including isomers), tridodecylphenol (including isomers), triphenylphenol (including isomers), triphenoxyphenol (including isomers), tricumylphenol (including isomers), dimethylethylphenol (including isomers), dimethylpropylphenol (including isomers), dimethylbutylphenol (including isomers), dimethylpentylphenol (including isomers), dimethylhexylphenol (including isomers), dimethylheptylphenol (including isomers), dimethyloctylphenol (including isomers), dimethylnonylphenol (including isomers), dimethyldecylphenol (including isomers), dimethyldodecylphenol (including isomers), dimethylphenylphenol (including isomers), dimethylphenoxyphenol (including isomers), dimethylcumylphenol (including isomers), diethylmethylphenol (including isomers), diethylpropylphenol (including isomers), diethylbutylphenol (including isomers), diethylpentylphenol (including isomers), diethylhexylphenol (including isomers), diethylheptylphenol (including isomers), diethyloctylphenol (including isomers), diethylnonylphenol (including isomers), diethyldecylphenol (including isomers), diethyldodecylphenol (including isomers), diethylphenylphenol (including isomers), diethylphenoxyphenol (including isomers), diethylcumylphenol (including isomers), dipropylmethylphenol (including isomers), dipropylethylphenol (including isomers), dipropylbutylphenol (including isomers), dipropylpentylphenol (including isomers), dipropylhexylphenol (including isomers), dipropylheptylphenol (including isomers), dipropyloctylphenol (including isomers), dipropylnonylphenol (including isomers), dipropyldecylphenol (including isomers), dipropyldodecylphenol (including isomers), dipropylphenylphenol (including isomers), dipropylphenoxyphenol (including isomers), dipropylcumylphenol (including isomers), dibutylmethylphenol (including isomers), dibutylethylphenol (including isomers), dibutylpropylphenol (including isomers), dibutylpentylphenol (including isomers), dibutylhexylphenol (including isomers), dibutylheptylphenol (including isomers), dibutyloctylphenol (including isomers), dibutylnonylphenol (including isomers), dibutyldecylphenol (including isomers), dibutyldodecylphenol (including isomers), dibutylphenylphenol (including isomers), dibutylphenoxyphenol (including isomers), dibutylcumylphenol (including isomers), dipentylmethylphenol (including isomers), dipentylethylphenol (including isomers), dipentylpropylphenol (including isomers), dipentylbutylphenol (including isomers), dipentylhexylphenol (including isomers), dipentylheptylphenol (including isomers), dipentyloctylphenol (including isomers), dipentylnonylphenol (including isomers), dipentyldecylphenol (including isomers), dipentyldodecylphenol (including isomers), dipentylphenylphenol (including isomers), dipentylphenoxyphenol (including isomers), dipentylcumylphenol (including isomers), dihexylmethylphenol (including isomers), dihexylethylphenol (including isomers), dihexylpropylphenol (including isomers), dihexylbutylphenol (including isomers), dihexylpentylphenol (including isomers), dihexylheptylphenol (including isomers), dihexyloctylphenol (including isomers), dihexylnonylphenol (including isomers), dihexyldecylphenol (including isomers), dihexyldodecylphenol (including isomers), dihexylphenylphenol (including isomers), dihexylphenoxyphenol (including isomers), dihexylcumylphenol (including isomers), diheptylmethylphenol (including isomers), diheptylethylphenol (including isomers), diheptylpropylphenol (including isomers), diheptylbutylphenol (including isomers), diheptylpentylphenol (including isomers), diheptylhexylphenol (including isomers), diheptyloctylphenol (including isomers), diheptylnonylphenol (including isomers), diheptyldecylphenol (including isomers), diheptyldodecylphenol (including isomers), diheptylphenylphenol (including isomers), diheptylphenoxyphenol (including isomers), diheptylcumylphenol (including isomers), dioctylmethylphenol (including isomers), dioctylethylphenol (including isomers), dioctylpropylphenol (including isomers), dioctylbutylphenol (including isomers), dioctylpentylphenol (including isomers), dioctylhexylphenol (including isomers), dioctylheptylphenol (including isomers), dioctylnonylphenol (including isomers), dioctyldecylphenol (including isomers), dioctyldodecylphenol (including isomers), dioctylphenylphenol (including isomers), dioctylphenoxyphenol (including isomers), dioctylcumylphenol (including isomers), dinonylmethylphenol (including isomers), dinonylethylphenol (including isomers), dinonylpropylphenol (including isomers), dinonylbutylphenol (including isomers), dinonylpentylphenol (including isomers), dinonylhexylphenol (including isomers), dinonylheptylphenol (including isomers), dinonyloctylphenol (including isomers), dinonyldecylphenol (including isomers), dinonyldodecylphenol (including isomers), dinonylphenylphenol (including isomers), dinonylphenoxyphenol (including isomers), dinonylcumylphenol (including isomers), didecylmethylphenol (including isomers), didecylethylphenol (including isomers), didecylpropylphenol (including isomers), didecylbutylphenol (including isomers), didecylpentylphenol (including isomers), didecylhexylphenol (including isomers), didecylheptylphenol (including isomers), didecyloctylphenol (including isomers), didecylnonylphenol (including isomers), didecyldodecylphenol (including isomers), didecylphenylphenol (including isomers), didecylphenoxyphenol (including isomers), didecylcumylphenol (including isomers), didodecylmethylphenol (including isomers), didodecylethylphenol (including isomers), didodecylpropylphenol (including isomers), didodecylbutylphenol (including isomers), didodecylpentylphenol (including isomers), didodecylhexylphenol (including isomers), didodecylheptylphenol (including isomers), didodecyloctylphenol (including isomers), didodecylnonylphenol (including isomers), didodecyldecylphenol (including isomers), didodecyldodecylphenol (including isomers), didodecylphenylphenol (including isomers), didodecylphenoxyphenol (including isomers), didodecylcumylphenol (including isomers), diphenylmethylphenol (including isomers), diphenylethylphenol (including isomers), diphenylpropylphenol (including isomers), diphenylbutylphenol (including isomers), diphenylpentylphenol (including isomers), diphenylhexylphenol (including isomers), diphenylheptylphenol (including isomers), diphenyloctylphenol (including isomers), diphenylnonylphenol (including isomers), diphenyldecylphenol (including isomers), diphenyldodecylphenol (including isomers), diphenylphenoxyphenol (including isomers), diphenylcumylphenol (including isomers), diphenoxymethylphenol (including isomers), diphenoxyethylphenol (including isomers), diphenoxypropylphenol (including isomers), diphenoxybutylphenol (including isomers), diphenoxypentylphenol (including isomers), diphenoxyhexylphenol (including isomers), diphenoxyheptylphenol (including isomers), diphenoxyoctylphenol (including isomers), diphenoxynonylphenol (including isomers), diphenoxydecylphenol (including isomers), diphenoxydodecylphenol (including isomers), diphenoxyphenylphenol (including isomers), diphenoxycumylphenol (including isomers), dicumylmethylphenol (including isomers), dicumylethylphenol (including isomers), dicumylpropylphenol (including isomers), dicumylbutylphenol (including isomers), dicumylpentylphenol (including isomers), dicumylhexylphenol (including isomers), dicumylheptylphenol (including isomers), dicumyloctylphenol (including isomers), dicumylnonylphenol (including isomers), dicumyldecylphenol (including isomers), dicumyldodecylphenol (including isomers), dicumylphenylphenol (including isomers), dicumylphenoxyphenol (including isomers), methylethylpropylphenol (including isomers), methylethylbutylphenol (including isomers), methylethylpentylphenol (including isomers), methylethylhexylphenol (including isomers), methylethylheptylphenol (including isomers), methylethyloctylphenol (including isomers), methylethylnonylphenol (including isomers), methylethyldecylphenol (including isomers), methylethyldodecylphenol (including isomers), methylethylphenylphenol (including isomers), methylethylphenoxyphenol (including isomers), methylethylcumylphenol (including isomers), methylpropylbutylphenol (including isomers), methylpropylpentylphenol (including isomers), methylpropylhexylphenol (including isomers), methylpropylheptylphenol (including isomers), methylpropyloctylphenol (including isomers), methylpropylnonylphenol (including isomers), methylpropyldecylphenol (including isomers), methylpropyldodecylphenol (including isomers), methylpropylphenylphenol (including isomers), methylpropylphenoxyphenol (including isomers), methylpropylcumylphenol (including isomers), methylbutylpentylphenol (including isomers), methylbutylhexylphenol (including isomers), methylbutylheptylphenol (including isomers), methylbutyloctylphenol (including isomers), methylbutylnonylphenol (including isomers), methylbutyldecylphenol (including isomers), methylbutyldodecylphenol (including isomers), methylbutylphenylphenol (including isomers), methylbutylphenoxyphenol (including isomers), methylbutylcumylphenol (including isomers), methylpentylhexylphenol, methylpentylheptylphenol (including isomers), methylpentyloctylphenol (including isomers), methylpentylnonylphenol (including isomers), methylpentyldecylphenol (including isomers), methylpentyldodecylphenol (including isomers), methylpentylphenylphenol (including isomers), methylpentylphenoxyphenol (including isomers), methylpentylcumylphenol (including isomers), methylhexylheptylphenol (including isomers), methylhexyloctylphenol (including isomers), methylhexylnonylphenol (including isomers), methylhexyldecylphenol (including isomers), methylhexyldodecylphenol (including isomers), methylhexylphenylphenol (including isomers), methylhexylphenoxyphenol (including isomers), methylhexylcumylphenol (including isomers), ethylpropylbutylphenol (including isomers), ethylpropylpentylphenol (including isomers), ethylpropylhexylphenol (including isomers), ethylpropylheptylphenol (including isomers), ethylpropyloctyl phenol (including isomers), ethylpropylnonylphenol (including isomers), ethylpropyldecylphenol (including isomers), ethylpropyldodecylphenol (including isomers), ethylpropylphenylphenol (including isomers), ethylpropylphenoxyphenol (including isomers), ethylpropylcumylphenol (including isomers), ethylbutylphenol (including isomers), ethylbutylpentylphenol (including isomers), ethylbutylhexylphenol (including isomers), ethylbutylheptylphenol (including isomers), ethylbutyloctylphenol (including isomers), ethylbutylnonylphenol (including isomers), ethylbutyldecylphenol (including isomers), ethylbutyldodecylphenol (including isomers), ethylbutylphenylphenol (including isomers), ethylbutylphenoxyphenol (including isomers), ethylbutylcumylphenol (including isomers), ethylpentylhexylphenol (including isomers), ethylpentylheptylphenol (including isomers), ethylpentyloctylphenol (including isomers), ethylpentylnonylphenol (including isomers), ethylpentyldecylphenol (including isomers), ethylpentyldodecylphenol (including isomers), ethylpentylphenylphenol (including isomers), ethylpentylphenoxyphenol (including isomers), ethylpentylcumylphenol (including isomers), ethylhexylheptylphenol (including isomers), ethylhexyloctylphenol (including isomers), ethylhexylnonylphenol (including isomers), ethylhexyldecylphenol (including isomers), ethylhexyldodecylphenol (including isomers), ethylhexylphenylphenol (including isomers), ethylhexylphenoxyphenol (including isomers), ethylhexylcumylphenol (including isomers), ethylheptyloctylphenol (including isomers), ethylheptylnonylphenol (including isomers), ethylheptyldecylphenol (including isomers), ethylheptyldodecylphenol (including isomers), ethylheptylphenylphenol (including isomers), ethylheptylphenoxyphenol (including isomers), ethylheptylcumylphenol (including isomers), ethyloctylphenol (including isomers), ethyloctylnonylphenol (including isomers), ethylocyldecylphenol (including isomers), ethyloctyldodecylphenol (including isomers), ethyloctylphenylphenol (including isomers), ethyloctylphenoxyphenol (including isomers), ethyloctylcumylphenol (including isomers), ethylnonyldecylphenol (including isomers), ethylnonyldodecylphenol (including isomers), ethylnonylphenylphenol (including isomers), ethylnonylphenoxyphenol (including isomers), ethylnonylcumylphenol (including isomers), ethyldecyldodecylphenol (including isomers), ethyldecylphenylphenol (including isomers), ethyldecylphenoxyphenol (including isomers), ethyldecylcumylphenol (including isomers), ethyldodecylphenylphenol (including isomers), ethyldodecylphenoxyphenol (including isomers), ethyldodecylcumylphenol (including isomers), ethylphenylphenoxyphenol (including isomers), ethylphenylcumylphenol (including isomers), propylbutylphenol (including isomers), propylbutylpentylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpentylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propylhexylphenol (including isomers), propylhexylheptylphenol (including isomers), propylhexyloctylphenol (including isomers), propylhexylnonylphenol (including isomers), propylhexyldecylphenol (including isomers), propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptyldecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), propyloctylphenoxyphenol (including isomers), propyloctylcumylphenol (including isomers), propylnonyldecylphenol (including isomers), propylnonyldodecylphenol (including isomers), propylnonylphenylphenol (including isomers), propylnonylphenoxyphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propyldodecylphenoxyphenol (including isomers), propyldodecylcumylphenol (including isomers), methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers), cumylphenol (including isomers), propylphenylphenoxyphenol (including isomers), propylphenylcumylphenol (including isomers), propylphenoxycumylphenol (including isomers), propylbutylpentylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpentylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propylhexylheptylphenol (including isomers), propylhexyloctylphenol (including isomers), propylhexylnonylphenol (including isomers), propylhexyldecylphenol (including isomers), propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptyldecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), propyloctylphenoxyphenol (including isomers), propyloctylcumylphenol (including isomers), propylnonyldecylphenol (including isomers), propylnonyldodecylphenol (including isomers), propylnonylphenylphenol (including isomers), propylnonylphenoxyphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propyldodecylphenoxyphenol (including isomers), propylphenylphenoxyphenol (including isomers), propylphenylcumylphenol (including isomers), butylpentylhexylphenol (including isomers), butylpentylheptylphenol (including isomers), butylpentyloctylphenol (including isomers), butylpentylnonylphenol (including isomers), butylpentyldecylphenol (including isomers), butylpentyldodecylphenol (including isomers), butylpentylphenylphenol (including isomers), butylpentylphenoxyphenol (including isomers), butylpentylcumylphenol (including isomers), butylhexylheptylphenol (including isomers), butylhexyloctylphenol (including isomers), butylhexylnonylphenol (including isomers), butylhexyldecylphenol (including isomers), butylhexyldodecylphenol (including isomers), butylhexylphenylphenol (including isomers), butylhexylphenoxyphenol (including isomers), butylhexylcumylphenol (including isomers), butylheptyloctylphenol (including isomers), butylheptylnonylphenol (including isomers), butylheptyldecylphenol (including isomers), butylheptyldodecylphenol (including isomers), butylheptylphenylphenol (including isomers), butylheptylphenoxyphenol (including isomers), butylheptylcumylphenol (including isomers), butyloctylnonylphenol (including isomers), butyloctyldecylphenol (including isomers), butyloctyldodecylphenol (including isomers), butyloctylphenylphenol (including isomers), butyloctylphenoxyphenol (including isomers), butyloctylcumylphenol (including isomers), butylnonyldecylphenol (including isomers), butylnonyldodecylphenol (including isomers), butylnonylphenylphenol (including isomers), butylnonylphenoxyphenol (including isomers), butylnonylcumylphenol (including isomers), butyldecyldodecylphenol (including isomers), butyldecylphenylphenol (including isomers), butyldecylphenoxyphenol (including isomers), butyldecylcumylphenol (including isomers), butyldodecylphenol (including isomers), butyldodecylphenylphenol (including isomers), butyldodecylphenoxyphenol (including isomers), butyldodecylcumylphenol (including isomers), butylphenylphenol (including isomers), butylphenylphenoxyphenol (including isomers), butylphenylcumylphenol (including isomers), pentylhexylheptylphenol (including isomers), pentylhexyloctylphenol (including isomers), pentylhexylnonylphenol (including isomers), pentylhexyldecylphenol (including isomers), pentylhexyldodecylphenol (including isomers), pentylhexylphenylphenol (including isomers), pentylhexylphenoxyphenol (including isomers), pentylhexylcumylphenol (including isomers), pentylhetpyloctylphenol (including isomers), pentylheptylnonylphenol (including isomers), pentylheptyldecylphenol (including isomers), pentylheptyldodecylphenol (including isomers), pentylheptylphenylphenol (including isomers), pentylheptylphenoxyphenol (including isomers), pentylheptylcumylphenol (including isomers), pentyloctylnonylphenol (including isomers), pentyloctyldecylphenol (including isomers), pentyloctyldodecylphenol (including isomers), pentyloctylphenylphenol (including isomers), pentyloctylphenoxyphenol (including isomers), pentyloctylcumylphenol (including isomers), pentylnonyldecylphenol (including isomers), pentylnonyldodecylphenol (including isomers), pentylnonylphenylphenol (including isomers), pentylnonylphenoxyphenol (including isomers), pentylnonylcumylphenol (including isomers), pentyldecyldodecylphenol (including isomers), pentyldecylphenylphenol (including isomers), pentyldecylphenoxyphenol (including isomers), pentyldecylcumylphenol (including isomers), pentyldodecylphenylphenol (including isomers), pentyldodecylphenoxyphenol (including isomers), pentyldodecylcumylphenol (including isomers), pentylphenylphenoxyphenol (including isomers), pentylphenylcumylphenol (including isomers), hexylheptyloctylphenol (including isomers), hexylheptylnonylphenol (including isomers), hexylheptyldecylphenol (including isomers), hexylheptyldodecylphenol (including isomers), hexylheptylphenylphenol (including isomers), hexylheptylphenoxyphenol (including isomers), hexylheptylcumylphenol (including isomers), hexyloctylnonylphenol (including isomers), hexyloctyldecylphenol (including isomers), hexyloctyldodecylphenol (including isomers), hexyloctylphenylphenol (including isomers), hexyloctylphenoxyphenol (including isomers), hexyloctylcumylphenol (including isomers), hexylnonyldecylphenol (including isomers), hexylnonyldodecylphenol (including isomers), hexylnonylphenylphenol (including isomers), hexylnonylphenoxyphenol (including isomers), hexyldecylphenylphenol (including isomers), hexyldecylphenoxyphenol (including isomers), hexyldecylcumylphenol (including isomers), hexyldodecylphenylphenol (including isomers), hexyldodecylphenoxyphenol (including isomers), hexyldodecylcumylphenol (including isomers), hexylphenylphenoxyphenol (including isomers), hexylphenylcumylphenol (including isomers), heptyloctylnonylphenol (including isomers), heptyloctyldecylphenol (including isomers), heptyloctyldodecylphenol (including isomers), heptyloctylphenylphenol (including isomers), heptyloctylphenoxyphenol (including isomers), heptyloctylcumylphenol (including isomers), heptylnonyldecylphenol (including isomers), heptylnonyldodecylphenol (including isomers), heptylnonylphenylphenol (including isomers), heptylnonylphenoxyphenol (including isomers), heptylnonylcumylphenol (including isomers), heptyldecyldodecylphenol (including isomers), heptyldecylphenylphenol (including isomers), heptyldecylphenoxyphenol (including isomers), heptyldecylcumylphenol (including isomers), heptyldodecylphenylphenol (including isomers), heptyldodecylphenoxyphenol (including isomers), heptyldodecylcumylphenol (including isomers), heptylphenylphenoxyphenol (including isomers), heptylphenylcumylphenol (including isomers), octylnonyldecylphenol (including isomers), octylnonyldodecylphenol (including isomers), octylnonylphenylphenol (including isomers), octylnonylphenoxyphenol (including isomers), octylnonylcumylphenol (including isomers), octyldecyldodecylphenol (including isomers), octyldecylphenylphenol (including isomers), octyldecylphenoxyphenol (including isomers), octyldecylcumylphenol (including isomers), octyldodecylphenylphenol (including isomers), octyldodecylphenoxyphenol (including isomers), octyldodecylcumylphenol (including isomers), octylphenylphenoxyphenol (including isomers), octylphenylcumylphenol (including isomers), nonyldecyldodecylphenol (including isomers), nonyldecylphenylphenol (including isomers), nonyldecylphenoxyphenol (including isomers), nonyldecylcumylphenol (including isomers), nonyldodecylphenylphenol (including isomers), nonyldodecylphenoxyphenol (including isomers), nonyldodecylcumylphenol (including isomers), nonylphenylphenoxyphenol (including isomers), nonylphenylcumylphenol (including isomers), decyldodecylphenylphenol (including isomers), decyldodecylphenoxyphenol (including isomers), decyldodecylcumylphenol (including isomers), decylphenylphenoxyphenol (including isomers), decylphenylcumylphenol (including isomers), dodecylphenylphenoxyphenol (including isomers), dodecylphenylcumylphenol (including isomers) or phenylphenoxycumylphenol (including isomers). Among these aromatic hydroxy compounds, compounds corresponding to compound $R^1OH$ in which a hydrogen atom is added to a group $R^1O$ constituting diaryl carbonate (wherein $R^1$ represents an aromatic group as previously defined, and O represents an oxygen atom) are used more preferably. This is because the types of compounds in the reaction mixture obtained by reacting the diaryl carbonate and amine compound can be reduced, thereby facilitating the separation procedure.

The amine compound is preferably supplied in a liquid state to the reaction vessel in which production of aryl carbamate is carried out. In general, most of the amine compound as exemplified above is a solid at normal temperature (e.g., 20° C.), and in such cases, although the amine compound can be supplied in a liquid state by heating to a temperature equal to or higher than the melting point of the amine compound, if the amine compound is supplied at an excessively high temperature, since there are cases in which side-reactions such as thermal denaturation reactions caused by heating may occur, the amine compound is preferably supplied in a liquid state at a comparatively low temperature in the form of a mixture with the above-mentioned aromatic hydroxy compound, diaryl carbonate or water.

Although varying according to the reacted compounds, the reaction conditions under which the reaction between the diaryl carbonate and amine compound is carried out are such that the stoichiometric ratio of the diaryl carbonate to the amino groups of the amine compound is within a range of from 1 to 1000 times, and although the diaryl carbonate is preferably in excess with respect to the amino groups of the amine compound in order to complete the reaction quickly by increasing the reaction rate, in consideration of the size of the reaction vessel, the stoichiometric ratio is preferably within a range of from 1.1 to 50 times and more preferably within a range of from 1.5 to 10 times. The amount of the aromatic hydroxy compound used is such that the stoichiometric ratio of the aromatic hydroxy compound to the amino groups of the amine compound is within a range of from 1 to 100 times, preferably within a range of from 1.2 to 50 times and more preferably within a range of from 1.5 to 10 times. The reaction temperature is generally within a range of from 0 to 150° C. Although a high temperature is preferable for increasing the reaction rate, on the other hand, since undesirable reactions also occur at high temperatures, the reaction temperature is preferably within a range of from 10 to 100° C. A known cooling apparatus or heating apparatus may be installed in the reaction vessel to maintain a constant reaction temperature. In addition, although varying according to the types of compounds used and the reaction temperature, the reaction pressure may be decreased pressure, normal pressure or increased pressure, and the reaction is generally carried out within a range of from 20 to $1\times10^6$ Pa. There are no particular limitations on the reaction time (residence time in the case of a continuous process), and is generally from 0.001 to 50 hours, preferably from 0.01 to 20 hours and more preferably from 0.1 to 10 hours. In addition, the reaction can also be terminated by confirming that a desired amount of aryl carbamate has been formed by, for example, liquid chromatography after sampling the reaction liquid.

In the present embodiment, it is preferable to not use a catalyst in the reaction between the diaryl carbonate and amine compound. During the transfer of a reaction mixture and during a thermal decomposition reaction of carbamic acid ester contained in the reaction mixture to be described later, if the aryl carbamate is heated in the presence of a metal component originating from a catalyst, a thermal denaturation reaction and so forth of the aryl carbamate may occur. Although a catalyst can be used when carrying out the reaction between the diaryl carbonate and amine compound followed by carrying out transfer or a thermal decomposition reaction on the reaction mixture after having gone through a step for removing the catalyst, this results in an increase in the number of steps, thereby making this undesirable.

However, a catalyst may be used for the purpose of, for example, completing the reaction in a short period of time or lowering the reaction temperature. In general, since aromatic amine compounds have lower reactivity than aliphatic amine compounds, in the case of using the aromatic amine compound for the amine compound, there are cases in which it is effective to use a catalyst. In the case of using a catalyst, examples of catalysts that can be used may include organic metal compounds and inorganic metal compounds of tin, lead, copper or titanium, and basic catalysts such as alcoholates of alkaline metals or alkaline earth metals in the form of methylates, ethylates and butyrates (including isomers) of lithium, sodium, potassium, calcium or barium.

A reaction solvent other than the above-mentioned aromatic hydroxy compound and/or excess diaryl carbonate is preferably not used in the present embodiment. Although there are cases in which processes have been disclosed in the prior art that use an inert reaction solvent with respect to isocyanates and carbamic acid esters formed by a thermal decomposition reaction of diaryl carbamates, the use of such an inert solvent makes the separation and so forth of isocyanates and aromatic hydroxy compounds formed by the thermal decomposition reaction of carbamic acid ester described later complex, thereby making this undesirable.

A known tank type reaction vessel, a column type reaction vessel or a distillation column can be used for the reaction vessel used in the reaction between the diaryl carbonates and the amine compounds, and although known materials may be used for the reaction vessel and lines provided they do not have a detrimental effect on the starting substances or reactants, SUS304, SUS316 or SUS316L and the like can be used preferably since they are inexpensive.

<Aryl Carbamate>

A mixture containing an aryl carbamate, excess diaryl carbonate and aromatic hydroxy compound is obtained by the subject reaction.

The aryl carbamate is a compound represented by the following formula (18):

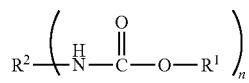

(wherein $R^2$ has the same definition as previously defined and represents a group originating from an amine compound, $R^1$ has the same definition as previously defined and represents a group originating from a diaryl carbonate, and n represents an integer of from 2 to 10, and is the same as the number of amino groups of the amine compound).

Examples of carbamic acid esters represented by the formula (18) above may include aryl carbamates such as N,N'-hexanediyl-bis-carbamic acid diphenyl ester, N,N'-hexanediyl-bis-carbamic acid di(methylphenyl) ester (including isomers), N,N'-hexanediyl-bis-carbamic acid di(ethylphenyl) ester (including isomers), N,N'-hexanediyl-bis-carbamic acid di(propylphenyl) ester (including isomers), N,N'-hexanediyl-bis-carbamic acid di(butylphenyl) ester (including isomers), N,N'-hexanediyl-bis-carbamic acid di(pentylphenyl) ester (including isomers), diphenyl-4,4'-methylene-dicyclohexylcarbamate, di(methylphenyl)-4,4'-methylene-dicyclohexylcarbamate, di(ethylphenyl)-4,4'-methylene-dicyclohexylcarbamate, di(propylphenyl)-4,4'-methylene-dicyclohexylcarbamate (including isomers), di(butylphenyl)-4,4'-methylene-dicyclohexylcarbamate (including isomers), di(pentylphenyl)-4,4'-methylene-dicyclohexylcarbamate (including isomers), di(hexylphenyl)-4,4'-methylene-dicyclohexylcarbamate (including isomers), di(heptylphenyl)-4,4'-methylene-dicyclohexylcarbamate (including isomers), di(octylphenyl)-4,4'-methylene-dicyclohexylcarbamate (including isomers), 3-(phenoxycarbonylaminomethyl)-3,5,5-trimethylcyclohexyl carbamic acid phenyl ester, 3-(methylphenoxycarbonylaminomethyl)-3,5,5-trimethylcyclohexyl carbamic acid (methylphenoxy) ester (including isomers), 3-(ethylphenoxycarbonylaminomethyl)-3,5,5-trimethylcyclohexyl carbamic acid (ethylphenyl) ester (including isomers), 3-(propylphenoxycarbonylaminomethyl)-3,5,5-trimethylcyclohexyl carbamic acid (propylphenyl) ester (including isomers), 3-(butylphenoxycarbonylaminomethyl)-3,5,5-trimethylcyclohexyl carbamic acid (butylphenyl) ester (including isomers), 3-(pentylphenoxycarbonylaminomethyl)-3,5,5-trimethylcyclohexyl carbamic acid (pentylphenyl) ester (including isomers), 3-(hexylphenoxycarbonylaminomethyl)-3,5,5-trimethylcyclohexyl carbamic acid (hexylphenyl) ester (including isomers), 3-(heptylphenoxycarbonylaminomethyl)-3,5,5-trimethylcyclohexyl carbamic acid (heptylphenyl) ester (including isomers), 3-(octylphenoxycarbonylaminomethyl)-3,5,5-trimethylcyclohexyl carbamic acid (octylphenyl) ester (including isomers), toluene dicarbamic acid diphenyl ester (including isomers), toluene dicarbamic acid di(methylphenyl) ester (including isomers), toluene dicarbamic acid di(ethylphenyl) ester (including isomers), toluene dicarbamic acid di(propylphenyl) ester (including isomers), toluene dicarbamic acid di(butylphenyl) ester (including isomers), toluene dicarbamic acid di(pentylphenyl) ester (including isomers), toluene dicarbamic acid di(hexylphenyl) ester (including isomers), toluene dicarbamic acid di(heptylphenyl) ester (including isomers), toluene dicarbamic acid di(octylphenyl) ester (including isomers), N,N'-(4,4'-methanediyl-diphenyl)-biscarbamic acid diphenyl ester, N,N'-(4,4'-methanediyl-diphenyl)-biscarbamic acid di(methylphenyl) ester, N,N'-(4,4'-methanediyl-diphenyl)-biscarbamic acid di(ethylphenyl) ester, N,N'-(4,4'-methanediyl-diphenyl)-biscarbamic acid di(propylphenyl) ester, N,N'-(4,4'-methanediyl-diphenyl)-biscarbamic acid di(butylphenyl) ester, N,N'-(4,4'-methanediyl-diphenyl)-biscarbamic acid di(pentylphenyl) ester, N,N'-(4,4'-methanediyl-diphenyl)-biscarbamic acid di(hexylphenyl) ester, N,N'-(4,4'-methanediyl-diphenyl)-biscarbamic acid di(heptylphenyl) ester or N,N'-(4,4'-methanediyl-diphenyl)-biscarbamic acid di(octylphenyl) ester (including isomers).

<Transfer of Urethanation Reaction Liquid>

The reaction liquid containing aryl carbamate produced according to the process described above is preferably extracted from the reaction vessel in which the reaction is carried out and transferred to a reaction vessel in which a thermal decomposition reaction is carried out on the aryl carbamate (hereinafter referred to as "thermal decomposition reaction vessel") followed by carrying out a thermal decomposition reaction of the aryl carbamate. In this manner, by using separate reaction vessel for producing aryl carbamate from the thermal decomposition reaction vessel, reaction vessels suitable for each reaction can be selected, and the reaction conditions can be set flexibly, thereby making it possible to increase the yield in each reaction.

Since these aryl carbamates easily form hydrogen bonds between molecules by urethane bonds constituting the aryl carbamate, they frequency have a high melting point. In the transfer of these aryl carbamates, a solid carbamic acid ester, for example, is crushed or treated with a vehicle for processing into pellets and the like prior to transfer. However, in the case of transferring a solid aryl carbamate that has been treated with a vehicle, there is a frequently the need for a complex apparatus to ensure stable transfer of a fixed amount of aryl carbamate, or the need for a process for maintaining the form of the aryl carbamate within a certain range in cases of the risk of clogging of the transfer line or frequent fluctuations in the form of the aryl carbamate. Thus, the aryl carbamate is preferably supplied to the thermal decomposition reaction vessel in a liquid form.

The method for supplying the aryl carbamate to the thermal decomposition reaction vessel in the liquid form preferably employs a method in which the aryl carbamate is supplied in the form of a reaction mixture obtained by reacting the diaryl carbonate and the amine compound.

Although the aryl carbamate may also be transferred by heating the aryl carbamate to a temperature higher than the melting point thereof, in consideration of preventing solidification during transfer, it is necessary to heat the aryl carbamate to a temperature higher than the melting point thereof (e.g., 200° C.). In the case of maintaining the aryl carbamate at such a high temperature, thermal decomposition of the aryl carbamate frequently occurs at undesirable locations to produce isocyanates or a thermal denaturation reaction frequently occurs in the aryl carbamate as previously described.

In contrast thereto, since a reaction mixture obtained by reacting the diaryl carbonate and the amine compound is a liquid at normal temperature (20° C.), or even if it is a solid at normal temperature, since it frequently becomes a homogeneous solution at a temperature lower than the melting point of the aryl carbamate, thermal denaturation and the like of the aryl carbamate can be inhibited.

In addition, the inventors of the present invention unexpectedly found that when the aryl carbamate is transferred in the form of a reaction mixture obtained by reacting the diaryl carbonate and the amine compound, reductions in the amount of the aryl carbamate caused by thermal denaturation and so forth of the aryl carbamate are inhibited. Although the mechanism by which this effect is demonstrated is not clear, the inventors of the present invention presumed that, as a result of the aromatic hydroxy compound contained in the reaction mixture and the urethane bonds (—NHCOO—) of the carbamic acid ester forming hydrogen bonds in the reaction by which urea bonds are formed as represented by the above formula (2), since the urethane bonds are in a state in which they are unable to approach each other, it is difficult for reactions that form urea bonds to occur.

Transfer of the reaction mixture is preferably carried out within the temperature range of from 10 to 180° C., more preferably from 30 to 170° C. and even more preferably from 50 to 150° C.

In a process by which the aryl carbamate is supplied to a thermal decomposition reaction in the form of a reaction mixture obtained by reacting the diaryl carbonate and the amine compound, since the reaction mixture is supplied without having to carry out a distillative separation procedure and the like, there is the advantage of being able to simplify the process. In addition, in the case of a process by which the aryl carbamate is supplied in the form of a mixture in which all or a portion of the aromatic hydroxy compound has been separated from the reaction mixture as well, the process can also be simplified since it is not necessary to carry out a procedure for isolating only the aryl carbamate from the reaction mixture.

<Aryl Carbamate Thermal Decomposition Reaction>

Next, an explanation is provided of the production of isocyanate by carrying out a thermal decomposition reaction of the aryl carbamate.

The thermal decomposition reaction in the present embodiment is a reaction in which a corresponding isocyanate and aromatic hydroxy compound are formed from the aryl carbamate.

The reaction temperature is generally within a range of from 100 to 300° C., and although a high temperature is preferable for increasing the reaction rate, since side reactions as described above may be conversely caused by the aryl carbamate and/or the reaction product in the form of the isocyanate at high temperatures, the reaction temperature is preferably within a range of from 150 to 250° C. A known cooling apparatus or heating apparatus may be installed in the reaction vessel to maintain a constant reaction temperature. In addition, although varying according to the types of compounds used and reaction temperature, the reaction pressure may be decreased pressure, normal pressure or increased pressure, and the reaction is generally carried out at a pressure within a range of from 20 to $1 \times 10^6$ Pa. There are no particular limitations on the reaction time (residence time in the case of a continuous method) and is generally from 0.001 to 100 hours, preferably from 0.005 to 50 hours and more preferably from 0.01 to 10 hours.

A catalyst is preferably not used in the present embodiment. Although a catalyst may be used to promote the thermal decomposition reaction, there are many cases in which side reactions caused by the aryl carbamate and/or isocyanate product occur easily, thereby making this undesirable.

There are cases in which side reactions as described above may occur in cases of holding the aryl carbamate at high temperatures for an extended period of time. In addition, isocyanates formed by the thermal decomposition reaction may also cause such side reactions. Thus, the time during which the aryl carbamate and the isocyanate are held at a high temperature is preferably as short as possible, and the thermal decomposition reaction is preferably carried out by a continuous process. A continuous process refers to a process in which a mixture containing the aryl carbamate is continuously supplied to a reaction vessel and subjected to the thermal decomposition reaction followed by continuously extracting the isocyanate and aromatic hydroxy compound formed from the thermal decomposition reaction vessel. In this continuous process, a low boiling point component formed by thermal decomposition of the aryl carbamate is preferably recovered from an upper portion of the thermal decomposition reaction vessel in the form of a gaseous phase component, while the remainder is recovered from a bottom of the thermal decomposition reaction vessel in the form of a liquid phase component. Although all compounds present in the thermal decomposition reaction vessel can be recovered in the form of gaseous phase components, by allowing liquid phase components to remain in the thermal decomposition reaction vessel, polymeric compounds formed by side reactions caused by the aryl carbamate and/or isocyanate are dissolved, thereby demonstrating the effect of preventing the polymeric compounds from adhering to and accumulating in the thermal decomposition reaction vessel. Although isocyanate and aromatic hydroxy compound are formed by thermal decomposition of aryl carbamate, at least one of these compounds is recovered in the form of a gaseous phase component. Which of these compounds is recovered in the form of a gaseous phase component depends on the conditions of the thermal decomposition reaction.

Herein, the term "low boiling point component formed by thermal decomposition of aryl carbamate" used in the present embodiment corresponds to the aromatic hydroxy compound and/or isocyanate formed by thermal decomposition of the carbamic acid ester, it particularly refers to compounds able to exist as a gas under the conditions under which the thermal decomposition reaction is carried out.

For example, a method can be employed by which the isocyanate and aromatic hydroxy compound formed by the thermal decomposition reaction are recovered in the form of a gaseous phase component, while a liquid phase component is recovered containing the diaryl carbonate and/or carbamic acid ester. In this method, the isocyanate and aromatic hydroxy compound may be recovered separately in the thermal decomposition reaction vessel. The recovered gaseous phase component containing isocyanate is preferably supplied in the gaseous phase to a distillation apparatus for separation and purification of the isocyanate. Although the recovered gaseous phase component containing isocyanate can be supplied to a distillation apparatus after putting into a liquid phase with a condenser and the like, there are many case in which the apparatus becomes complex and the amount of energy used increases, thereby making this undesirable. On the other hand, the liquid phase component containing the diaryl carbonate and/or aryl carbamate is recovered from the bottom of the thermal decomposition reaction vessel, and in the case the liquid phase component contains diaryl carbonate, the diaryl carbonate is preferably separated and recovered from the liquid phase component and reused. In addition, in the case the liquid phase component contains aryl carbamate, a portion or all of the liquid phase component is preferably supplied to the upper portion of the thermal decomposition reaction vessel, and the aryl carbamate is again subjected to the thermal decomposition reaction. The upper portion of the thermal decomposition reaction vessel as used herein refers to, for example, the second plate and beyond from the bottom in terms of the number of theoretical plates in the case the thermal decomposition reaction vessel is a distillation column, or refers to the portion higher than the heated conductive surface in the case the thermal decomposition reaction vessel is a thin film distiller. When supplying all or a portion of the liquid phase component to the thermal decomposition reaction vessel, the liquid phase component is preferably transported while holding at a temperature of from 50 to 180° C., more preferably from 70 to 170° C. and even more preferably from 100 to 150° C.

In addition, a method can also be employed by which, for example, the isocyanate, aromatic hydroxy compound and diaryl carbonate formed by the thermal decomposition reaction are recovered in the form of a gaseous phase component, and the liquid phase component containing aryl carbamate is recovered from the bottom of the thermal decomposition reaction vessel. In this method as well, the recovered gaseous component containing isocyanate is preferably supplied to a distillation apparatus in the gaseous phase for purification and separation of the isocyanate. On the other hand, all or a portion of the liquid phase component containing aryl carbamate is supplied to the upper portion of the thermal decomposition reaction vessel, and the aryl carbamate is again subjected to the thermal decomposition reaction. When supplying all or a portion of the liquid phase component to the upper portion of the thermal decomposition reaction vessel, the liquid phase component is preferably transported while holding at a temperature of from 50 to 180° C., more preferably from 70 to 170° C. and even more preferably from 100 to 150° C.

Moreover, a method can also be employed by which, for example, the aromatic hydroxy compound of the isocyanate and aromatic hydroxy compound formed by the thermal decomposition reaction is recovered in the form of a gaseous phase component, while a mixture containing the isocyanate is recovered in the form of a liquid phase component from the bottom of the thermal decomposition reaction vessel. In this case, isocyanate is recovered by supplying the liquid phase component to a distillation apparatus. In the case diaryl carbonate is contained in the liquid phase component, the diaryl carbonate is preferably separated and recovered for reuse. In addition, in the case aryl carbamate is contained in the liquid phase component, all of a portion of the mixture containing the aryl carbamate is preferably supplied to the upper portion of the thermal decomposition reaction vessel, and the aryl carbamate is again subjected to the thermal decomposition reaction. When supplying all or a portion of the liquid phase component to the upper portion of the thermal decomposition reaction vessel, the liquid phase component is preferably transported while holding at a temperature of from 50 to 180° C., more preferably from 70 to 170° C. and even more preferably from 100 to 150° C.

Although previously mentioned, in the thermal decomposition reaction, the liquid phase component is preferably recovered from the bottom of the thermal decomposition reaction vessel. This is because, as a result of having the liquid phase component present in the thermal decomposition reaction vessel, polymeric by-products formed by side reactions caused by aryl carbamate and/or isocyanate are dissolved and are able to be discharged from the thermal decomposition reaction vessel in the form of a liquid phase component, thereby having the effect of reducing adhesion and accumulation of these polymeric compounds in the thermal decomposition reaction vessel.

In the case aryl carbamate is contained in the liquid phase component, although all or a portion of the liquid phase component is supplied to the upper portion of the thermal decomposition reaction vessel and the aryl carbamate is re-subjected to the thermal decomposition reaction, there are cases in which polymeric by-products accumulate in the liquid phase component if this step is repeated. In such cases, all or a portion of the liquid phase component can be removed from the reaction system to reduce the accumulation of polymeric by-products or maintain at a constant concentration.

The aromatic hydroxy compound and/or diaryl carbonate contained in the gaseous phase component and/or liquid phase component obtained in the thermal decomposition reaction as described above can each be separated and recovered for reuse. More specifically, the aromatic hydroxy compound can be reused as a reaction solvent in the reaction between diaryl carbonate and amine compound and/or as aromatic hydroxy compound A in step (3) of the production of diaryl carbonate, while the diaryl carbonate can be reused as a raw material in the production of aryl carbamate.

Although there are no particular limitations on the type of thermal decomposition reaction vessel, a known distillation apparatus is used preferably to efficiently recovery the gaseous phase component. Various known methods are used, examples of which may include a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator and types using combinations thereof. From the viewpoint of rapidly removing low boiling point components from the reaction system, a tubular reactor is preferable, while a reaction vessel such as a tubular thin film evaporator, a tubular falling film evaporator is used more preferably, and structures having a large gas-liquid contact area are preferable for being able to rapidly transfer low boiling point components formed to the gaseous phase.

Although known materials may be used for the thermal decomposition reaction vessel and lines provided they do not have a detrimental effect on the aryl carbamate or products in the form of the aromatic hydroxy compound, isocyanate and the like, SUS304, SUS316 or SUS316L and the like can be used preferably since they are inexpensive.

<Cleaning the Thermal Decomposition Reaction Vessel>

In the present embodiment, a reaction liquid containing aryl carbamate obtained by reacting the diaryl carbonate and the amine compound contains polymeric side reaction products as represented by, for example, the above-mentioned formulas (5), (6) and (7). Since these side reaction products easily dissolve in the aromatic hydroxy compound in many cases, they dissolve in the reaction liquid containing the aryl carbamate. However, if the majority of the aromatic hydroxy compound is extracted from the thermal decomposition reaction vessel in the form of a gaseous phase component, there are many cases in which the side reaction products adhered to the thermal decomposition reaction vessel. In addition, although polymeric side reaction products originating from side reactions represented by, for example, the above-mentioned formulas (8), (9) and (10) are formed accompanying the thermal decomposition of the aryl carbamate, there are many cases in which by-products resulting from this thermal decomposition reaction also adhere to the thermal decomposition reaction vessel. If these compounds adhering to the thermal decomposition reaction vessel accumulate to a certain degree, operation of the thermal decomposition reaction vessel becomes impaired, and since there are frequently cases in which this makes long-term operation difficult, it was necessary to perform work consisting of disassembling and cleaning the thermal decomposition reaction vessel.

The inventors of the present invention unexpectedly found that compounds adhered to the thermal decomposition reaction vessel easily dissolve in an acid. On the basis of this finding, in the case high boiling point substances have become adhered to the thermal decomposition reaction vessel, the inventors of the present invention conceived and perfected a method for keeping the inside of the thermal decomposition reaction vessel (and particularly the walls thereof) clean by cleaning the walls of the thermal decomposition reaction vessel with acids to dissolve these high boiling point substances and remove them from the thermal decomposition reaction vessel. Since this method enables the walls of the thermal decomposition reaction vessel to be cleaned without having to disassemble and separately clean the thermal decomposition reaction vessel, the down time of the thermal decomposition reaction vessel can be shortened considerably, thereby resulting in high isocyanate production efficiency.

There are no particular limitations on the acid used for cleaning provided it is able to dissolve the polymeric by-products, and organic acids or inorganic acids may be used, although organic acids are used preferably. Although examples of organic acids used may include carbonic acid, sulfonic acid, sulfinic acid, phenols, enols, thiophenols, imides, oximes and aromatic sulfonamides, carbonic acid and phenols are used preferably. Examples of such compounds may include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (including isomers), octanoic acid (including isomers), nonanoic acid (including isomers), decanoic acid (including isomers), undecanoic acid (including isomers), dodecanoic acid (including isomers), tetradecanoic acid (including isomers), hexadecanoic acid (including isomers), acrylic acid, crotonic acid, isocrotonic acid, vinyl acetate, methacrylic acid, angelic acid, tiglic acid, allyl acetate or undecenoic acid (including isomers); saturated or unsaturated aliphatic dicarboxylic acids such as oxalic acid, malonic acid, succinic acid, glutaric acid, adipic acid, heptanedioic acid (including isomers), octanedioic acid (including isomers), nonanedioic acid (including isomers), decanedioic acid (including isomers), maleic acid, fumaric acid, methylmaleic acid, methylfumaric acid, pentenedioic acid (including isomers), itaconic acid or allylmalonic acid; saturated or unsaturated aliphatic tricarboxylic acid compounds such as 1,2,3-propanetricarboxylic acid, 1,2,3-propenetricarboxylic acid or 2,3-dimethylbutane-1,2,3-tricarboxylic acid; aromatic monocarboxylic acid compounds such as benzoic acid, methylbenzoic acid (including isomers), ethylbenzoic acid (including isomers), propylbenzoic acid (including isomers), dimethylbenzoic acid (including isomers) or trimethylbenzoic acid (including isomers); aromatic dicarboxylic acid compounds such as phthalic acid, isophthalic acid, terephthalic acid or methylisophthalic acid (including isomers); aromatic tricarboxylic acid compounds such as hemimellitic acid, trimellitic acid or trimesinic acid; mono-substituted phenols such as phenol, methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers) or cumylphenol (including isomers); di-substituted phenols such as dimethylphenol (including isomers), diethylphenol (including isomers), dipropylphenol (including isomers), dibutylphenol (including isomers), dipentylphenol (including isomers), dihexylphenol (including isomers), diheptylphenol (including isomers), dioctylphenol (including isomers), dinonylphenol (including isomers), didecylphenol (including isomers), didodecylphenol (including isomers), diphenylphenol (including isomers), diphenoxyphenol (including isomers), dicumylphenol (including isomers), methylethylphenol (including isomers), methylpropylphenol (including isomers), methylbutylphenol (including isomers), methylpentylphenol (including isomers), methylhexylphenol (including isomers), methylheptylphenol (including isomers), methyloctylphenol (including isomers), methylnonylphenol (including isomers), methyldecylphenol (including isomers), methyldodecylphenol (including isomers), methylphenylphenol (including isomers), methylphenoxyphenol (including isomers), methylcumylphenol (including isomers), ethylpropylphenol (including isomers), ethylbutylphenol (including isomers), ethylpentylphenol (including isomers), ethylhexylphenol (including isomers), ethylheptylphenol (including isomers), ethyloctylphenol (including isomers), ethylnonylphenol (including isomers), ethyldecylphenol (including isomers), ethyldodecylphenol (including isomers), ethylphenylphenol (including isomers), ethylphenoxyphenol (including isomers), ethylcumylphenol (including isomers), propylbutylphenol (including isomers), propylpentylphenol (including isomers), propylhexylphenol (including isomers), propylheptylphenol (including isomers), propyloctylphenol (including isomers), propylnonylphenol (including isomers), propyldecylphenol (including isomers), propyldodecylphenol (including isomers), propylphenylphenol (including isomers), propylphenoxyphenol (including isomers), propylcumylphenol (including isomers), butylpentylphenol (including isomers), butylhexylphenol (including isomers), butylheptylphenol (including isomers), butyloctylphenol (including isomers), butylnonylphenol (including isomers), butyldecylphenol (including isomers), butyldodecylphenol (including isomers), butylphenylphenol (including isomers), butylphenoxyphenol (including isomers), butylcumylphenol (including isomers), pentylhexylphenol (including isomers), pentylheptylphenol (including isomers), pentyloctylphenol (including isomers), pentylnonylphenol (including isomers), pentyldecylphenol (including isomers), pentyldodecylphenol (including isomers), pentylphenylphenol (including isomers), pentylphenoxyphenol (including isomers), pentylcumylphenol (including isomers), hexylheptylphenol (including isomers), hexyloctylphenol (including isomers), hexylnonylphenol (including isomers), hexyldecylphenol (including isomers), hexyldodecylphenol (including isomers), hexylphenylphenol (including isomers), hexylphenoxyphenol (including isomers), hexylcumylphenol (including isomers), heptyloctylphenol (including isomers), heptylnonylphenol (including isomers), heptyldecylphenol (including isomers), heptyldodecylphenol (including isomers), heptylphenylphenol (including isomers), heptylphenoxyphenol (including isomers), heptylcumylphenol (including isomers), octylnonylphenol (including isomers), octyldecylphenol (including isomers), octyldodecylphenol (including isomers), octylphenylphenol (including isomers), octylphenoxyphenol (including isomers), octylcumylphenol (including isomers), nonyldecylphenol (including isomers), nonyldodecylphenol (including isomers), nonylphenylphenol (including isomers), nonylphenoxyphenol (including isomers), nonylcumylphenol (including isomers), dodecylphenylphenol (including isomers), dodecylphenoxyphenol (including isomers) or dodecylcumylphenol (including isomers); and, tri-substituted phenols such as trimethylphenol (including isomers), triethylphenol (including isomers), tripropylphenol (including isomers), tributylphenol (including isomers), tripentylphenol (including isomers), trihexylphenol (including isomers), triheptylphenol (including isomers), trioctylphenol (including isomers), trinonylphenol (including isomers), tridecylphenol (including isomers), tridodecylphenol (including isomers), triphenylphenol (including isomers), triphenoxyphenol (including isomers), tricumylphenol (including isomers), dimethylethylphenol (including isomers), dimethylpropylphenol (including isomers), dimethylbutylphenol (including isomers), dimethylpentylphenol (including isomers), dimethylhexylphenol (including isomers), dimethylheptylphenol (including isomers), dimethyloctylphenol (including isomers), dimethylnonylphenol (including isomers), dimethyldecylphenol (including isomers), dimethyldodecylphenol (including isomers), dimethylphenylphenol (including isomers), dimethylphenoxyphenol (including isomers), dimethylcumylphenol (including isomers), diethylmethylphenol (including isomers), diethylpropylphenol (including isomers), diethylbutylphenol (including isomers), diethylpentylphenol (including isomers), diethylhexylphenol (including isomers), diethylheptylphenol (including isomers), diethyloctylphenol (including isomers), diethylnonylphenol (including isomers), diethyldecylphenol (including isomers), diethyldodecylphenol (including isomers), diethylphenylphenol (including isomers), diethylphenoxyphenol (including isomers), diethylcumylphenol (including isomers), dipropylmethylphenol (including isomers), dipropylethylphenol (including isomers), dipropylbutylphenol (including isomers), dipropylpentylphenol (including isomers), dipropylhexylphenol (including isomers), dipropylheptylphenol (including isomers), dipropyloctylphenol (including isomers), dipropylnonylphenol (including isomers), dipropyldecylphenol (including isomers), dipropyldodecylphenol (including isomers), dipropylphenylphenol (including isomers), dipropylphenoxyphenol (including isomers), dipropylcumylphenol (including isomers), dibutylmethylphenol (including isomers), dibutylethylphenol (including isomers), dibutylpropylphenol (including isomers), dibutylpentylphenol (including isomers), dibutylhexylphenol (including isomers), dibutylheptylphenol (including isomers), dibutyloctylphenol (including isomers), dibutylnonylphenol (including isomers), dibutyldecylphenol (including isomers), dibutyldodecylphenol (including isomers), dibutylphenylphenol (including isomers), dibutylphenoxyphenol (including isomers), dibutylcumylphenol (including isomers), dipentylmethylphenol (including isomers), dipentylethylphenol (including isomers), dipentylpropylphenol (including isomers), dipentylbutylphenol (including isomers), dipentylhexylphenol (including isomers), dipentylheptylphenol (including isomers), dipentyloctylphenol (including isomers), dipentylnonylphenol (including isomers), dipentyldecylphenol (including isomers), dipentyldodecylphenol (including isomers), dipentylphenylphenol (including isomers), dipentylphenoxyphenol (including isomers), dipentylcumylphenol (including isomers), dihexylmethylphenol (including isomers), dihexylethylphenol (including isomers), dihexylpropylphenol (including isomers), dihexylbutylphenol (including isomers), dihexylpentylphenol (including isomers), dihexylheptylphenol (including isomers), dihexyloctylphenol (including isomers), dihexylnonylphenol (including isomers), dihexyldecylphenol (including isomers), dihexyldodecylphenol (including isomers), dihexylphenylphenol (including isomers), dihexylphenoxyphenol (including isomers), dihexylcumylphenol (including isomers), diheptylmethylphenol (including isomers), diheptylethylphenol (including isomers), diheptylpropylphenol (including isomers), diheptylbutylphenol (including isomers), diheptylpentylphenol (including isomers), diheptylhexylphenol (including isomers), diheptyloctylphenol (including isomers), diheptylnonylphenol (including isomers), diheptyldecylphenol (including isomers), diheptyldodecylphenol (including isomers), diheptylphenylphenol (including isomers), diheptylphenoxyphenol (including isomers), diheptylcumylphenol (including isomers), diocytylmethylphenol (including isomers), dioctylethylphenol (including isomers), dioctylpropylphenol (including isomers), dioctylbutylphenol (including isomers), dioctylpentylphenol (including isomers), dioctylhexylphenol (including isomers), dioctylheptylphenol (including isomers), dioctylnonylphenol (including isomers), dioctyldecylphenol (including isomers), dioctyldodecylphenol (including isomers), dioctylphenylphenol (including isomers), dioctylphenoxyphenol (including isomers), dioctylcumylphenol (including isomers), dinonylmethylphenol (including isomers), dinonylethylphenol (including isomers), dinonylpropylphenol (including isomers), dinonylbutylphenol (including isomers), dinonylpentylphenol (including isomers), dinonylhexylphenol (including isomers), dinonylheptylphenol (including isomers), dinonyloctylphenol (including isomers), dinonyldecylphenol (including isomers), dinonyldodecylphenol (including isomers), dinonylphenylphenol (including isomers), dinonylphenoxyphenol (including isomers), dinonylcumylphenol (including isomers), didecylmethylphenol (including isomers), didecylethylphenol (including isomers), didecylpropylphenol (including isomers), didecylbutylphenol (including isomers), didecylpentylphenol (including isomers), didecylhexylphenol (including isomers), didecylheptylphenol (including isomers), didecyloctylphenol (including isomers), didecylnonylphenol (including isomers), didecyldodecylphenol (including isomers), didecylphenylphenol (including isomers), didecylphenoxyphenol (including isomers), didecylcumylphenol (including isomers), didodecylmethylphenol (including isomers), didodecylethylphenol (including isomers), didodecylpropylphenol (including isomers), didodecylbutylphenol (including isomers), didodecylpentylphenol (including isomers), didodecylhexylphenol (including isomers), didodecylheptylphenol (including isomers), didodecyloctylphenol (including isomers), didodecylnonylphenol (including isomers), didodecyldecylphenol (including isomers), didodecyldodecylphenol (including isomers), didodecylphenylphenol (including isomers), didodecylphenoxyphenol (including isomers), didodecylcumylphenol (including isomers), diphenylmethylphenol (including isomers), diphenylethylphenol (including isomers), diphenylpropylphenol (including isomers), diphenylbutylphenol (including isomers), diphenylpentylphenol (including isomers), diphenylhexylphenol (including isomers), diphenylheptylphenol (including isomers), diphenyloctylphenol (including isomers), diphenylnonylphenol (including isomers), diphenyldecylphenol (including isomers), diphenyldodecylphenol (including isomers), diphenylphenoxyphenol (including isomers), diphenylcumylphenol (including isomers), diphenoxymethylphenol (including isomers), diphenoxyethylphenol (including isomers), diphenoxypropylphenol (including isomers), diphenoxybutylphenol (including isomers), diphenoxypentylphenol (including isomers), diphenoxyhexylphenol (including isomers), diphenoxyheptylphenol (including isomers), diphenoxyoctylphenol (including isomers), diphenoxynonylphenol (including isomers), diphenoxydecylphenol (including isomers), diphenoxydodecylphenol (including isomers), diphenoxyphenylphenol (including isomers), diphenoxycumylphenol (including isomers), dicumylmethylphenol (including isomers), dicumylethylphenol (including isomers), dicumylpropylphenol (including isomers), dicumylbutylphenol (including isomers), dicumylpentylphenol (including isomers), dicumylhexylphenol (including isomers), dicumylheptylphenol (including isomers), dicumyloctylphenol (including isomers), dicumylnonylphenol (including isomers), dicumyldecylphenol (including isomers), dicumyldodecylphenol (including isomers), dicumylphenylphenol (including isomers), dicumylphenoxyphenol (including isomers), methylethylpropylphenol (including isomers), methylethylbutylphenol (including isomers), methylethylpentylphenol (including isomers), methylethylhexylphenol (including isomers), methylethylheptylphenol (including isomers), methylethyloctylphenol (including isomers), methylethylnonylphenol (including isomers), methylethyldecylphenol (including isomers), methylethyldodecylphenol (including isomers), methylethylphenylphenol (including isomers), methylethylphenoxyphenol (including isomers), methylethylcumylphenol (including isomers), methylpropylbutylphenol (including isomers), methylpropylpentylphenol (including isomers), methylpropylhexylphenol (including isomers), methylpropylheptylphenol (including isomers), methylpropyloctylphenol (including isomers), methylpropylnonylphenol (including isomers), methylpropyldecylphenol (including isomers), methylpropyldodecylphenol (including isomers), methylpropylphenylphenol (including isomers), methylpropylphenoxyphenol (including isomers), methylpropylcumylphenol (including isomers), methylbutylpentylphenol (including isomers), methylbutylhexylphenol (including isomers), methylbutylheptylphenol (including isomers), methylbutyloctylphenol (including isomers), methylbutylnonylphenol (including isomers), methylbutyldecylphenol (including isomers), methylbutyldodecylphenol (including isomers), methylbutylphenylphenol (including isomers), methylbutylphenoxyphenol (including isomers), methylbutylcumylphenol (including isomers), methylpentylhexylphenol, methylpentylheptylphenol (including isomers), methylpentyloctylphenol (including isomers), methylpentylnonylphenol (including isomers), methylpentyldecylphenol (including isomers), methylpentyldodecylphenol (including isomers), methylpentylphenylphenol (including isomers), methylpentylphenoxyphenol (including isomers), methylpentylcumylphenol (including isomers), methylhexylheptylphenol (including isomers), methylhexyloctylphenol (including isomers), methylhexylnonylphenol (including isomers), methylhexyldecylphenol (including isomers), methylhexyldodecylphenol (including isomers), methylhexylphenylphenol (including isomers), methylhexylphenoxyphenol (including isomers), methylhexylcumylphenol (including isomers), ethylpropylbutylphenol (including isomers), ethylpropylpentylphenol (including isomers), ethylpropylhexylphenol (including isomers), ethylpropylheptylphenol (including isomers), ethylpropyloctyl phenol (including isomers), ethylpropylnonylphenol (including isomers), ethylpropyldecylphenol (including isomers), ethylpropyldodecylphenol (including isomers), ethylpropylphenylphenol (including isomers), ethylpropylphenoxyphenol (including isomers), ethylpropylcumylphenol (including isomers), ethylbutylphenol (including isomers), ethylbutylpentylphenol (including isomers), ethylbutylhexylphenol (including isomers), ethylbutylheptylphenol (including isomers), ethylbutyloctylphenol (including isomers), ethylbutylnonylphenol (including isomers), ethylbutyldecylphenol (including isomers), ethylbutyldodecylphenol (including isomers), ethylbutylphenylphenol (including isomers), ethylbutylphenoxyphenol (including isomers), ethylbutylcumylphenol (including isomers), ethylpentylhexylphenol (including isomers), ethylpentylheptylphenol (including isomers), ethylpentyloctylphenol (including isomers), ethylpentylnonylphenol (including isomers), ethylpentyldecylphenol (including isomers), ethylpentyldodecylphenol (including isomers), ethylpentylphenylphenol (including isomers), ethylpentylphenoxyphenol (including isomers), ethylpentylcumylphenol (including isomers), ethylhexylheptylphenol (including isomers), ethylhexyloctylphenol (including isomers), ethylhexylnonylphenol (including isomers), ethylhexyldecylphenol (including isomers), ethylhexyldodecylphenol (including isomers), ethylhexylphenylphenol (including isomers), ethylhexylphenoxyphenol (including isomers), ethylhexylcumylphenol (including isomers), ethylheptyloctylphenol (including isomers), ethylheptylnonylphenol (including isomers), ethylheptyldecylphenol (including isomers), ethylheptyldodecylphenol (including isomers), ethylheptylphenylphenol (including isomers), ethylheptylphenoxyphenol (including isomers), ethylheptylcumylphenol (including isomers), ethyloctylphenol (including isomers), ethyloctylnonylphenol (including isomers), ethylocyldecylphenol (including isomers), ethyloctyldodecylphenol (including isomers), ethyloctylphenylphenol (including isomers), ethyloctylphenoxyphenol (including isomers), ethyloctylcumylphenol (including isomers), ethylnonyldecylphenol (including isomers), ethylnonyldodecylphenol (including isomers), ethylnonylphenylphenol (including isomers), ethylnonylphenoxyphenol (including isomers), ethylnonylcumylphenol (including isomers), ethyldecyldodecylphenol (including isomers), ethyldecylphenylphenol (including isomers), ethyldecylphenoxyphenol (including isomers), ethyldecylcumylphenol (including isomers), ethyldodecylphenylphenol (including isomers), ethyldodecylphenoxyphenol (including isomers), ethyldodecylcumylphenol (including isomers), ethylphenylphenoxyphenol (including isomers), ethylphenylcumylphenol (including isomers), propylbutylphenol (including isomers), propylbutylpentylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpentylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propylhexylphenol (including isomers), propylhexylheptylphenol (including isomers), propylhexyloctylphenol (including isomers), propylhexylnonylphenol (including isomers), propylhexyldecylphenol (including isomers), propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptyldecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), propyloctylphenoxyphenol (including isomers), propyloctylcumylphenol (including isomers), propylnonyldecylphenol (including isomers), propylnonyldodecylphenol (including isomers), propylnonylphenylphenol (including isomers), propylnonylphenoxyphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propyldodecylphenoxyphenol (including isomers), propyldodecylcumylphenol (including isomers), methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers), cumylphenol (including isomers), propylphenylphenoxyphenol (including isomers), propylphenylcumylphenol (including isomers), propylphenoxycumylphenol (including isomers), propylbutylpentylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpentylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propylhexylheptylphenol (including isomers), propylhexyloctylphenol (including isomers), propylhexylnonylphenol (including isomers), propylhexyldecylphenol (including isomers), propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptyldecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), propyloctylphenoxyphenol (including isomers), propyloctylcumylphenol (including isomers), propylnonyldecylphenol (including isomers), propylnonyldodecylphenol (including isomers), propylnonylphenylphenol (including isomers), propylnonylphenoxyphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propyldodecylphenoxyphenol (including isomers), propylphenylphenoxyphenol (including isomers), propylphenylcumylphenol (including isomers), butylpentylhexylphenol (including isomers), butylpentylheptylphenol (including isomers), butylpentyloctylphenol (including isomers), butylpentylnonylphenol (including isomers), butylpentyldecylphenol (including isomers), butylpentyldodecylphenol (including isomers), butylpentylphenylphenol (including isomers), butylpentylphenoxyphenol (including isomers), butylpentylcumylphenol (including isomers), butylhexylheptylphenol (including isomers), butylhexyloctylphenol (including isomers), butylhexylnonylphenol (including isomers), butylhexyldecylphenol (including isomers), butylhexyldodecylphenol (including isomers), butylhexylphenylphenol (including isomers), butylhexylphenoxyphenol (including isomers), butylhexylcumylphenol (including isomers), butylheptyloctylphenol (including isomers), butylheptylnonylphenol (including isomers), butylheptyldecylphenol (including isomers), butylheptyldodecylphenol (including isomers), butylheptylphenylphenol (including isomers), butylheptylphenoxyphenol (including isomers), butylheptylcumylphenol (including isomers), butyloctylnonylphenol (including isomers), butyloctyldecylphenol (including isomers), butyloctyldodecylphenol (including isomers), butyloctylphenylphenol (including isomers), butyloctylphenoxyphenol (including isomers), butyloctylcumylphenol (including isomers), butylnonyldecylphenol (including isomers), butylnonyldodecylphenol (including isomers), butylnonylphenylphenol (including isomers), butylnonylphenoxyphenol (including isomers), butylnonylcumylphenol (including isomers), butyldecyldodecylphenol (including isomers), butyldecylphenylphenol (including isomers), butyldecylphenoxyphenol (including isomers), butyldecylcumylphenol (including isomers), butyldodecylphenol (including isomers), butyldodecylphenylphenol (including isomers), butyldodecylphenoxyphenol (including isomers), butyldodecylcumylphenol (including isomers), butylphenylphenol (including isomers), butylphenylphenoxyphenol (including isomers), butylphenylcumylphenol (including isomers), pentylhexylheptylphenol (including isomers), pentylhexyloctylphenol (including isomers), pentylhexylnonylphenol (including isomers), pentylhexyldecylphenol (including isomers), pentylhexyldodecylphenol (including isomers), pentylhexylphenylphenol (including isomers), pentylhexylphenoxyphenol (including isomers), pentylhexylcumylphenol (including isomers), pentylhetpyloctylphenol (including isomers), pentylheptylnonylphenol (including isomers), pentylheptyldecylphenol (including isomers), pentylheptyldodecylphenol (including isomers), pentylheptylphenylphenol (including isomers), pentylheptylphenoxyphenol (including isomers), pentylheptylcumylphenol (including isomers), pentyloctylnonylphenol (including isomers), pentyloctyldecylphenol (including isomers), pentyloctyldodecylphenol (including isomers), pentyloctylphenylphenol (including isomers), pentyloctylphenoxyphenol (including isomers), pentyloctylcumylphenol (including isomers), pentylnonyldecylphenol (including isomers), pentylnonyldodecylphenol (including isomers), pentylnonylphenylphenol (including isomers), pentylnonylphenoxyphenol (including isomers), pentylnonylcumylphenol (including isomers), pentyldecyldodecylphenol (including isomers), pentyldecylphenylphenol (including isomers), pentyldecylphenoxyphenol (including isomers), pentyldecylcumylphenol (including isomers), pentyldodecylphenylphenol (including isomers), pentyldodecylphenoxyphenol (including isomers), pentyldodecylcumylphenol (including isomers), pentylphenylphenoxyphenol (including isomers), pentylphenylcumylphenol (including isomers), hexylheptyloctylphenol (including isomers), hexylheptylnonylphenol (including isomers), hexylheptyldecylphenol (including isomers), hexylheptyldodecylphenol (including isomers), hexylheptylphenylphenol (including isomers), hexylheptylphenoxyphenol (including isomers), hexylheptylcumylphenol (including isomers), hexyloctylnonylphenol (including isomers), hexyloctyldecylphenol (including isomers), hexyloctyldodecylphenol (including isomers), hexyloctylphenylphenol (including isomers), hexyloctylphenoxyphenol (including isomers), hexyloctylcumylphenol (including isomers), hexylnonyldecylphenol (including isomers), hexylnonyldodecylphenol (including isomers), hexylnonylphenylphenol (including isomers), hexylnonylphenoxyphenol (including isomers), hexyldecylphenylphenol (including isomers), hexyldecylphenoxyphenol (including isomers), hexyldecylcumylphenol (including isomers), hexyldodecylphenylphenol (including isomers), hexyldodecylphenoxyphenol (including isomers), hexyldodecylcumylphenol (including isomers), hexylphenylphenoxyphenol (including isomers), hexylphenylcumylphenol (including isomers), heptyloctylnonylphenol (including isomers), heptyloctyldecylphenol (including isomers), heptyloctyldodecylphenol (including isomers), heptyloctylphenylphenol (including isomers), heptyloctylphenoxyphenol (including isomers), heptyloctylcumylphenol (including isomers), heptylnonyldecylphenol (including isomers), heptylnonyldodecylphenol (including isomers), heptylnonylphenylphenol (including isomers), heptylnonylphenoxyphenol (including isomers), heptylnonylcumylphenol (including isomers), heptyldecyldodecylphenol (including isomers), heptyldecylphenylphenol (including isomers), heptyldecylphenoxyphenol (including isomers), heptyldecylcumylphenol (including isomers), heptyldodecylphenylphenol (including isomers), heptyldodecylphenoxyphenol (including isomers), heptyldodecylcumylphenol (including isomers), heptylphenylphenoxyphenol (including isomers), heptylphenylcumylphenol (including isomers), octylnonyldecylphenol (including isomers), octylnonyldodecylphenol (including isomers), octylnonylphenylphenol (including isomers), octylnonylphenoxyphenol (including isomers), octylnonylcumylphenol (including isomers), octyldecyldodecylphenol (including isomers), octyldecylphenylphenol (including isomers), octyldecylphenoxyphenol (including isomers), octyldecylcumylphenol (including isomers), octyldodecylphenylphenol (including isomers), octyldodecylphenoxyphenol (including isomers), octyldodecylcumylphenol (including isomers), octylphenylphenoxyphenol (including isomers), octylphenylcumylphenol (including isomers), nonyldecyldodecylphenol (including isomers), nonyldecylphenylphenol (including isomers), nonyldecylphenoxyphenol (including isomers), nonyldecylcumylphenol (including isomers), nonyldodecylphenylphenol (including isomers), nonyldodecylphenoxyphenol (including isomers), nonyldodecylcumylphenol (including isomers), nonylphenylphenoxyphenol (including isomers), nonylphenylcumylphenol (including isomers), decyldodecylphenylphenol (including isomers), decyldodecylphenoxyphenol (including isomers), decyldodecylcumylphenol (including isomers), decylphenylphenoxyphenol (including isomers), decylphenylcumylphenol (including isomers), dodecylphenylphenoxyphenol (including isomers), dodecylphenylcumylphenol (including isomers) or phenylphenoxycumylphenol (including isomers). Among these organic acids, in consideration of effects in the case of the cleaning solvent remaining in the thermal decomposition reaction vessel following the cleaning procedure, aromatic hydroxy compounds are more preferable, while compounds similar to the aromatic hydroxy compound used in the reaction between diaryl carbonate and amine compound are even more preferable.

Note that in the case of using the aromatic hydroxy compound for the acid used during cleaning, the difference between the standard boiling point of the aromatic hydroxy compound and the standard boiling points of the compound corresponding to the isocyanate formed by the previously described thermal decomposition of the aryl carbamate and the aromatic hydroxy compound formed by thermal decomposition of the aryl carbamate is preferably 10° C. or more from the viewpoint of cleaning effects.

Various methods can be used to clean the thermal decomposition reaction vessel using the above cleaning solvent, examples of which may include cleaning the thermal decomposition reaction vessel by introducing the cleaning solvent from the upper portion of the thermal decomposition reaction vessel, and cleaning the inside of the thermal decomposition reaction vessel by introducing the cleaning solvent from the bottom of the thermal decomposition reaction vessel and boiling it inside the thermal decomposition reaction vessel.

It is not necessary to carry out the cleaning procedure each time the thermal decomposition reaction is carried out, but rather the cleaning frequency can be arbitrarily determined according to the compounds used, operating rate and so forth, and the cleaning procedure is preferably carried out once every 1 to 20000 hours of operation, more preferably once per one day to one year of operating time, and even more preferably once per one month to one year of operating time. The thermal decomposition reaction vessel may be provided with a line for introducing the cleaning solvent.

In addition, when carrying out thermal decomposition of aryl carbamate for the purpose of cleaning the thermal decomposition reaction vessel, the cleaning solvent can also be present in the conditions of the thermal decomposition reaction. This differs from the inert solvent as referred to in the prior art (see, for example, U.S. Pat. No. 4,081,472). For example, according to this patent document, although an inert solvent refers to a compound that does not react with isocyanate formed by thermal decomposition of carbamic acid ester, in contrast thereto, as stated in the literature (Journal of the American Chemical Society, Vol. 64, p. 2229, 1942), for example, that urethane is formed by a reaction between an aromatic hydroxy compound and phenyl isocyanate, aromatic hydroxy compounds are able to react with isocyanates. The aromatic hydroxy compound may be transferred to the thermal decomposition reaction vessel after mixing when transferring the reaction mixture obtained by a reaction between diaryl carbonate and an amine compound to the thermal decomposition reaction vessel, or may be supplied by providing a line for supplying the aromatic hydroxy compound separate from the line for supplying the reaction mixture.

The isocyanates obtained by the production process according to the present embodiment can be preferably used as a production raw material of polyurethane foam, paints, adhesives and the like. Since isocyanates can be produced according to the production process of the present embodiment in good yield without using toxic phosgene, the present invention is industrially extremely important.

EXAMPLES

Although the following provides a detailed explanation of the present invention based on examples thereof, the scope of the present invention is not limited by these examples.

<Analytical Methods>
1) NMR Analysis
  Apparatus: JNM-A400 FT-NMR system, JEOL Ltd., Japan
  (1) Preparation of $^1$H- and $^{13}$C-NMR Analysis Samples
    About 0.3 g of sample solution were weighed followed by the addition of about 0.7 g of heavy chloroform (99.8%, Aldrich Corp., USA) and 0.05 g of tetramethyl tin (guaranteed reagent, Wako Pure Chemical Industries, Ltd., Japan) as an internal standard and mixing to uniformity to obtain solutions used as NMR analysis samples.
  (2) Quantitative Analysis
    Analyses were performed for each standard and quantitative analyses were performed on the analysis sample solutions based on the resulting calibration curve.
2) Liquid Chromatography
  Apparatus: LC-10AT system, Shimadzu Corp., Japan
  Column: Silica-60 column, Tosoh Corp., Japan, two columns connected in series
  Developing solvent: Mixed liquid of hexane/tetrahydrofuran (80/20) (v/v)
  Solvent flow rate: 2 mL/min
  Column temperature: 35° C.
  Detector: R.I. (refractometer)
  (1) Liquid Chromatography Analysis Samples
    About 0.1 g of sample were weighed followed by the addition of about 1 g of tetrahydrofuran (dehydrated, Wako Pure Chemical Industries, Ltd., Japan) and about 0.02 g of bisphenol A (guaranteed reagent, Wako Pure Chemical Industries, Ltd., Japan) as an internal standard and mixing to uniformity to obtain solutions used as liquid chromatography analysis samples.
  (2) Quantitative Analysis
    Analyses were performed for each standard and quantitative analyses were performed on the analysis sample solutions based on the resulting calibration curve.
3) Gas Chromatography
  Apparatus: GC-2010, Shimadzu Corp., Japan
  Column: DB-1 column, Agilent Technologies Corp., USA, length: 30 m, inner diameter: 0.250 mm, film thickness: 1.00 μm
  Column temperature: Held at 50° C. for 5 minutes followed by increasing at the rate of 10° C./min to 200° C.; held at 200° C. for 5 minutes followed by increasing at the rate of 10° C./min to 300° C.
  Detector: FID
  (1) Gas Chromatography Analysis Samples
    About 0.05 g of sample were weighed followed by the addition of about 1 g of acetone (dehydrated, Wako Pure Chemical Industries, Ltd., Japan) and about 0.02 g of toluene (dehydrated, Wako Pure Chemical Industries, Ltd., Japan) as an internal standard and mixing to uniformity to obtain solutions used as gas chromatography analysis samples.
  (2) Quantitative Analysis
    Analyses were performed for each standard and quantitative analyses were performed on the analysis sample solutions based on the resulting calibration curve.
4) Inductively Coupled Plasma Mass Spectrometry
  Apparatus: SPQ-8000, Seiko Epson Corp., Japan
  (1) Inductively Coupled Plasma Mass Spectrometry Analysis Samples
    About 0.15 g of sample was ashed with dilute sulfuric acid followed by dissolving in dilute nitric acid.
  (2) Quantitative Analysis
    Analyses were performed for each standard and quantitative analyses were performed on the analysis sample solutions based on the resulting calibration curve.

Reference Example 1

Production of Diphenyl Carbonate

Step (I-1): Production of Dialkyl Tin Catalysts 692 g (2.78 mol) of di-n-butyl tin oxide and 2000 g (27 mol) of 1-butanol (Wako Pure Chemical Industries, Ltd., Japan) were placed in a 3000 mL volumetric pear-shaped flask. The flask containing the mixture in the form of a white slurry was connected to an evaporator to which was connected an oil bath equipped with a temperature controller, a vacuum pump and a vacuum controller. The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to be 126° C., the flask was immersed in the oil bath and rotation of the evaporator was started. After heating and stirring by rotation for about 30 minutes at normal pressure with the purge valve of the evaporator left open, the mixture boiled and distillation of low boiling point components began. After maintaining in this state for 8 hours, the purge valve was closed, pressure inside the system was gradually reduced, and residual low boiling point components were distilled with the pressure inside the system at 76 to 54 kPa. After the low boiling point components no longer appeared, the flask was taken out of the oil bath. The reaction liquid was in the form of a clear liquid. Subsequently, the flask was taken out of the oil bath, the purge valve was opened gradually and the pressure inside the system was returned to normal pressure. 952 g of reaction liquid were obtained in the flask. Based on the results of $^{119}$Sn-, $^1$H- and $^{13}$C-NMR analyses, a product in a form of 1,1,3,3-tetra-n-butyl-1,3-di(n-butyloxy) distannoxane was obtained at a yield of 99% based on di-n-butyl tin oxide. The same procedure was then repeated 12 times to obtain a total of 11480 g of 1,1,3,3-tetra-n-butyl-1,3-di(n-butyloxy) distannoxane.

Step (I-2): Production of Dibutyl Carbonate

Figure 1:
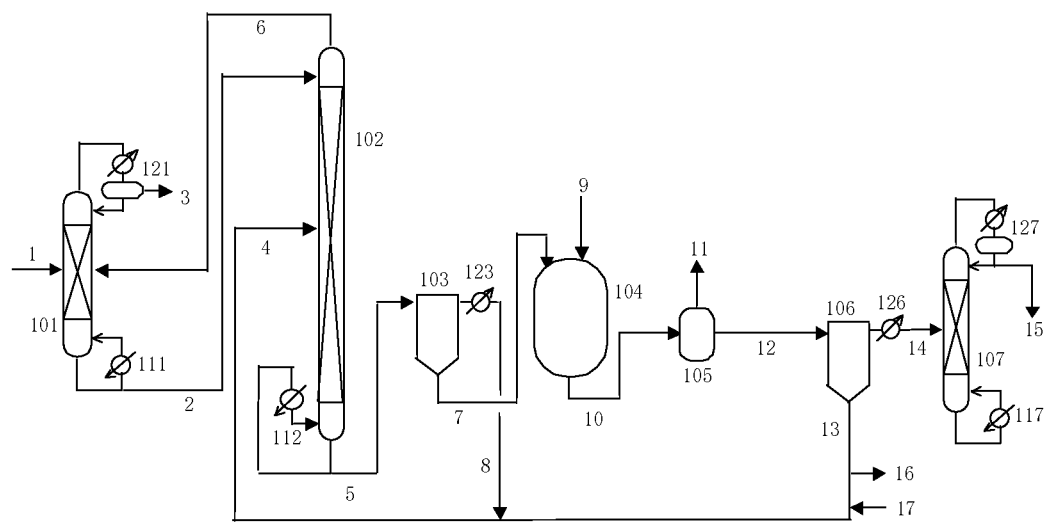
FIG. 1 is a conceptual drawing showing a continuous production apparatus for producing carbonic acid ester according to an embodiment of the present invention.

Carbonic acid ester was produced in a continuous production apparatus like that shown in FIG. 1. 1,1,3,3-tetra-n-butyl-1,3-di(n-butyloxy) distannoxane produced in step (1-1) was supplied at the rate of 4201 g/hr from a line 4 into a column-type reaction vessel packed with Mellapak 750Y (Sulzer Chemtech Ltd., Switzerland) and having an inner diameter of 151 mm and effective length of 5040 mm, and 1-butanol purified with distillation column 101 was supplied to column-type reaction vessel 102 at the rate of 24717 g/hr from line 2. The liquid temperature inside reaction vessel was controlled to 160° C. by a heater and reboiler 112, and the pressure was adjusted to about 150 kPa-G with a pressure control valve. The residence time in the reaction vessel was about 10 minutes. 1-Butanol containing water at the rate of 24715 g/hr from the top of the reaction vessel via line 6, and 1-butanol at the rate of 824 g/hr via line 1, were pumped to distillation column 101 packed with Metal Gauze CY Packing (Sulzer Chemtech Ltd., Switzerland) and provided with reboiler 111 and condenser 121 to carry out distillative purification. In the top of distillation column 101, a fraction containing a high concentration of water was condensed by condenser 121 and recovered from line 3. Purified 1-butanol was pumped via transfer line 2 located in the bottom of distillation column 101. An alkyl tin alkoxide catalyst composition containing di-n-butyl tin di-n-butoxide and 1,1,3,3-tetra-n-butyl-1,3-di (n-butyloxy) distannoxane was obtained from the bottom of column-type reaction vessel 102, and supplied to thin film evaporator 103 (Kobelco Eco-Solutions Co., Ltd., Japan) via line 5. The 1-butanol was distilled off in thin film evaporator 103 and returned to column-type reaction vessel 102 via condenser 123, line 8 and line 4. The alkyl tin alkoxide catalyst composition was pumped from the bottom of thin film evaporator 103 via line 7 and supplied to autoclave 104 while adjusting the flow rate of the active components in the form of dibutyl tin dibutoxide and 1,1,3,3-tetra-n-butyl-1,3-di(n-butyloxy) distannoxane to about 4812 g/hr. Carbon dioxide was supplied to the autoclave by line 9 at the rate of 973 g/hr, and the pressure inside the autoclave was maintained at 4 MPa-G. The temperature inside the autoclave was set to be 120° C., the residence time was adjusted to about 4 hours, and a reaction between the carbon dioxide and the alkyl tin alkoxide catalyst composition was carried out to obtain a reaction liquid containing dibutyl carbonate. This reaction liquid was transferred to decarbonization tank 105 via line 10 and a control valve to remove residual carbon dioxide, and the carbon dioxide was recovered from line 11. Subsequently, the reaction liquid was pumped to thin film evaporator 106 (Kobelco Eco-Solutions Co., Ltd., Japan) set to be 140° C. and about 1.4 kPa via line 12 and supplied while adjusting the flow rate of 1,1,3,3-tetra-n-butyl-1,3-di(n-butyloxy) distannoxane to about 4201 g/hr to obtain a fraction containing dibutyl carbonate. On the other hand, the evaporation residue was circulated to column-type reaction vessel 102 via line 13 and line 4 while adjusting the flow rate of 1,1,3,3-tetra-n-butyl-1,3-di(n-butyloxy) distannoxane to about 4201 g/hr. The fraction containing dibutyl carbonate was supplied to distillation column 107 packed with Metal Gauze CY packing (Sulzer Chemtech Ltd., Switzerland) and equipped with reboiler 117 and condenser 127 via condenser 126 and line 14 at the rate of 830 g/hr followed by distillative purification to obtain 99 wt % dibutyl carbonate from line 15 at the rate of 814 g/hr. When the alkyl tin alkoxide catalyst composition of line 13 was analyzed by $^{119}$Sn-, $^{1}$H- and $^{13}$C-NMR analysis, it was found to contain 1,1,3,3-tetra-n-butyl-1,3-di(n-butyloxy) distannoxane but not contain di-n-butyl tin-di-n-butoxide. After carrying out the above-mentioned continuous operation for about 600 hours, alkyl tin alkoxide catalyst composition was extracted from line 16 at the rate of 16 g/hr, while 1,1,3,3-tetra-n-butyl-1,3-di(n-butyloxy) distannoxane produced according to step (1-1) was supplied from line 17 at the rate of 16 g/hr.

Step (I-3): Production of Aromatic Carbonic Acid Ester

[Catalyst Preparation]

79 g of phenol and 32 g of lead oxide were heated for 10 hours at 180° C. and water formed was distilled off with the phenol. About 2.5 g of water were extracted in 10 hours. Subsequently, the catalyst was prepared by distilling off phenol from the top of the reaction vessel.

[Production of Aromatic Carbonic Acid Ester]

Figure 2:
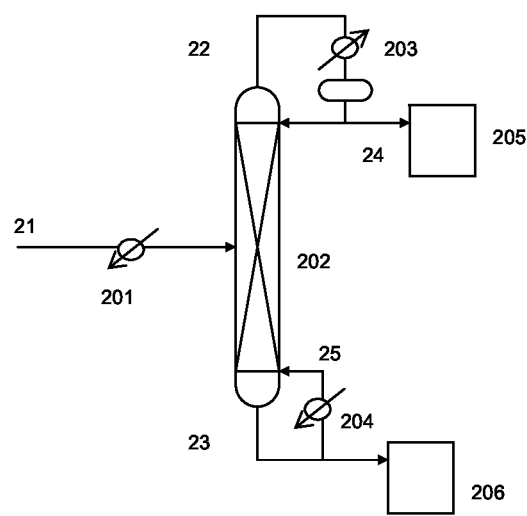
FIG. 2 is a conceptual drawing showing an aromatic carbonic acid ester production apparatus according to an embodiment of the present invention.

An apparatus like that shown in FIG. 2 was used.

A mixture comprising the dibutyl carbonate obtained in step (I-2), phenol and the catalyst prepared above (adjusted so that the weight ratio of dibutyl carbonate and phenol in the mixture was about 65/35 and the lead concentration was about 1% by weight) was continuously fed in a liquid state through preheater 201 to the middle stage of continuous multistage distillation column 202 packed with Dickson packing (diameter: 6 mm) and having an inner diameter of about 5 cm and column length of 2 m from line 21 at the rate of about 270 g/hr and allowed to react. The amount of heat required for the reaction and distillation was supplied by circulating the liquid in the bottom of the column through line 23 and reboiler 204. The liquid temperature in the bottom of the continuous multistage distillation column 202 was 238° C., the pressure at the top of the column was about 250 kPa, and the reflux ratio was set to be about 2. Gas distilled from the top of continuous multistage distillation column 202 was extracted from line 22, and continuously extracted into storage tank 205 through condenser 203 from line 24 at the rate of about 67 g/hr. Liquid was continuously extracted from the bottom of the column through line 23 into storage tank 206 at the rate of about 204 g/hr.

The composition of the liquid extracted from line 24 consisted of about 33% by weight of 1-butanol, about 65% by weight of phenol and about 2% by weight of dibutyl carbonate. The composition of the liquid extracted to storage tank 206 consisted of about 11% by weight of phenol, about 60% by weight of dibutyl carbonate, about 26% by weight of butylphenyl carbonate, and about 1.6% by weight of diphenyl carbonate, and the lead concentration was about 1% by weight.

Figure 3:
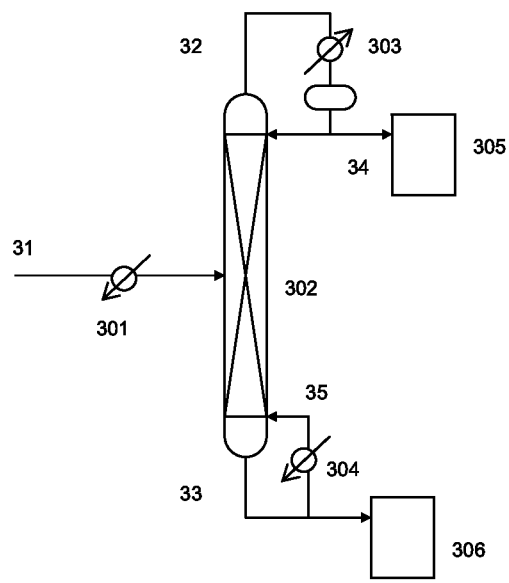
FIG. 3 is a conceptual drawing showing an aromatic carbonic acid ester production apparatus according to an embodiment of the present invention.

Next, an apparatus like that shown in FIG. 3 was used.

Liquid extracted into storage tank 206 was continuously fed in a liquid state through preheater 301 to the middle stage of continuous multistage distillation column 302 packed with Dickson packing (diameter: 6 mm) and having an inner diameter of about 5 cm and column length of 2 m from line 31 at the rate of about 203 g/hr. The amount of heat required for the reaction and distillation was supplied by circulating the liquid in the bottom of the column through line 33 and reboiler 304. The liquid temperature in the bottom of continuous multistage distillation column 302 was 240° C., the pressure at the top of the column was about 27 kPa, and the reflux ratio was set to be about 2. Gas distilled from the top of continuous multistage distillation column 302 was condensed in a condenser 303 via line 32 and continuously extracted from line 34 into storage tank 305 at the rate of about 165 g/hr. Liquid was continuously extracted from the bottom of the column through line 33 into storage tank 306 at the rate of about 39 g/hr.

The composition of the liquid extracted from line 34 consisted of about 500 ppm of 1-butanol, about 13% by weight of phenol, about 85% by weight of dibutyl carbonate and about 2% by weight of butylphenyl carbonate. The composition of the liquid extracted to storage tank 306 consisted of about 0.3% by weight of dibutyl carbonate, about 32% by weight of butylphenyl carbonate, and about 61% by weight of diphenyl carbonate, and the lead concentration was about 7% by weight.

[Recycling of Alcohol]

Figure 4:
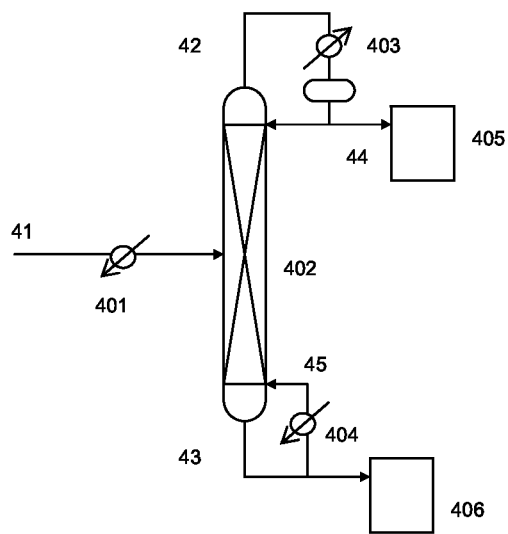
FIG. 4 is a conceptual drawing showing an alcohol purification apparatus according to an embodiment of the present invention.

Alcohol was recycled using an apparatus like that shown in FIG. 4.

Liquid continuously extracted into storage tank 205 was continuously fed through preheater 401 to a position of about 0.7 m from the bottom of continuous multistage distillation column 402 packed with Dickson packing (diameter: 6 mm) and having an inner diameter of about 5 cm and column length of 2 m from line 41 at the rate of about 201 g/hr to carry out distillative separation. The amount of heat required for the distillative separation was supplied by circulating the liquid in the bottom of the column through line 43 and reboiler 404. The liquid temperature in the bottom of continuous multistage distillation column 402 was 145° C., the pressure at the top of the column was about 13 kPa, and the reflux ratio was set to be about 0.3. Gas distilled from the top of continuous multistage distillation column 402 was condensed in condenser 403 via line 42 and extracted from line 44 into storage tank 405 at the rate of about 68 g/hr. Liquid was continuously extracted from the bottom of the column through line 43 into storage tank 406 at the rate of about 133 g/hr.

The composition of the liquid extracted from line 44 consisted of about 99% by weight of 1-butanol and about 100 ppm of phenol. The composition of the liquid extracted to storage tank 406 consisted of about 2% by weight of dibutyl carbonate and about 98% by weight of phenol.

[Purification of Diaryl Carbonate]

Figure 5:
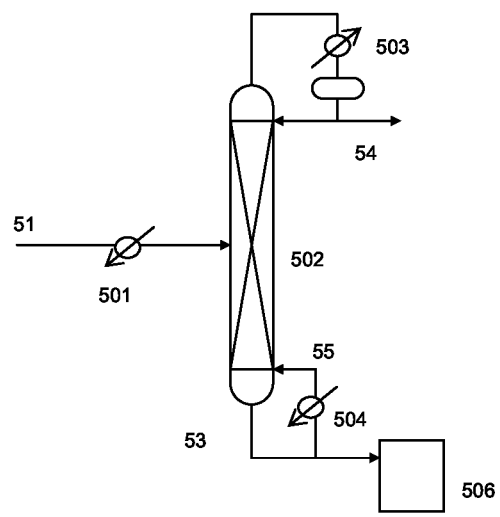
FIG. 5 is a conceptual drawing showing a diaryl carbonate purification apparatus according to an embodiment of the present invention.
Figure 6:
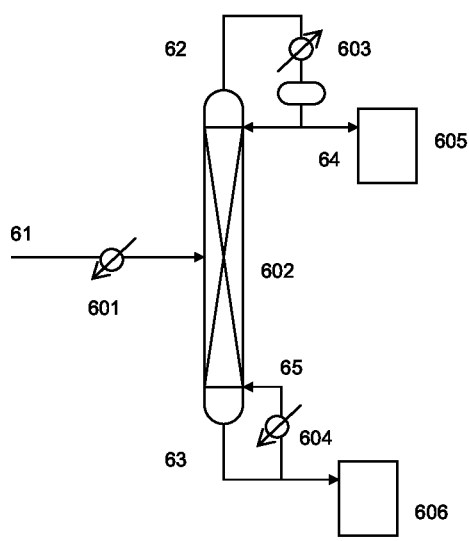
FIG. 6 is a conceptual drawing showing a diaryl carbonate purification apparatus according to an embodiment of the present invention.

Diaryl carbonate was purified using an apparatus like that shown in FIGS. 5 and 6.

Liquid extracted to storage tank 306 was continuously fed in a liquid state through preheater 501 to the middle stage of continuous multistage distillation column 502 packed with Dickson packing (diameter: 6 mm) and having an inner diameter of about 5 cm and column length of 2 m from line 51 at the rate of about 195 g/hr. The amount of heat required for distillative separation was supplied by circulating the liquid in the bottom of the column through line 53 and reboiler 504. The liquid temperature in the bottom of the continuous multistage distillation column 502 was 210° C., the pressure at the top of the column was about 1.5 kPa, and the reflux ratio was set to be about 1. Gas distilled from the top of continuous multistage distillation column 502 was condensed in a condenser 503 via line 52, and continuously extracted from line 54. Liquid was extracted from the bottom of the column through line 53 into storage tank 506 at the rate of about 14 g/hr.

The composition of the liquid extracted from line 54 consisted of about 0.3% by weight of dibutyl carbonate, about 34% by weight of butylphenyl carbonate and about 66% by weight of diphenyl carbonate.

Liquid extracted from line 54 was continuously fed through preheater 601 to the middle stage of continuous multistage distillation column 602 packed with Dickson packing (diameter: 6 mm) and having an inner diameter of about 5 cm and column length of 2 m from line 61 at the rate of about 181 g/hr. The amount of heat required for distillative separation was supplied by circulating the liquid in the bottom of the column through line 63 and reboiler 604. The liquid temperature in the bottom of continuous multistage distillation column 602 was 232° C., the pressure at the top of the column was about 15 kPa, and the reflux ratio was set to be about 2. Gas distilled from the top of continuous multistage distillation column 602 was condensed in condenser 603 via line 62 and continuously extracted from line 64. Liquid was extracted from the bottom of the column through line 63 into storage tank 606 at the rate of about 119 g/hr.

The composition of the liquid extracted from line 64 consisted of about 0.6% by weight of dibutyl carbonate, about 99% by weight of butylphenyl carbonate and about 0.4% by weight of diphenyl carbonate. The composition of the liquid extracted to storage tank 606 consisted of 0.1% by weight of dibutyl carbonate and about 99.9% by weight of diphenyl carbonate. The diphenyl carbonate contained 22 ppm of a metal component in the form of lead.

Example 1

Step (1-1): Production of N,N'-Hexanediyl-bis-carbamic Acid Diphenyl Ester

Figure 7:
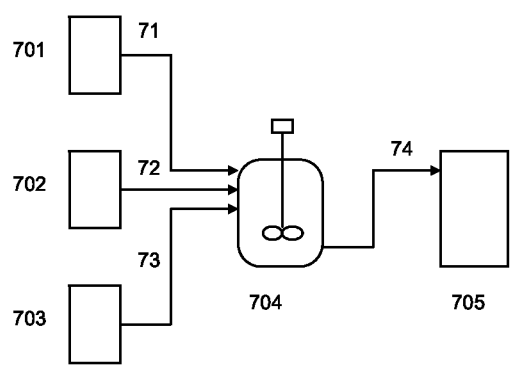
FIG. 7 is a conceptual drawing showing an aryl carbamate production apparatus according to an embodiment of the present invention.
Figure 8:
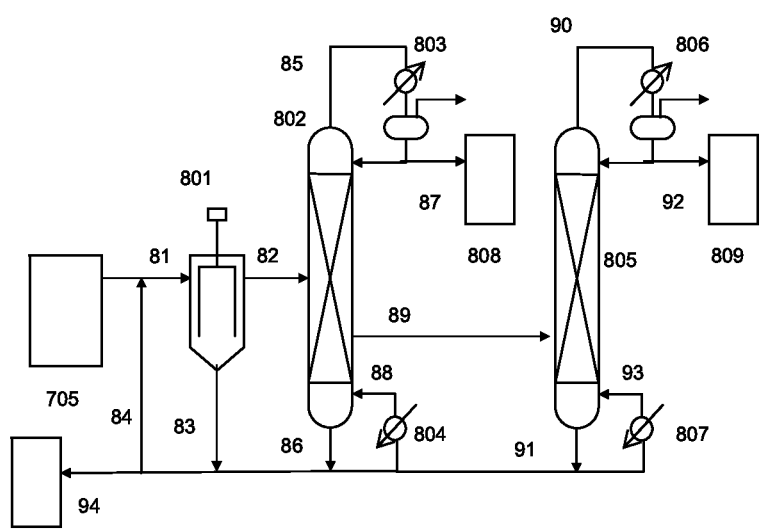
FIG. 8 is a conceptual drawing showing an isocyanate production apparatus according to an embodiment of the present invention.

A reaction was carried out using an apparatus like that shown in FIG. 7.

1350 g (6.3 mol) of the diphenyl carbonate of Reference Example 1 were supplied to baffled reaction vessel 704 made of SUS and having an inner volume of 5 L from storage tank 701 via line 71 with line 74 closed, and 987 g (10.5 mol) of phenol (Aldrich Corp., USA) were supplied to the reaction vessel made of SUS from storage tank 702 via line 72. The liquid temperature inside reaction vessel 704 was adjusted to about 50° C., and 244 g (2.1 mol) of hexamethylene diamine (Aldrich Corp., USA) were supplied to reaction vessel 704 from storage tank 703 via line 73 at the rate of about 200 g/hr.

As a result of analyzing the solution following the reaction by liquid chromatography, N,N'-hexanediyl-bis-carbamic acid diphenyl ester was found to have been formed at a yield of 99.5%.

Line 74 was opened and the reaction liquid was transferred to storage tank 705 via line 74.

Step (1-2): Production of Isocyanate by Thermal Decomposition of N,N'-hexanediyl-bis-carbamic Acid Diphenyl Ester A reaction was carried out using an apparatus like that shown in FIG. 8.

Thin film distillation apparatus 801 (Kobelco Eco-Solutions Co., Ltd., Japan) having a heat-conducting surface area of 0.1 m$^2$ was heated to 220° C. and the pressure within the thin film distillation apparatus was set to be about 13 kPa. The mixture recovered into storage tank 705 in step (1-1) was heated to 150° C. and supplied to the top of thin film distillation apparatus 801 via line 81 at the rate of about 800 g/hr. A liquid phase component was extracted from the bottom of thin film distillation apparatus 801 via line 83, and circulated to the top of thin film distillation apparatus 801 via line 84 and line 81. A gaseous phase component was extracted from line 82.

The gaseous phase component extracted from thin film distillation apparatus 801 via line 82 was continuously fed to the middle stage of continuous multistage distillation column 802 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line 86 and reboiler 804. The liquid temperature in the bottom of continuous multistage distillation column 802 was 150° C., and the pressure at the top of the column was about 15 kPa. Gas distilled from the top of continuous multistage distillation column 802 was condensed in condenser 803 via line 85 and continuously extracted from line 87. A liquid phase component was extracted from line 89 of continuous multistage distillation column 802 at a location lower than line 82.

The liquid phase component extracted from line 89 was continuously fed to the middle stage of continuous multistage distillation column 805 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line 91 and reboiler 807. The liquid temperature in the bottom of continuous multistage distillation column 805 was 150° C., and the pressure at the top of the column was about 1.5 kPa. Gas distilled from the top of continuous multistage distillation column 805 was condensed in condenser 806 via line 90 and continuously extracted into storage tank 809 via line 92. The extracted amount in the steady state was about 104 g/hr.

The liquid phase component was extracted into storage tank 810 from line 94 at the rate of about 140 g/hr in the steady state. The liquid phase component contained about 97% by weight of diphenyl carbonate.

The liquid extracted from line 92 was a solution that contained about 99.8% by weight of hexamethylene diisocyanate. The yield based on hexamethylene diamine was 95.3%.

Step (1-3): Recycling of Diaryl Carbonate

Figure 9:
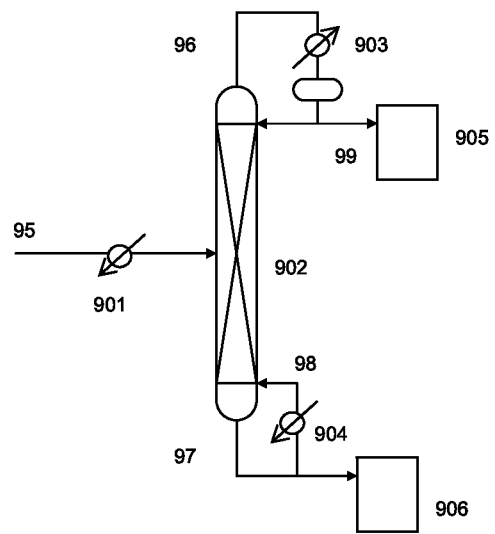
FIG. 9 is a conceptual drawing showing an isocyanate production apparatus according to an embodiment of the present invention.
Figure 10:
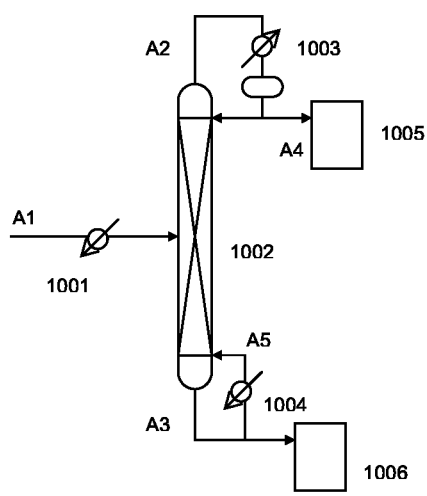
FIG. 10 is a conceptual drawing showing an isocyanate production apparatus according to an embodiment of the present invention.

Diaryl carbonate was recycled using an apparatus like that shown in FIGS. 9 and 10.

The liquid extracted from line 94 in step (1-2) was continuously fed through preheater 901 to the middle stage of continuous multistage distillation column 902 packed with Dickson packing (diameter: 6 mm) and having an inner diameter of about 5 cm and column length of 2 m from line 95 at the rate of about 195 g/hr. The amount of heat required for distillative separation was supplied by circulating the liquid in the bottom of the column through line 97 and reboiler 904. The liquid temperature in the bottom of continuous multistage distillation column 902 was 210° C., the pressure at the top of the column was about 1.5 kPa, and the reflux ratio was set to be about 1. Gas distilled from the top of continuous multistage distillation column 902 was condensed in condenser 903 via line 96 and continuously extracted from line 99. Liquid was extracted into storage tank 906 from the bottom of the column via line 97 at the rate of about 14 g/hr.

The liquid extracted from line 99 was continuously fed through preheater 1001 to the middle stage of continuous multistage distillation column 1002 packed with Dickson packing (diameter: 6 mm) and having an inner diameter of about 5 cm and column length of 2 m from line A1 at the rate of about 181 g/hr. The amount of heat required for distillative separation was supplied by circulating the liquid in the bottom of the column through line A3 and reboiler 1004. The liquid temperature in the bottom of continuous multistage distillation column 1002 was 232° C., the pressure at the top of the column was about 15 kPa, and the reflux ratio was set to be about 2. Gas distilled from the top of continuous multistage distillation column 1002 was condensed in condenser 1003 via line A2 and continuously extracted from line A4. Liquid was extracted into storage tank 1006 from the bottom of the column via line A3 at the rate of about 119 g/hr. The liquid extracted into storage tank 1006 contained about 99.9% by weight of diphenyl carbonate.

Step (1-4): Recycling of Phenol

Figure 11:
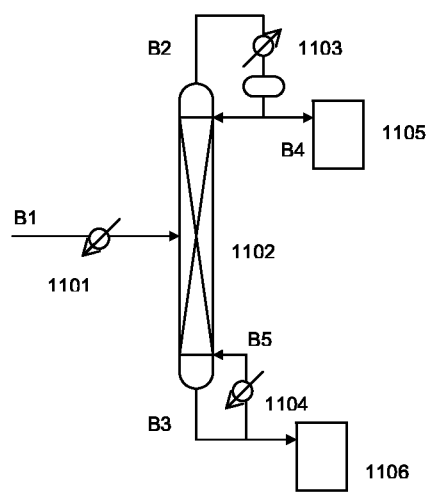
FIG. 11 is a conceptual drawing showing an isocyanate production apparatus according to an embodiment of the present invention.

Phenol was recycled using an apparatus like that shown in FIG. 11.

The liquid extracted from line 87 in step (1-2) was continuously fed through preheater 1101 to the middle stage of continuous multistage distillation column 1102 packed with Dickson packing (diameter: 6 mm) and having an inner diameter of about 5 cm and column length of 2 m from line B1 at the rate of about 200 g/hr. The amount of heat required for distillative separation was supplied by circulating the liquid in the bottom of the column through line B3 and reboiler 1104. The liquid temperature in the bottom of continuous multistage distillation column 1102 was 230° C., the pressure at the top of the column was at atmospheric pressure, and the reflux ratio was set to be about 1. Gas distilled from the top of continuous multistage distillation column 1102 was condensed in condenser 1103 via line B2 and continuously extracted into storage tank 1105 from line A4. The liquid extracted into storage tank 1105 contained about 99.9% by weight of phenol. Although continuous operation was carried out for 10 days, there was no accumulation of adhered substances observed on the walls of thin film distillation apparatus 801. Moreover, when continuous operation was carried out for 300 days, accumulation of adhered substances was observed on the walls of thin film distillation apparatus 801.

Example 2

Step (2-1): Production of 3-(phenoxycarbonylaminomethyl)-3,5,5-trimethylcyclohexyl Carbamic Acid Phenyl Ester A reaction was carried out using an apparatus like that shown in FIG. 7.

1992 g (9.3 mol) of the diphenyl carbonate of Reference Example 1 were supplied to baffled reaction vessel 704 made of SUS and having an inner volume of 5 L from storage tank 701 via line 71 with line 74 closed, and 1311 g (14.0 mol) of phenol were supplied to the reaction vessel made of SUS from storage tank 702 via line 72. The liquid temperature inside reaction vessel 704 was adjusted to about 50° C., and 528 g (3.1 mol) of 3-aminomethyl-3,5,5-trimethylcyclohexylamine (Aldrich Corp., USA) were supplied to reaction vessel 704 from storage tank 703 via line 73 at the rate of about 250 g/hr.

As a result of analyzing the solution following the reaction by liquid chromatography, 3-(phenoxycarbonylamino-methyl)-3,5,5-trimethylcyclohexyl carbamic acid phenyl ester was found to have been formed at a yield of 99.3%.

Line 74 was opened and the reaction liquid was transferred to storage tank 705 via line 74.

Step (2-2): Production of Isocyanate by Thermal Decomposition of 3-(phenoxycarbonylamino-methyl)-3,5,5-trimethylcyclohexyl Carbamic Acid Phenyl Ester A reaction was carried out using an apparatus like that shown in FIG. 8.

Thin film distillation apparatus 801 (Kobelco Eco-Solutions Co., Ltd., Japan) having a heat-conducting surface area of 0.1 m$^2$ was heated to 220° C. and the pressure within the thin film distillation apparatus was set to be about 13 kPa. The mixture recovered into storage tank 705 in step (2-1) was heated to 150° C. and supplied to the top of thin film distillation apparatus 801 via line 81 at the rate of about 780 g/hr. A liquid phase component was extracted from the bottom of thin film distillation apparatus 801 via line 83, and circulated to the top of the thin film distillation apparatus 801 via line 84 and line 81. A gaseous phase component was extracted from line 82.

The gaseous phase component extracted from thin film distillation apparatus 801 via line 82 was continuously fed to the middle stage of continuous multistage distillation column 802 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line 86 and reboiler 804. The liquid temperature in the bottom of continuous multistage distillation column 802 was 150° C., and the pressure at the top of the column was about 15 kPa. Gas distilled from the top of continuous multistage distillation column 802 was condensed in condenser 803 via line 85 and continuously extracted from line 87. A liquid phase component was extracted from line 89 of continuous multistage distillation column 802 at a location lower than line 82.

The liquid phase component extracted from line 89 was continuously fed to the middle stage of continuous multistage distillation column 805 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line 91 and reboiler 807. The liquid temperature in the bottom of continuous multistage distillation column 805 was 150° C., and the pressure at the top of the column was about 1.3 kPa. Gas distilled from the top of continuous multistage distillation column 805 was condensed in condenser 806 via line 90 and continuously extracted into storage tank 809 via line 92 at the rate of about 134 g/hr.

The liquid extracted from line 92 was a solution containing about 99.8% by weight of isophorone diisocyanate. The yield based on 3-amino-methyl-3,5,5-trimethylcyclohexylamine was 95.0%. Although continuous operation was carried out for 10 days, there was no accumulation of adhered substances observed on the walls of thin film distillation apparatus 801.

Example 3

Step (3-1): Production of Diphenyl-4,4'-methylene-dicyclohexyl Carbamate

Ferrous acetylacetonate was added to the diphenyl carbonate of Reference Example 1 to prepare diphenyl carbonate containing 2.3% of metal atoms in the form of iron.

A reaction was carried out using an apparatus like that shown in FIG. 7.

1577 g (7.4 mol) of diphenyl carbonate were supplied to baffled reaction vessel 704 made of SUS and having an inner volume of 5 L from storage tank 701 via line 71 with line 74 closed, and 1189 g (12.7 mol) of phenol were supplied to the reaction vessel made of SUS from storage tank 702 via line 72. The liquid temperature inside reaction vessel 704 was adjusted to about 50° C., and 484 g (2.3 mol) of 4,4'-methylenebis(cyclohexylamine) (Aldrich Corp., USA) were supplied to reaction vessel 704 from storage tank 703 via line 73 at the rate of about 250 g/hr.

As a result of analyzing the solution following the reaction by liquid chromatography, diphenyl-4,4'-methylene-dicyclohexyl carbamate was found to have been formed at a yield of 99.1%.

Line 74 was opened and the reaction liquid was transferred to storage tank 705 via line 74.

Step (3-2): Production of Isocyanate by Thermal Decomposition of Diphenyl-4,4'-methylene-dicyclohexyl Carbamate A reaction was carried out using an apparatus like that shown in FIG. 12.

A thin film distillation apparatus 1201 (Kobelco Eco-Solutions Co., Ltd., Japan) having a heat-conducting surface area of 0.1 m$^2$ was heated to 250° C. and the pressure within the thin film distillation apparatus was set to be about 1.3 kPa. The mixture recovered into storage tank 705 in step (3-1) was heated to 170° C. and supplied to the top of thin film distillation apparatus 1201 via line C1 at the rate of about 650 g/hr. A liquid phase component was extracted from the bottom of thin film distillation apparatus 1201 via line C3, and circulated to the top of thin film distillation apparatus 1201 via line C4 and line C1. A gaseous phase component was extracted from line C2.

The gaseous phase component extracted from thin film distillation apparatus 1201 via line C2 was continuously fed to the middle stage of continuous multistage distillation column 1202 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line C6 and reboiler 1204. The liquid temperature in the bottom of continuous multistage distillation column 1201 was 210° C., and the pressure at the top of the column was at atmospheric pressure. Gas distilled from the top of continuous multistage distillation column 1201 was condensed in condenser 1203 via line C5 and continuously extracted from line C7. A liquid phase component was extracted from line C8.

The liquid phase component extracted from line C8 was continuously fed to the middle stage of continuous multistage distillation column 1205 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line C11 and reboiler 1207. The liquid temperature in the bottom of continuous multistage distillation column 1205 was 210° C., and the pressure at the top of the column was about 2.5 kPa. Gas distilled from the top of continuous multistage distillation column 1205 was condensed in condenser 1206 via line C10 and continuously extracted via line C12. A liquid phase component was extracted from line C14.

The liquid phase component extracted from line C14 was continuously fed to the middle stage of continuous multistage distillation column 1208 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line C16 and reboiler 1210. The liquid temperature in the bottom of continuous multistage distillation column 1208 was 220° C., and the pressure at the top of the column was about 0.5 kPa. Gas distilled from the top of continuous multistage distillation column 1205 was condensed in condenser 1209 via line C15 and continuously extracted via line C17 at the rate of about 113 g/hr. The liquid extracted from line C17 was a solution containing about 99.9% by weight of 4,4'-methylene-bis(cyclohexylisocyanate). The yield based on 4,4'-methylenebis(cyclohexylamine) was 93.2%. Although continuous operation was carried out for 10 days, there was no accumulation of adhered substances observed on the walls of thin film distillation apparatus 1202.

Example 4

Step (4-1): Production of Diphenyl-4,4'-methylene-dicyclohexyl Carbamate

The same process as that of step (3-1) of Example 3 was carried out with the exception of using 1344 g (11.0 mol) of 2,6-dimethylphenol (Aldrich Corp., USA) and 463 g (2.2 mol) of 4,4'-methylenebis(cyclohexylamine) instead of 1650 g (7.7 mol) of diphenyl carbonate of Reference Example 1 and phenol. As a result of analyzing the solution following the reaction by liquid chromatography, diphenyl-4,4'-methylene-dicyclohexyl carbamate was found to have been formed at a yield of 99.3%.

Step (4-2): Production of Isocyanate by Thermal Decomposition of Diphenyl-4,4'-methylene-dicyclohexyl Carbamate The same process as that of step (3-2) of Example 3 was carried out with the exception of using the mixture obtained in step (4-1) instead of the mixture obtained in step (3-1) and heating the mixture to 140° C. A mixture of phenol and 2,6-dimethyl phenol was extracted from line C7. The liquid extracted from line C17 contained about 99.9% by weight of 4,4'-methylene-bis(cyclohexylisocyanate). The yield based on 4,4'-methylenebis(cyclohexylamine) was 92.3%. Although continuous operation was carried out for 10 days, there was no accumulation of adhered substances observed on the walls of thin film distillation apparatus 1202.

Example 5

Step (5-1): Production of N,N'-hexanediyl-bis-carbamic Acid Diphenyl Ester

The same process as that of step (1-1) of Example 1 was carried out with the exception of supplying 1874 g (8.8 mol) of diphenyl carbonate, 1246 g (13.3 mol) of phenol and 291 g (2.5 mol) of hexamethylene diamine of Reference Example 1.

As a result of analyzing the solution following the reaction by liquid chromatography, N,N'-hexanediyl-bis-carbamic acid diphenyl ester was found to have been formed at a yield of 99.4%.

Step (5-2): Production of Isocyanate by Thermal Decomposition of N,N'-hexanediyl-bis-carbamic Acid Diphenyl Ester The same process as that of step (1-2) of Example 1 was carried out with the exception of using the mixture obtained in step (5-1) instead of the mixture obtained in step (1-1), heating the mixture to 190° C. and supplying to thin film distillation apparatus 801. A liquid was continuously extracted from line 92 into storage tank 809 at the rate of about 76.5 g/hr. The liquid extracted from line 92 was a solution containing about 99.8% by weight of hexamethylene diisocyanate. The yield based on hexamethylene diamine was 77.5%. Although continuous operation was carried out for 10 days, there was no accumulation of adhered substances observed on the walls of thin film distillation apparatus 801.

Example 6

Step (6-1): Production of N,N'-hexanediyl-bis-carbamic Acid Diphenyl Ester

The same process as that of step (1-1) of Example 1 was carried out with the exception of supplying 2056 g (9.6 mol) of diphenyl carbonate of Reference Example 1, 1504 g (16.0 mol) of phenol and 372 g (3.2 mol) of hexamethylene diamine.

As a result of analyzing the solution following the reaction by liquid chromatography, N,N'-hexanediyl-bis-carbamic acid diphenyl ester was found to have been formed at a yield of 99.4%.

Step (6-2): Production of Isocyanate by Thermal Decomposition of N,N'-hexanediyl-bis-carbamic Acid Diphenyl Ester A reaction was carried out using an apparatus like that shown in FIG. 8.

Thin film distillation apparatus 801 having a heat-conducting surface area of 0.1 m$^2$ was heated to 220° C. and the pressure within the thin film distillation apparatus was set to be about 0.13 kPa. The mixture recovered into storage tank 705 in step (6-1) was heated to 100° C. and supplied to the top of thin film distillation apparatus 801 via line 81 at the rate of about 800 g/hr. A gaseous phase component was extracted from the bottom of thin film distillation apparatus 801 via line 82. Hardly any liquid phase component was recovered from line 83 provided in the bottom of thin film distillation apparatus 801.

The gaseous phase component extracted from thin film distillation apparatus 801 via line 82 was continuously fed to the middle stage of continuous multistage distillation column 802 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line 86 and reboiler 804. The liquid temperature in the bottom of continuous multistage distillation column 802 was 150° C., and the pressure at the top of the column was about 8 kPa. Gas distilled from the top of continuous multistage distillation column 802 was condensed in condenser 803 via line 85 and continuously extracted from line 87. A liquid phase component was extracted from line 89 of continuous multistage distillation column 802 at a location lower than line 82.

The liquid phase component extracted from line 89 was continuously fed to the middle stage of continuous multistage distillation column 805 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line 91 and reboiler 807. The liquid temperature in the bottom of continuous multistage distillation column 805 was 150° C., and the pressure at the top of the column was about 1.5 kPa. Gas distilled from the top of continuous multistage distillation column 805 was condensed in condenser 806 via line 90 and continuously extracted into storage tank 809 via line 92. The extracted amount in the steady state was about 104 g/hr.

The liquid extracted from line 92 was a solution containing about 99.9% by weight of hexamethylene diisocyanate. The yield based on hexamethylene diamine was 95.4%. When continuous operation was carried out for 10 days, accumulation of adhered substances was observed on the walls of thin film distillation apparatus 801.

Example 7

Step (7-1): Production of Diphenyl-4,4'-methylene-dicyclohexyl Carbamate

The same process as that of step (3-1) of Example 3 was carried out with the exception of using 1874 g (8.8 mol) of diphenyl carbonate of Reference Example 1, 1175 g (12.5 mol) of phenol and 526 g (2.5 mol) of 4,4'-methylenebis (cyclohexylamine).

As a result of analyzing the solution following the reaction by liquid chromatography, diphenyl-4,4'-methylene-dicyclohexyl carbamate was found to have been formed at a yield of 99.2%.

Step (7-2): Production of Isocyanate by Thermal Decomposition of Diphenyl-4,4'-methylene-dicyclohexyl Carbamate A reaction was carried out using an apparatus like that shown in FIG. 13.

The mixture recovered into storage tank 705 in step (7-1) was heated to 150° C. and fed to the middle stage of a continuous multistage distillation column 1301 packed with Dickson packing (diameter: 6 mm) and having an inner diameter of about 5 cm and column length of 2 m via line D1 at the rate of about 510 g/hr to carry out a thermal decomposition reaction. The amount of heat required for thermal decomposition was supplied by circulating the liquid in the bottom of the column through line D3 and reboiler 1303. The liquid temperature in the bottom of continuous multistage distillation column 1301 was 220° C., and the pressure at the top of the column was about 15 kPa. Gas distilled from the top of continuous multistage distillation column 1301 was condensed in condenser 1302 via line D2 and continuously extracted from line D4. A liquid phase component was extracted from continuous multistage distillation column 1301 via line D3.

The liquid phase component extracted from line D6 was continuously fed to the middle stage of a continuous multistage distillation column 1304 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line D8 and reboiler 1306. The liquid temperature in the bottom of continuous multistage distillation column 1304 was 220° C., and the pressure at the top of the column was about 5.2 kPa. Gas distilled from the top of continuous multistage distillation column 1304 was condensed in condenser 1305 via line D7 and continuously extracted from line D9. A liquid phase component was recovered from the bottom of continuous multistage distillation column 1304 via line D8 and line D11.

The liquid phase component extracted from line D8 was continuously fed to the middle stage of continuous multistage distillation column 1307 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line D14 and reboiler 1309. The liquid temperature in the bottom of continuous multistage distillation column 1307 was 220° C., and the pressure at the top of the column was about 0.40 kPa. Gas distilled from the top of continuous multistage distillation column 1307 was condensed in condenser 1308 via line D12 and continuously extracted via line D13. The extracted amount in the steady state was about 75 g/hr.

The liquid extracted from line D13 was a solution containing about 99.8% by weight of 4,4'-methylene-bis(cyclohexylisocyanate). The yield based on 4,4'-methylenebis(cyclohexylamine) was 80.4%. When continuous operation was carried out for 10 days, accumulation of adhered substances was observed inside thin film distillation apparatus 1301.

Example 8

Step (8-1): Production of N,N'-hexanediyl-bis-carbamic Acid Diphenyl Ester

The same process as that of step (1-1) of Example 1 was carried out with the exception of supplying 2204 g (8.4 mol) of 4-dodecylphenol (Aldrich Corp., USA) and 244 g (2.1 mol) of hexamethylene diamine instead of 1350 g (6.3 mol) of diphenyl carbonate of Reference Example 1 and phenol.

As a result of analyzing the solution following the reaction by liquid chromatography, N,N'-hexanediyl-bis-carbamic acid diphenyl ester was found to have been formed at a yield of 99.0%.

Step (8-2): Production of Isocyanate by Thermal Decomposition of N,N'-hexanediyl-bis-carbamic Acid Diphenyl Ester A reaction was carried out using an apparatus like that shown in FIG. 8.

Thin film distillation apparatus 801 having a heat-conducting surface area of 0.1 m$^2$ was heated to 220° C. and the pressure within the thin film distillation apparatus was set to be about 5.2 kPa. The mixture recovered into storage tank 705 in step (8-1) was heated to 150° C. and supplied to the top of thin film distillation apparatus 801 via line 81 at the rate of about 1200 g/hr. A liquid phase component was extracted from the bottom of thin film distillation apparatus 801 via line 83, and circulated to the top of the thin film distillation apparatus 801 via line 84 and line 81. A gaseous phase component was extracted from line 82.

The gaseous phase component extracted from thin film distillation apparatus 801 via line 82 was continuously fed to the middle stage of continuous multistage distillation column 802 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line 86 and reboiler 804. The liquid temperature in the bottom of continuous multistage distillation column 802 was 150° C., and the pressure at the top of the column was about 4.0 kPa. Gas distilled from the top of continuous multistage distillation column 802 was condensed in condenser 803 via line 85 and continuously extracted from line 87. A liquid phase component was extracted from line 89 of continuous multistage distillation column 802 at a location lower than line 82.

The liquid phase component extracted from line 89 was continuously fed to the middle stage of continuous multistage distillation column 805 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line 91 and reboiler 807. The liquid temperature in the bottom of continuous multistage distillation column 805 was 150° C., and the pressure at the top of the column was about 0.8 kPa. Gas distilled from the top of continuous multistage distillation column 805 was condensed in condenser 806 via line 90 and continuously extracted into storage tank 809 via line 92. The extracted amount in the steady state was about 104 g/hr.

The liquid phase component was extracted into storage tank 810 from line 94 at the rate of about 690 g/hr in the steady state. The liquid phase component contained about 97% by weight of 4-dodecylphenol.

A liquid extracted from line 92 was a solution that contained about 99.8% by weight of hexamethylene diisocyanate. The yield based on hexamethylene diamine was 93.1%. Although continuous operation was carried out for 10 days, there was no accumulation of adhered substances observed on the walls of thin film distillation apparatus 801.

Example 9

Step (9-1): Production of 3-(phenoxycarbonylaminomethyl)-3,5,5-trimethylcyclohexyl Carbamic Acid Phenyl Ester The same process as that of step (2-1) of Example 2 was carried out with the exception of supplying 2643 g (8.0 mol)

of 2,4-(α,α-dimethylbenzyl)phenol (Tokyo Chemical Industry Co., Ltd., Japan) and 273 g (1.6 mol) of 3-aminomethyl-3,5,5-trimethylcyclohexylamine instead of 1028 g (4.8 mol) of diphenyl carbonate of Reference Example 1 and phenol.

As a result of analyzing the solution following the reaction by liquid chromatography, 3-(phenoxycarbonylamino-methyl)-3,5,5-trimethylcyclohexyl carbamic acid phenyl ester was found to have been formed at a yield of 99.0%.

Step (9-2): Production of Isocyanate by Thermal Decomposition of 3-(phenoxycarbonylamino-methyl)-3,5,5-trimethylcyclohexyl Carbamic Acid Phenyl Ester The same process as step (8-2) of Example 8 was carried out with the exception of using the mixture obtained in step (9-1) instead of the mixture obtained step (8-1), heating the mixture to 150° C. and supplying at the rate of about 1310 g/hr.

Gas distilled from the top of the continuous multistage distillation column 805 was condensed in condenser 806 via line 90 and continuously extracted into storage tank 809 via line 92 at the rate of about 112 g/hr.

The liquid extracted from line 92 was a solution that contained about 99.8% by weight of isophorone diisocyanate. The yield based on 3-aminomethyl-3,5,5-trimethylcyclohexylamine was 94.5%. Although continuous operation was carried out for 10 days, there was no accumulation of adhered substances observed on the walls of thin film distillation apparatus 801.

Example 10

Step (10-1): Production of N,N'-(4,4'-methanediyl-diphenyl)-biscarbamic Acid Diphenyl Ester A reaction was carried out using an apparatus like that shown in FIG. 7.

A mixture of 1478 g (6.9 mol) of the diphenyl carbonate of Reference Example 1 and 50.5 g (0.2 mol) of zinc acetate dihydrate (Aldrich Corp., USA) were supplied to baffled reaction vessel 704 made of SUS and having an inner volume of 5 L from storage tank 701 via line 71 with line 74 closed, and 1297 g (13.8 mol) of phenol were supplied to the reaction vessel made of SUS from storage tank 702 via line 72. The liquid temperature inside reaction vessel 704 was adjusted to about 50° C., and 456 g (2.3 mol) of 4,4'-methylenedianiline (Aldrich Corp., USA) were supplied to reaction vessel 704 from storage tank 703 via line 73 at the rate of about 200 g/hr.

As a result of analyzing the solution following the reaction by liquid chromatography, N,N'-(4,4'-methanediyl-diphenyl)-biscarbamic acid diphenyl ester was found to have been formed at a yield of 98.8%.

Line 74 was opened and the reaction liquid was transferred to storage tank 705 via line 74.

Step (10-2): Production of Isocyanate by Thermal Decomposition of N,N'-(4,4'-methanediyl-diphenyl) biscarbamic Acid Diphenyl Ester A reaction was carried out using an apparatus like that shown in FIG. 12.

Thin film distillation apparatus 1201 having a heat-conducting surface area of 0.1 m² was heated to 230° C. and the pressure within the thin film distillation apparatus was set to be about 1.3 kPa. The mixture recovered into storage tank 705 in step (10-1) was heated to 130° C. and supplied to the top of thin film distillation apparatus 1201 via line C1 at the rate of about 690 g/hr. A liquid phase component was extracted from the bottom of thin film distillation apparatus 1201 via line C3, and circulated to the top of thin film distillation apparatus 1201 via line C4 and line C1. A gaseous phase component was extracted from line C2.

The gaseous phase component extracted from thin film distillation apparatus 1201 via line C2 was continuously fed to the middle stage of continuous multistage distillation column 1202 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line 86 and reboiler 804. The liquid temperature in the bottom of continuous multistage distillation column 1201 was 200° C., and the pressure at the top of the column was 60 kPa. Gas distilled from the top of continuous multistage distillation column 1201 was condensed in condenser 1203 via line C5 and continuously extracted from line C7. A liquid phase component was extracted from line C8.

The liquid phase component extracted from line C8 was continuously fed to the middle stage of continuous multistage distillation column 1205 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line C11 and reboiler 1207. The liquid temperature in the bottom of continuous multistage distillation column 1205 was 210° C., and the pressure at the top of the column was about 2.5 kPa. Gas distilled from the top of continuous multistage distillation column 1205 was condensed in condenser 1206 via line C10 and continuously extracted via line C12. A liquid phase component was extracted from line C14.

The liquid phase component extracted from line C14 was continuously fed to the middle stage of continuous multistage distillation column 1208 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line C16 and reboiler 1210. The liquid temperature in the bottom of continuous multistage distillation column 1208 was 220° C., and the pressure at the top of the column was about 0.5 kPa. Gas distilled from the top of continuous multistage distillation column 1205 was condensed in condenser 1209 via line C15 and continuously extracted via line C17 at the rate of about 99.6 g/hr. The liquid extracted from line C17 contained about 99.9% by weight of 4,4'-diphenylmethane diisocyanate. The yield based on 4,4'-methylenedianiline was 82.3%. Although continuous operation was carried out for 10 days, there was no accumulation of adhered substances observed on the walls of thin film distillation apparatus 1202.

Example 11

Step (11-1): Production of Toluene-2,4-dicarbamic Acid Diphenyl Ester

A reaction was carried out using an apparatus like that shown in FIG. 7.

A mixture of 2125 g (9.9 mol) of the diphenyl carbonate of Reference Example 1 and 35.1 g (0.2 mol) of zinc acetate dihydrate were supplied to baffled reaction vessel 704 made of SUS and having an inner volume of 5 L from storage tank 701 via line 71 with line 74 closed, and 1534 g (16.3 mol) of phenol were supplied to the reaction vessel made of SUS from storage tank 702 via line 72. The liquid temperature inside reaction vessel 704 was adjusted to about 50° C., and 391 g (3.2 mol) of 2,4-toluenediamine (Aldrich Corp., USA) were supplied to reaction vessel 704 from storage tank 703 via line 73 at the rate of about 230 g/hr.

As a result of analyzing the solution following the reaction by liquid chromatography, toluene-2,4-dicarbamic acid diphenyl ester was found to have been formed at a yield of 98.1%.

Line 74 was opened and the reaction liquid was transferred to storage tank 705 via line 74.

Step (11-2): Production of Isocyanate by Thermal Decomposition of Toluene-2,4-dicarbamic Acid Diphenyl Ester A reaction was carried out using an apparatus like that shown in FIG. 8.

Thin film distillation apparatus 801 having a heat-conducting surface area of 0.1 m² was heated to 220° C. and the pressure within the thin film distillation apparatus was set to be about 13 kPa. The mixture recovered into storage tank 705 in step (11-1) was heated to 130° C. and supplied to the top of thin film distillation apparatus 801 via line 81 at the rate of about 820 g/hr. A liquid phase component was extracted from the bottom of thin film distillation apparatus 801 via line 83, and circulated to the top of thin film distillation apparatus 801 via line 84 and line 81. A gaseous phase component was extracted from line 82.

The gaseous phase component extracted from thin film distillation apparatus 801 via line 82 was continuously fed to the middle stage of continuous multistage distillation column 802 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line 86 and reboiler 804. The liquid temperature in the bottom of continuous multistage distillation column 802 was 150° C., and the pressure at the top of the column was about 15 kPa. Gas distilled from the top of continuous multistage distillation column 802 was condensed in condenser 803 via line 85 and continuously extracted from line 87. A liquid phase component was extracted from line 89 of continuous multistage distillation column 802 at a location lower than line 82.

The liquid phase component extracted from line 89 was continuously fed to the middle stage of continuous multistage distillation column 805 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line 91 and reboiler 807. The liquid temperature in the bottom of continuous multistage distillation column 805 was 150° C., and the pressure at the top of the column was about 1.3 kPa. Gas distilled from the top of continuous multistage distillation column 805 was condensed in condenser 806 via line 90 and continuously extracted into storage tank 809 via line 92 at the rate of about 93 g/hr.

The liquid extracted from line 92 was a solution containing about 99.7% by weight of 2,4-tolylene diisocyanate. The yield based on 2,4-toluenediamine was 83.4%. Although continuous operation was carried out for 10 days, there was no accumulation of adhered substances observed on the walls of thin film distillation apparatus 801.

Example 12

Step (12-1): Production of N,N'-(4,4'-methanediyl-diphenyl)-biscarbamic Acid Diphenyl Ester The same process as that of step (10-1) of Example 10 was carried out with the exception of using 1293 g (13.8 mol) of a mixture of 2055 g (9.5 mol) of the diphenyl carbonate of Reference Example 1 and 54.9 g (0.3 mol) of zinc acetate dihydrate, 1293 g (13.8 mol) of phenol and 496 g (2.5 mol) of 4,4'-methylenedianiline.

As a result of analyzing the solution following the reaction by liquid chromatography, N,N'-(4,4'-methanediyl-diphenyl)-biscarbamic acid diphenyl ester was found to have been formed at a yield of 98.6%.

(Step 12-2): Production of Isocyanate by Thermal Decomposition of N,N'-(4,4'-methanediyl-diphenyl) biscarbamic Acid Diphenyl Ester Using the mixture obtained in step (12-1) instead of the mixture obtained in step (7-1), the mixture was heated to 130° C. and fed through line D1 at the rate of about 700 g/hr to carry out a thermal decomposition reaction. The amount of heat required for thermal decomposition was supplied by circulating the liquid in the bottom of the column through line D3 and reboiler 1303. The liquid temperature in the bottom of continuous multistage distillation column 1301 was 220° C., and the pressure at the top of the column was about 15 kPa. Gas distilled from the top of continuous multistage distillation column 1301 was condensed in condenser 1302 via line D2 and continuously extracted from line D4. A liquid phase component was extracted from continuous multistage distillation column 1301 via line D3.

The liquid phase component extracted from line D6 was continuously fed to the middle stage of continuous multistage distillation column 1304 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line D8 and reboiler 1306. The liquid temperature in the bottom of continuous multistage distillation column 1304 was 220° C., and the pressure at the top of the column was about 5.2 kPa. Gas distilled from the top of continuous multistage distillation column 1304 was condensed in condenser 1305 via line D7 and continuously extracted from line D9. A liquid phase component was recovered from the bottom of continuous multistage distillation column 1304 via line D8 and line D11.

The liquid phase component extracted from line D8 was continuously fed to the middle stage of continuous multistage distillation column 1307 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line D14 and reboiler 1309. The liquid temperature in the bottom of continuous multistage distillation column 1307 was 220° C., and the pressure at the top of the column was about 0.40 kPa. Gas distilled from the top of continuous multistage distillation column 1307 was condensed in condenser 1308 via line D12 and continuously extracted via line D13. The extracted amount in the steady state was about 92 g/hr.

The liquid extracted from line D13 was a solution containing about 99.8% by weight of 4,4'-diphenylmethane diisocyanate. The yield based on 4,4'-methylenedianline was 76.9%. When continuous operation was carried out for 10 days, accumulation of adhered substances was observed inside thin film distillation apparatus 1301.

Example 13

Step (13-1): Production of N,N'-hexanediyl-bis-carbamic Acid Diphenyl Ester

The diphenyl carbonate of Reference Example 1 was placed in pear-shaped flask having an internal volume of 10 L, a three-way valve, distillation column packed with Helipak No. 3, fractionating column equipped with a reflux condenser and coupled to a distillate collector, and thermometer were attached to the pear-shaped flask and the inside of the system was replaced with nitrogen in a vacuum to carry out distillative purification of the diphenyl carbonate. When $^1$H-NMR measurement was carried out on the distillative purification product, it was found to contain about 99.9% by weight of diphenyl carbonate. In addition, it also contained 0.002 ppm of metal atoms in the form of iron.

The same process as that of step (1-1) of Example 1 was carried out with the exception of supplying 1414 g (6.6 mol) of the diphenyl carbonate, 1034 g (11.0 mol) of phenol and 256 g (2.2 mol) of hexamethylene diamine.

As a result of analyzing the solution following the reaction by liquid chromatography, N,N'-hexanediyl-bis-carbamic acid diphenyl ester was found to have been formed at a yield of 99.0%.

Step (13-2): Production of Isocyanate by Thermal Decomposition of N,N'-hexanediyl-bis-carbamic Acid Diphenyl Ester The same process as that of step (1-2) of Example 1 was carried out with the exception of using the mixture obtained in step (13-1) instead of the mixture obtained in step (1-1). Liquid was continuously extracted from line 92 into storage tank 809 at the rate of about 104 g/hr. The liquid extracted from line 92 was a solution containing about 99.8% by weight of hexamethylene diisocyanate. The yield based on hexamethylene diamine was 95.0%. Although continuous operation was carried out for 10 days, there was no accumulation of adhered substances observed on the walls of thin film distillation apparatus 801.

Example 14

Step (14-1): Production of N,N'-hexanediyl-bis-carbamic Acid Diphenyl Ester

Ferrous acetylacetonate was added to the diphenyl carbonate of Reference Example 1 to prepare diphenyl carbonate having a metal atom content in the form of iron of 8%. The same process as that of step (1-1) of Example 1 was carried out with the exception of supplying 1371 g (6.4 mol) of the diphenyl carbonate, 940 g (10.0 mol) of phenol and 232 g (2.0 mol) of hexamethylene diamine.

As a result of analyzing the solution following the reaction by liquid chromatography, N,N'-hexanediyl-bis-carbamic acid diphenyl ester was found to have been formed at a yield of 98.9%.

Step (14-2): Production of Isocyanate by Thermal Decomposition of N,N'-hexanediyl-bis-carbamic Acid Diphenyl Ester The same process as that of step (1-2) of Example 1 was carried out with the exception of using the mixture obtained in step (14-1) instead of the mixture obtained in step (1-1). Liquid was continuously extracted into storage tank 809 from line 92 at the rate of about 101 g/hr. The liquid extracted from line 92 was a solution containing about 99.8% by weight of hexamethylene diisocyanate. The yield based on hexamethylene diamine was 95.2%. Although continuous operation was carried out for 10 days, there was no accumulation of adhered substances observed on the walls of thin film distillation apparatus 801.

Example 15

Step (15-1): Production of N,N'-hexanediyl-bis-carbamic Acid Diphenyl Ester

The diphenyl carbonate of Reference Example 1 was placed in pear-shaped flask having an internal volume of 10 L, a three-way valve, distillation column packed with Helipak No. 3, fractionating column equipped with a reflux condenser and coupled to a distillate collector, and thermometer were attached to the pear-shaped flask and the inside of the system was replaced with nitrogen in a vacuum to carry out distillative purification of the diphenyl carbonate. The flask was cooled to terminate distillative purification when distillate equal to about one-fourth the charged amount was obtained. When $^1$H-NMR measurement was carried out on the distillate, it was found to contain about 99.9% by weight of diphenyl carbonate. In addition, the levels of metal atoms in the form of iron, cobalt, nickel, zinc, tin, copper and titanium contained in the distillate were below the detection limit (0.001 ppm).

The same process as that of step (1-1) of Example 1 was carried out with the exception of supplying 1553 g (7.3 mol) of the diphenyl carbonate, 1175 g (12.5 mol) of phenol and 291 g (2.5 mol) of hexamethylene diamine.

As a result of analyzing the solution following the reaction by liquid chromatography, N,N'-hexanediyl-bis-carbamic acid diphenyl ester was found to have been formed at a yield of 95.6%.

Step (15-2): Production of Isocyanate by Thermal Decomposition of N,N'-hexanediyl-bis-carbamic Acid Diphenyl Ester The same process as that of step (1-2) of Example 1 was carried out with the exception of using the mixture obtained in step (15-1) instead of the mixture obtained in step (1-1). Liquid was continuously extracted from line 92 into storage tank 809 at the rate of about 99.1 g/hr. The liquid extracted from line 92 was a solution containing about 99.8% by weight of hexamethylene diisocyanate. The yield based on hexamethylene diamine was 88.9%. Although continuous operation was carried out for 10 days, there was no accumulation of adhered substances observed on the walls of thin film distillation apparatus 801.

Example 16

Step (16-1): Production of N,N'-hexanediyl-bis-carbamic Acid Diphenyl Ester

Ferrous acetylacetonate was added to the diphenyl carbonate of Reference Example 1 to prepare diphenyl carbonate having a metal atom content in the form of iron of 13%. The same process as that of step (1-1) of Example 1 was carried out with the exception of supplying 1527 g (7.1 mol) of the diphenyl carbonate, 1081 g (11.5 mol) of phenol and 267 g (2.3 mol) of hexamethylene diamine.

As a result of analyzing the solution following the reaction by liquid chromatography, N,N'-hexanediyl-bis-carbamic acid diphenyl ester was found to have been formed at a yield of 94.5%.

Step (16-2): Production of Isocyanate by Thermal Decomposition of N,N'-hexanediyl-bis-carbamic Acid Diphenyl Ester The same process as that of step (1-2) of Example 1 was carried out with the exception of using the mixture obtained in step (16-1) instead of the mixture obtained in step (1-1). Liquid was continuously extracted into storage tank 809 from line 92 at the rate of about 95.1 g/hr. The liquid extracted from line 92 was a solution containing about 99.8% by weight of hexamethylene diisocyanate. The yield based on hexamethylene diamine was 88.0%. When continuous operation was carried out for 10 days, accumulation of adhered substances was observed on the walls of thin film distillation apparatus 801.

Example 17

Step (17-1): Production of N,N'-hexanediyl-bis-carbamic Acid Diphenyl Ester

The same process as that of step (1-1) of Example 1 was carried out with the exception of supplying 1350 g (6.3 mol) of diphenyl carbonate and 790 g (8.4 mol) of phenol, and supplying a mixture of 244 g (2.1 mol) of hexamethylene diamine and 197 g (2.1 mol) of phenol instead of hexamethylene diamine.

As a result of analyzing the solution following the reaction by liquid chromatography, N,N'-hexanediyl-bis-carbamic acid diphenyl ester was found to have been formed at a yield of 99.0%.

Step (17-2): Production of Isocyanate by Thermal Decomposition of N,N'-hexanediyl-bis-carbamic Acid Diphenyl Ester The same process as that of step (1-2) of Example 1 was carried out with the exception of using the mixture obtained in step (17-1) instead of the mixture obtained in step (1-1). Liquid was continuously extracted from line 92 into storage tank 809 at the rate of about 106 g/hr. The liquid extracted from line 92 was a solution containing about 99.8% by weight of hexamethylene diisocyanate. The yield based on hexamethylene diamine was 97.0%. Although continuous operation was carried out for 10 days, there was no accumulation of adhered substances observed on the walls of thin film distillation apparatus 801.

Example 18

Step (18-1): Production of N,N'-hexanediyl-bis-carbamic Acid Bis(3-methylbutyl) Ester A reaction was carried out using an apparatus like that shown in FIG. 16.

1660 g (7.8 mol) of the diphenyl carbonate were supplied to baffled reaction vessel 1604 made of SUS and having an inner volume of 5 L from storage tank 1601 via line G1 with line G4 closed, and 1175 g (12.5 mol) of phenol were supplied to the reaction vessel made of SUS from storage tank 1602 via line G2. The liquid temperature inside reaction vessel 1604 was adjusted to about 50° C., and a mixture of 291 g (2.5 mol) of hexamethylene diamine and water was supplied from storage tank 1603 via line G3 to reaction vessel 1604 at the rate of about 200 g/hr.

Following completion of the reaction, the pressure inside reaction vessel 1604 was reduced to 10 kPa and the water was distilled off. The water was condensed in condenser 1607 and extracted through line G6.

As a result of analyzing the solution following the reaction by liquid chromatography, N,N'-hexanediyl-bis-carbamic acid diphenyl ester was found to have been formed at a yield of 99.0%.

Line G4 was opened and the reaction liquid was transferred to storage tank 1605 via line G4.

Step (18-2): Production of Isocyanate by Thermal Decomposition of N,N'-hexanediyl-bis-carbamic Acid Diphenyl Ester The same process as that of step (1-2) of Example 1 was carried out with the exception of using the mixture obtained in step (18-1) instead of the mixture obtained in step (1-1). The heated surface area of thin film distillation apparatus 801 relative to the volume of the reaction vessel was larger than reaction vessel 1604 of FIG. 16. Liquid was continuously extracted from line 92 into storage tank 809 at the rate of about 104 g/hr. The liquid extracted from line 92 was a solution containing about 99.8% by weight of hexamethylene diisocyanate. The yield based on hexamethylene diamine was 96.5%. Although continuous operation was carried out for 10 days, there was no accumulation of adhered substances observed on the walls of thin film distillation apparatus 801.

Example 19

Cleaning of Reaction Vessel

A cleaning procedure was carried out on thin film distillation apparatus 801 in which accumulation of adhered substance was observed in Example 6. Thin film distillation apparatus 801 was heated to 180° C. and the inside of thin film distillation apparatus 801 was replaced with a nitrogen atmosphere at atmospheric pressure. Phenol was supplied from line 81 at the rate of about 1200 g/hr, extracted from line 83 and a liquid phase component was recovered from line 94 into storage tank 810. When this procedure was carried out for 1 hour, adhered substance was not observed on the inside of thin film distillation apparatus 801.

Examples 20 to 27

The procedure of Example 6 was carried out continuously and various cleaning solvents were used every 10 days to carry out the cleaning procedure using the same method as Example 19. Those results are shown in Table 1.

Comparative Example 1

Step (A-1): Production of N,N'-hexanediyl-bis-carbamic Acid Diphenyl Ester

Figure 14:
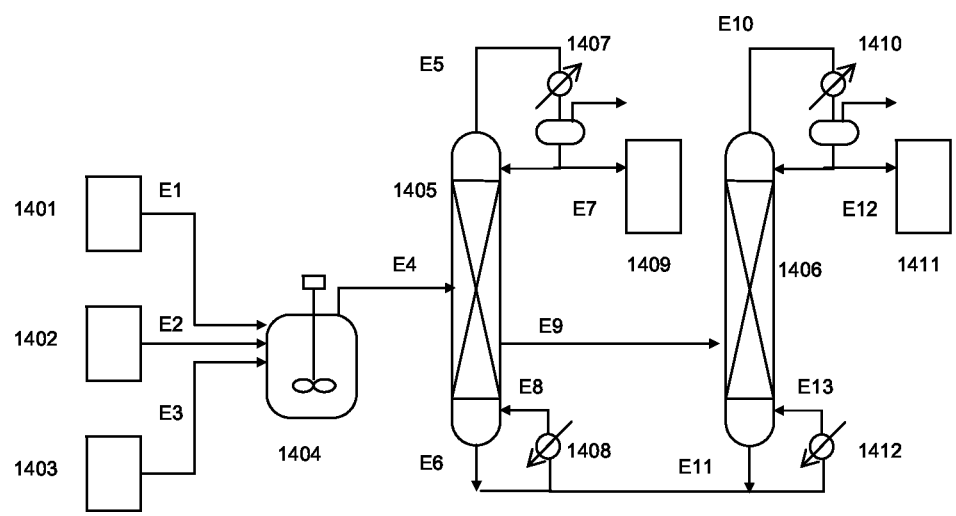
FIG. 14 is a conceptual drawing showing an isocyanate production apparatus according to an embodiment of the present invention.

A reaction was carried out using an apparatus like that shown in FIG. 14.

1979 g (9.2 mol) of diphenyl carbonate were supplied to baffled reaction vessel 1404 made of SUS and having an inner volume of 5 L from storage tank 1401 via line E1 with line E4 closed, and 1316 g (14.0 mol) of phenol were supplied to the reaction vessel made of SUS from storage tank 1402 via line E2. The liquid temperature inside reaction vessel 1404 was adjusted to about 50° C., and 325 g (2.8 mol) of hexamethylene diamine were supplied to reaction vessel 1404 from storage tank 1403 via line E3 at the rate of about 190 g/hr.

As a result of analyzing the solution following the reaction by liquid chromatography, N,N'-hexanediyl-bis-carbamic acid diphenyl ester was found to have been formed at a yield of 99.3%.

Step (A-2): Production of Isocyanate by Thermal Decomposition of N,N'-hexanediyl-bis-carbamic Acid Diphenyl Ester Continuing, a reaction was carried out using an apparatus like that shown in FIG. 14.

SUS reaction vessel 1404 was heated to 220° C. and the pressure inside the reaction vessel was reduced to 1.3 kPa. A gaseous phase component was extracted from line E4, and the gaseous phase component was continuously fed to the middle stage of continuous multistage distillation column 1405 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line E6 and reboiler 1408. The liquid temperature in the bottom of continuous multistage distillation column 1405 was 150° C., and the pressure at the top of the column was about 15 kPa. Gas distilled from the top of continuous multistage distillation column 1405 was condensed in condenser 1407 via line E5 and continuously extracted from line E7. A liquid phase component was extracted from line E9 of continuous multistage distillation column 1405 at a location lower than line E4.

The liquid phase component extracted from line E9 was continuously fed to the middle stage of continuous multistage distillation column 1406 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line E11 and reboiler 1412. The liquid temperature in the bottom of continuous multistage distillation column 1406 was 150° C., and the pressure at the top of the column was about 1.5 kPa. Gas distilled from the top of continuous multistage distillation column 1406 was condensed in condenser 1410 via line E10 and continuously extracted into storage tank 1411 via line E12. The amount of liquid recovered into storage tank 1411 was about 304 g. The liquid was a solution containing about 99.8% by weight of hexamethylene diisocyanate. The yield based on hexamethylene diamine was 64.5%.

Comparative Example 2

Step (B-1): Production of N,N'-(4,4'-methanediyl-diphenyl)-biscarbamic Acid Diphenyl Ester A reaction was carried out using an apparatus like that shown in FIG. 15.

A mixture of 1527 g (7.1 mol) of diphenyl carbonate and 50.5 g (0.2 mol) of zinc acetate dihydrate were supplied to baffled reaction vessel 1504 made of SUS and having an inner volume of 5 L from storage tank 1501 via line F1 with line F4 closed, and 1146 g (1.2 mol) of phenol were supplied to the reaction vessel made of SUS from storage tank 1502 via line F2. The liquid temperature inside reaction vessel 1504 was adjusted to about 50° C., and 456 g (2.3 mol) of 4,4'-methylenedianiline were supplied to reaction vessel 1504 from storage tank 1503 via line F3 at the rate of about 200 g/hr.

As a result of analyzing the solution following the reaction by liquid chromatography, N,N'-(4,4'-methanediyl-diphenyl)-biscarbamic acid diphenyl ester was found to have been formed at a yield of 98.3%.

Step (B-2): Production of Isocyanate by Thermal Decomposition of N,N'-(4,4'-methanediyl-diphenyl) biscarbamic Acid Diphenyl Ester Continuing, a reaction was carried out using an apparatus like that shown in FIG. 15.

SUS reaction vessel 1504 was heated to 220° C. and the pressure inside the reaction vessel was reduced to 1.3 kPa. A gaseous phase component was extracted from line F4, and the gaseous phase component was continuously fed to the middle stage of continuous multistage distillation column 1506 packed with Dickson packing (diameter: 6 mm) and having an inner diameter of about 5 cm and column length of 2 m to carry out distillative separation of the gaseous phase component. The amount of heat required for distillative separation was supplied by circulating the liquid in the bottom of the column through line F6 and reboiler 1507. The liquid temperature in the bottom of the continuous multistage distillation column 1506 was 200° C., and the pressure at the top of the column was 60 kPa. Gas distilled from the top of continuous multistage distillation column 1506 was condensed in condenser 1505 via line F5 and continuously extracted from line F7. A liquid phase component was extracted from line F6.

The liquid phase component extracted from line F6 was continuously fed to the middle stage of continuous multistage distillation column 1509 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line F11 and reboiler 1510. The liquid temperature in the bottom of continuous multistage distillation column 1509 was 210° C., and the pressure at the top of the column was about 2.5 kPa. Gas distilled from the top of continuous multistage distillation column 1509 was condensed in condenser 1508 via line F10 and continuously extracted via line F12. A liquid phase component was extracted from line F11.

A liquid phase component extracted from line F14 was continuously fed to the middle stage of continuous multistage distillation column 1512 packed with Dickson packing (diameter: 6 mm) and having an inner diameter of about 5 cm and column length of 2 m to carry out distillative separation of the liquid phase component. The amount of heat required for distillative separation was supplied by circulating the liquid in the bottom of the column through line F16 and reboiler 1513. The liquid temperature in the bottom of continuous multistage distillation column 1512 was 220° C., and the pressure at the top of the column was about 0.5 kPa. Gas distilled from the top of continuous multistage distillation column 1512 was condensed in condenser 1511 via line F15 and continuously extracted via line F17. The amount of liquid extracted from line F17 was about 70 g, and contained about 99.9% by weight of 4,4'-diphenylmethane diisocyanate. The yield based on 4,4'-methylenedianiline was 56.0%.

Comparative Example 3

Step (C-1): Production of N,N'-hexanediyl-bis-carbamic Acid Diphenyl Ester

A reaction was carried out using an apparatus like that shown in FIG. 7.

2454 g (11.5 mol) of diphenyl carbonate were supplied to baffled reaction vessel 704 made of SUS and having an inner volume of 5 L from storage tank 701 via line 71 with line 74 closed. The liquid temperature inside reaction vessel 704 was adjusted to about 80° C. to melt the diphenyl carbonate, and 372 g (3.2 mol) of hexamethylene diamine were supplied to reaction vessel 704 from storage tank 703 via line 73 at the rate of about 100 g/hr.

As a result of analyzing the solution following the reaction by liquid chromatography, N,N'-hexanediyl-bis-carbamic acid diphenyl ester was found to have been formed at a yield of 77.5%.

Line 74 was opened and the reaction liquid was transferred to storage tank 705 via line 74.

Step (C-2): Production of Isocyanate by Thermal Decomposition of N,N'-hexanediyl-bis-carbamic Acid Diphenyl Ester A reaction was carried out using an apparatus like that shown in FIG. 8.

A process was carried out in the same manner as step (1-2) of Example 1 with the exception of using the mixture obtained in step (C-1) instead of the mixture obtained in step (1-1).

Liquid was continuously extracted into storage tank 809 through line 92 at the rate of about 113 g/hr.

The liquid extracted from line 92 was a solution containing about 99.8% by weight of hexamethylene diisocyanate. The yield based on hexamethylene diamine was 74.4%.

Comparative Examples 4 to 6

The procedure of Example 6 was carried out continuously and various cleaning solvents were used every 10 days to carry out the cleaning procedure using the same method as Example 13. Those results are shown in Table 1.

TABLE 1

Results of Carrying Out Cleaning Procedure

| | Temperature in thin film distillation apparatus | Cleaning solvent | Cleaning solvent supply rate | Cleaning time | Results |
|---|---|---|---|---|---|
| Example 20 | 200° C. | 2,6-dimethylphenol | 1000 g/hr | 2 hr | ○ |
| Example 21 | 210° C. | 2,4,6-trimethylphenol | 800 g/hr | 2 hr | ○ |
| Example 22 | 250° C. | 2-phenylphenol | 1000 g/hr | 3 hr | ○ |
| Example 23 | 280° C. | 2,4(α,α-dimethylbenzyl)phenol | 1200 g/hr | 1 hr | ○ |
| Example 24 | 200° C. | 4-ethoxyphenol | 1100 g/hr | 2 hr | ○ |
| Example 25 | 270° C. | 4-dodecylphenol | 1300 g/hr | 1 hr | ○ |
| Example 26 | 200° C. | Salicylic acid | 800 g/hr | 2 hr | ○ |
| Example 27 | 220° C. | Benzoic acid | 800 g/hr | 4 hr | ○ |
| Comp. Ex. 4 | 200° C. | n-dodecane | 1000 g/hr | 4 hr | X |
| Comp. Ex. 5 | 200° C. | Naphthalene | 1000 g/hr | 4 hr | X |
| Comp. Ex. 6 | 180° C. | 1-phenyl ethanol | 1000 g/hr | 4 hr | X |

○: Adhered substances not observed after cleaning procedure
X: Adhered substances observed after cleaning procedure

INDUSTRIAL APPLICABILITY

Since the isocyanate production process according to the present invention enables isocyanate to be efficiently produced without using highly toxic phosgene, the production process of the present invention is highly useful industrially and has high commercial value.

We claim:

1. A process for producing an isocyanate, comprising the steps of:
    obtaining a reaction mixture containing an aryl carbamate having an aryl group originating from a diaryl carbonate, an aromatic hydroxy compound originating from a diaryl carbonate, and a diaryl carbonate, by reacting a diaryl carbonate comprising metal atoms at from 0.001 ppm to 10% and an amine compound in a reaction vessel in which a reaction between the diaryl carbonate and the amine compound is carried out;
    transferring the reaction mixture to a thermal decomposition reaction vessel connected by a line with the reaction vessel in which the reaction between the diaryl carbonate and the amine compound is carried out; and
    obtaining the isocyanate by applying the aryl carbamate to a thermal decomposition reaction, wherein a low boiling point component formed in the thermal decomposition reaction is recovered from the thermal decomposition reaction vessel in the form of a gaseous phase component, and a liquid phase component is recovered from a bottom of the reaction vessel, and the recovery of the gaseous phase component and the recovery of the liquid phase component are carried out continuously;
    wherein the amine compound is a polyamine compound; and
    an acid cleaning solvent is present in the thermal decomposition reaction.

2. The process according to claim 1, further comprising cleaning a high boiling point by-product adhered to the thermal decomposition reaction vessel, with an acid.

3. The process according to claim 1, wherein the reaction between the diaryl carbonate and the amine compound is carried out at a stoichiometric ratio of the diaryl carbonate to amino groups constituting the amine compound being 1 or more.

4. The process according to claim 1, wherein the diaryl carbonate and the amine compound are reacted in the presence of an aromatic hydroxy compound as a reaction solvent.

5. The process according to claim 4, wherein the aromatic hydroxy compound as the reaction solvent is an aromatic hydroxy compound having the same type as a compound ArOH having a structure in which a hydrogen atom is added to an ArO group constituting the diaryl carbonate ArOCOOAr (wherein Ar represents an aromatic group and O represents an oxygen atom).

6. The process according to claim 1, wherein the reaction mixture is supplied to the thermal decomposition reaction vessel in a form of a liquid.

7. The process according to claim 6, wherein the reaction mixture is supplied to the thermal decomposition reaction vessel while maintaining a temperature range of from 10 to 180° C.

8. The process according to claim 1, wherein the reaction mixture is continuously supplied to the thermal decomposition reaction vessel.

9. The process according to claim 1, wherein the isocyanate obtained by a thermal decomposition reaction of the aryl carbamate is recovered from the thermal decomposition reaction vessel in a form of a gaseous phase component, and a liquid phase component containing the diaryl carbonate is recovered from the bottom of the reaction vessel.

10. The process according to claim 9, further comprising recovering the isocyanate by distillative separation, with a distillation column, of the gaseous phase component containing the isocyanate recovered from the thermal decomposition reaction vessel, and supplying the gaseous phase component containing the isocyanate recovered from the thermal decomposition reaction vessel to the distillation column in a form of a gaseous phase.

11. The process according to claim 9, wherein the liquid phase component containing the diaryl carbonate is a mixture containing the aryl carbamate, and all or a portion of the mixture is supplied to an upper portion of the reaction vessel.

12. The process according to claim 1, wherein the isocyanate obtained by the thermal decomposition reaction of the aryl carbamate is recovered from the bottom of the reaction vessel in which the thermal decomposition reaction is carried out in a form of a liquid phase component.

13. The process according to claim 12, wherein the liquid phase component recovered from the bottom of the reaction vessel comprises the isocyanate and the aryl carbamate, all or a portion of the isocyanate is separated from the liquid phase component, and all or a portion of a remainder is supplied to the upper portion of the reaction vessel.

14. The process according to claim 12, wherein the isocyanate is recovered by distillative separation of a mixture containing the isocyanate recovered from the thermal decomposition reaction vessel.

15. The process according to claim 1, wherein a type of the reaction vessel in which the reaction between the diaryl carbonate and the amine compound is carried out and a type of the thermal decomposition reaction vessel may be the same or different, and the reaction vessel in which the reaction between the diaryl carbonate and the amine compound is carried out and the thermal decomposition reaction vessel is at least one reaction vessel selected from the group consisting of a column-type reaction vessel and a tank-type reaction vessel.

16. The process according to claim 15, wherein the thermal decomposition reaction vessel is composed of at least one reaction vessel selected from the group consisting of an evaporator, a continuous multistage distillation column, a packed column, a thin film evaporator and a falling film evaporator.

17. The process according to claim 1, wherein the reaction between the diaryl carbonate and the amine compound is carried out in the presence of a catalyst.

18. The process according to claim 1, wherein the thermal decomposition reaction is carried out in a liquid phase.

19. The process according to claim 1, wherein the diaryl carbonate is a compound represented by the following formula (1):

(1)

wherein $R^1$ represents an aromatic group having 6 to 12 carbon atoms.

20. The process according to claim 1, wherein the metal atom is selected from the group consisting of iron, nickel, cobalt, zinc, tin, copper, titanium atoms and mixtures thereof.

21. The process according to claim 1, wherein the diaryl carbonate is a diaryl carbonate produced by a process which comprises the following steps (1) to (3):

step (1): obtaining a reaction mixture containing a dialkyl carbonate by reacting an organic tin compound having a tin-oxygen-carbon bond and carbon dioxide;

step (2): obtaining the dialkyl carbonate and a residue liquid by separating the reaction mixture; and step (3): obtaining the diaryl carbonate by reacting the dialkyl carbonate separated in step (2) and an aromatic hydroxy compound A followed by recovering a by-product alcohol.

22. The process according to claim 21, wherein the aromatic hydroxy compound A is an aromatic hydroxy compound having 6 to 12 carbon atoms.

23. The process according to claim 21, wherein the diaryl carbonate is a diaryl carbonate produced by a process which further comprises the following steps (4) and (5):

step (4): forming an organic tin compound having a tin-oxygen-carbon bond and water by reacting the residue liquid obtained in step (2) with an alcohol followed by removing the water from a reaction system; and step (5): reusing the organic tin compound having the tin-oxygen-carbon bond obtained in step (4) as the organic tin compound having a tin-oxygen-carbon bond of step (1).

24. The process according to claim 21, wherein the alcohol recovered in step (3) is used as all or a portion of the alcohol of the step (4).

25. The process according to claim 1, wherein the diaryl carbonate is separated and recovered from the liquid phase component or gaseous phase component recovered from the thermal decomposition reaction vessel, and the diaryl carbonate is reused as a diaryl carbonate used as a starting material.

26. The process according to claim 1 or 21, wherein an aromatic hydroxy compound is separated and recovered from the liquid phase component or gaseous phase component recovered from the thermal decomposition reaction, and the aromatic hydroxy compound is recycled for use as the aromatic hydroxy compound A of the step (3) or as the aromatic hydroxy compound used as the reaction solvent.

27. The process according to claim 1, wherein the amine compound is a compound represented by the following formula (2):

$$R^2 \!-\!\!\!+\!\! NH_2)_n \qquad (2)$$

wherein $R^2$ represents a group selected from the group consisting of an aliphatic group having 1 to 20 carbon atoms and an aromatic group having 6 to 20 carbon atoms, the above group containing an atom selected from a carbon atom and an oxygen atom, and having a valence equal to n, and n represents an integer of from 2 to 10.

28. The process according to claim 27, wherein the amine compound is a diamine compound in which n is 2 in the formula (2).

29. The process according to claim 1, wherein the supply of the amine compound to the reaction vessel in which a carbonic acid ester and the amine compound are reacted is carried out in a liquid state.

30. The process according to claim 1, wherein the supply of the amine compound to the reaction vessel in which a carbonic acid ester and the amine compound are reacted is carried out in a form of a mixture comprising an alcohol, a water or the carbonic acid ester.

31. The process according to claim 1, wherein the diaryl carbonate comprises the metal atoms at from 0.001 ppm to 5%.

32. The process according to claim 1, wherein the diaryl carbonate comprises the metal atoms at from 0.001 ppm to 3%.

33. The process according to claim 1, wherein the metal atoms present in a form of metal ions or in a form of individual metal atoms.

34. The process according to claim 1, wherein the metal atoms do not have catalytic action in the reaction between the diaryl carbonate and the amine compound.

* * * * *